(12) United States Patent
Peet et al.

(10) Patent No.: US 6,413,951 B2
(45) Date of Patent: Jul. 2, 2002

(54) 20-FLUORO-17(20)-VINYL STEROIDS

(75) Inventors: Norton P. Peet, North Andover, MA (US); Philip M. Weintraub, Warren, NJ (US); Joseph P. Burkhart, Plainfield, IN (US); Cynthia A. Gates, Cambridge, MA (US)

(73) Assignee: Aventis Pharmaceuticals, Inc., Bridgewater, NJ (US)

( * ) Notice: Subject to any disclaimer, the term of this patent is extended or adjusted under 35 U.S.C. 154(b) by 0 days.

(21) Appl. No.: 09/886,818

(22) Filed: Jun. 21, 2001

Related U.S. Application Data

(60) Provisional application No. 60/290,881, filed on May 14, 2001, and provisional application No. 60/214,561, filed on Jun. 27, 2000.

(30) Foreign Application Priority Data

Jan. 19, 2001 (GB) .............................................. .0101523

(51) Int. Cl.$^7$ .......................... A61K 31/56; C07J 13/00; C07J 41/00

(52) U.S. Cl. ....................... 514/177; 514/182; 552/515; 552/530; 552/532

(58) Field of Search ................................ 514/177, 182; 552/515, 530, 532

(56) References Cited

U.S. PATENT DOCUMENTS

| | | |
|---|---|---|
| 3,361,743 A | 1/1968 | Benn |
| 3,597,418 A | 8/1971 | Campbell et al. |
| 5,792,757 A * | 8/1998 | Jennings-White et al. .. 514/170 |

FOREIGN PATENT DOCUMENTS

| | | |
|---|---|---|
| JP | 43021058 | 9/1968 |
| WO | 9833506 | 6/1998 |

OTHER PUBLICATIONS

Jean P. Van Wauve et al., "Is There a Case for P–450 Inhibitors in Cancer Treatment?" J. Med. Chem. 32, 2231–2239 (1989).

Michael S. Cookson and Michael F. Sarosdy, "Hormonal Therapy for Metastatic Prostate Cancer: Issues of Timing and Total Androgen Ablation" South. Med. J., 87, 1–6 (1994).

Edward J. Parish and Hiroshi Honda, "A Facile Synthesis of Steroidal $\Delta^4$–3–Ketones Using Pyridinium Chlorochromate (PCC)" Syn. Commun., 20, 1167–1174 (1990).

Jurgen Westermann and Klaus Nickisch, "Copper–Catalyzed 1,4–Additions of Trialkylaluminum Compounds to Enones" Angew. Chem. Int. Ed. Engl., 32, 1368–1370 (1993).

J. Iriarte and H.J. Ringold, "Steroids XCIV. Synthesis of 2–Methyl– and 1,2–Dimethyl–Estrogens" Tetrahedron, 3, 28–36 (1958).

H.J. Ringold and G. Rosenkranz, "Steroids LXXXIII. Syntheisi of 2–Methyl and 2,2–Dimethyl Hormone Analogs" J. Org. Chem., 21, 1333–1335 (1956).

K. Tsuda and S. Nozoe, "Steroid Studies. XI[1]. On the Methylation of 3–Oxosteroids (1)." Chem Pharm. Bull. (Tokyo), 7, 232–238 (1959).

K. Tsuda and S. Nozoe, "Steroid Studies. XII[1]. On the Methylation of 3– Oxosteroids (2)." Chem Pharm. Bull. (Tokyo), 7, 238–240 (1959).

Norman W. Atwater, "4–Substituted Steroids" J. Am. Chem. Soc., 82, 2847–2852 (1960).

F. Sondheimer and Y. Mazur, "Synthesis of 4–Methylated Steroids" J. Amer. Chem. Soc., 79, 2906–2910 (1957).

D.N. Krik et al., "Modified Steroid Hormones. Part III. Some 4–Chloro–3–oxo–$\Delta^4$–Derivatives" J. Chem. Soc., 1184–1186 (1956).

Timothy T. Curran et al., "A Novel Route to a 4–Amino Steroid: MDL 19687" Tetrahedron Lett., 36, 4761–4764 (1995).

(List continued on next page.)

Primary Examiner—Barbara P. Badio
(74) Attorney, Agent, or Firm—Lawrence L. Martin; Stephen L. Nesbitt

(57) ABSTRACT

The invention relates to 20$\xi$-fluoropregna-4,17(20)-dien-3-on-21-oic acid ethyl ester, 20$\xi$-fluoro-3$\beta$-hydroxypregna-5,17(20)-dien-21-oic acid ethyl ester, 20$\xi$-fluoro-21-hydroxypregna-4,17 (20)-dien-3-one, 20$\xi$-fluoropregna-5,17(20)-dien-3$\beta$,21-diol and related compounds and to compositions incorporating these compounds, as well as the inhibition of $C_{17,20}$ lyase, 5$\alpha$-reductase and $C_{17}$-hydroxylase, and to the use of these compounds in the treatment of androgen and estrogen mediated or dependent disorders, including benign prostatic hyperplasia, prostate cancer, breast cancer and DHT-mediated disorders such as acne and hirsutism. Treatment of disorders related to the over synthesis of cortisol, for example, Cushing's Syndrome are also included. The treatment of androgen-dependent disorders also includes a combination therapy with known androgen-receptor antagonists, such as flutamide. The compounds of the invention have the following general formulae:

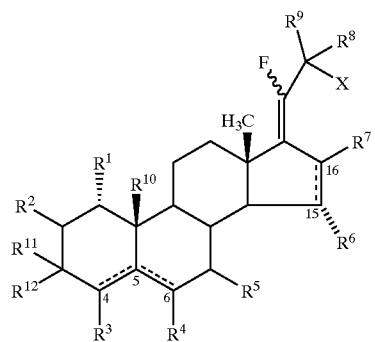

40 Claims, No Drawings

OTHER PUBLICATIONS

Mitsuteru Numazawa and Mariko Oshibe, "6–Alkyl and 6–Arylandrost–4–ene–3,17–diones as Aromatase Inhibitors, Synthesis and Structure Activity Relationships" J. Med. Chem., 37, 1312–1319 (1994).

Joyce F. Grunwell et al., "Antiprogestational Agents. The Synthesis of 7–Alkyl Steroidal Ketones with Anti–Implantational and Antidecidual Activity" Steroids, 27, 759–771 (1976).

Anthony Y. Reeder and George E. Joannou, "15β–Hydroxysteroids (Part I). Steroids of the Human Perinatal Period: The Synthesis of 3β, 15β, 17α–trihydroxy–5–pregnen–20–one" Steroids, 61, 74–81 (1996).

Carl Djerassi et al., "The Direct Conversion of Steroidal $\Delta^5$–3β–Alcohols to $\Delta^5$– and $\Delta^4$–3–Ketones" J. Org. Chem., 21, 1547–1549 (1956).

John P. Dusza et al, "C–6 Hydroxylated Sterioids, III. A New Preparative Method" J. Org. Chem., 27, 4046–4049 (1962).

D. Burn et al., "Modified Steroid Hormones—XXXIII Steroidal 6–Formyl–3–alkoxy–3,5–dienes and Some of Their Transformations" Tetrahedron, 20, 597–609 (1964).

Arnold I.A. Broess et al., "Synthetic Approaches Toward Total Synthesis of 12β–Methyl– and 12–Methylene–19–norpregnanes" Steroids, 57, 514–521 (1992).

Gerald L. Schatzman et al., "A Normal Phase High–Performance Liquid Chromatography System for Steroid 17α–Hydroxylase/$C_{17-20}$ Lyase (Cytochrome P–$450_{21scc}$) Assays" Anal. Biochem., 175, 219–226 (1988).

Ronald J. Moore and Jean D. Wilson, "Reduced Nicotinamide Adenine Dinucleotide Phosphate: $\Delta^4$–3–Ketosteroid 5α–Oxidoreductase (Rat Ventral Prostate)" Methods in Enzymol., 36, 466–474 (1975).

W. W. Cleland, "The Kinetics of Enzyme–Catalyzed Reactions with Two or More Substrates or Products" Biochem. Biophys. Acta., 67, 188–196 (1963).

Ronald G. Duggleby, "Regression Analysis of Nonlinear Arrhenius Plots: An Empirical Model and a Computer Program" Comput. Biol. Med., 14, 447–455 (1984).

Norton P. Peet, "Drugs for Treating Diseases of the Prostate" Invited Lecture presented at Scripps Research Institute: LaJolla, California: Sep. 21, 2000.

Philip M. Weintraub, "Drugs for Treating Diseases of the Prostate" Book of Abstracts, 2000 International Congress of Pacific Basin Societies, Honolu, Hawaii, Dec. 17, 2000, Abstract MEDI 301.

* cited by examiner

20-FLUORO-17(20)-VINYL STEROIDS

This application claims the benefit of U.S. Provisional Application No. 60/214,561, filed Jun. 27, 2000, and U.S. Provisional Application No. 60/290,881, filed May 14, 2001.

BACKGROUND OF THE INVENTION

1. Field of the Invention

The present invention relates to 20-fluoropregna-5,17(20)-diene-3β,21-diol, 20-fluoro-pregna-5,17(20)-dien-3β-ol and related compounds, to processes for their preparation, and to compositions incorporating these compounds as well as the use of these compounds in the treatment of conditions which would be affected by inhibition of $C_{17,20}$ lyase and/or 5α-reductase, including androgen and estrogen mediated or dependent disorders, such as, for example benign prostatic hyperplasia; dihydrotestosterone-mediated disorders such as, for example, acne; estrogen dependent breast cancer and androgen mediated prostatic cancer. The present invention provides a novel series of compounds which also disable the operation of $C_{17}$-hydroxylase; thus, disorders that are characterized by an oversynthesis of cortisol can also be treated by the compounds of the invention. For example, hypokalemia, metabolic alkalosis, polydipsia, polyurea, Cushing's syndrome and hypertensive conditions.

2. Description of the Art

The enzyme steroid $C_{17,20}$ lyase cleaves the 17–20 carbon-carbon bond in steroids having a two carbon side chain at the 17β-carbon position to form important precursor molecules for the formation of testosterone, 5α-dihydrotestosterone and the estrogens, principally estrone and estradiol. Compounds which inhibit this enzyme would thus serve to inhibit the formation of the indicated precursors and thereby be useful in the treatment of various androgenic as well as estrogenic disorders. A treatment incorporating such enzymatic inhibitors is not limited to the origin of the precursor molecule, such as various organ ablation techniques which are currently known. For example, while orchiectomy will effectively reduce gonadal androgen, it will have not have significant effect upon adrenal androgen production. Moreover, such an enzymatic treatment is a much more focused treatment in that it is directed to the immediate hormonal imbalance believed responsible for the condition, as opposed to a broad spectrum remedy which not only affects the particular symptom, but causes permanent endocrine deficits necessitating life-long dependency on replacement therapy.

It is further known that certain types of breast cancers are estrogen dependent. Adrenalectomy, ovariectomy and hypophysectomy have been employed as well as non-surgical techniques resulting in tumor regressions. It has been shown that human patients with advanced breast cancer, who are administered estrogen biosynthesis enzyme inhibitors, show dramatically reduced plasma estradiol levels and improved therapeutic effects, at least as effective as adrenalectomy. [Van Wauve, J. and Janssen, P. A. J., *J. Med. Chem.* 1989, 32, 2231–2239].

Prostatic cancer, or neoplastic tissue disorders which originate in the parenchymal epithelium of the prostate, is one of the most common malignancies among men, and exhibits one of the highest cancer-specific deaths of all malignant carcinomas. It is known that patients with metastatic prostate cancer respond positively to hormonal therapy. It is reported by Cookson and Sarosdy that androgen ablation has had a positive, beneficial response for as high as 60% to 80% of all patients tested. [Cookson, C. S. and Sarosdy, M. F., *South Med. J.* 1994, 87, 1–6].

More specifically, $C_{17,20}$ lyase inhibitors would be useful in the treatment of hormonal dependent prostatic carcinorna, prostatic hyperplasia, virilism, congenital adrenal hyperplasia due to 21-hydroxylase deficiency, hirsutism, hormonal dependent breast cancer, polycystic ovarian syndrome correlated with elevated $C_{17,20}$ lyase activity as well as other neoplastic tissue disorders such as endometrial, hepatocellular and adrenal carcinomas.

The enzyme steroid 5α-reductase, present in mammalian tissues including skin, male genitalia and the prostate, catalyzes the conversion of testosterone (17β-hydroxyandrost-4-en-3-one) into dihydrotestosterone or DHT (17β-hydroxy-5α-androstan-3-one), which is also known as stanolone. DHT is a more potent androgen than testosterone, and acts as an end-organ effector in certain tissues, particularly in mediating growth. DHT formation can occur in certain tissues themselves by the action of 5α-reductase. The conversion of testosterone to DHT itself can be associated with various androgenic disorders, especially when DHT levels build up to excessive amounts. For example, high levels of DHT in the skin has been associated in the pathogenesis of acne, including acne vulgaris. In the treatment of androgen mediated or androgen dependent disorders, such as acne, benign prostatic hyperplasia and prostatic cancer, including hormonal dependent carcinoma, the inhibition of DHT would be highly desirable.

Agents that have the ability to inhibit both $C_{17,20}$ lyase and 5α-reductase would not only inhibit DHT production, but also testosterone formation. In inhibiting the principal androgenic steroidal hormones, such compounds would have enhanced utility in the treatment of androgen mediated or dependent disorders.

The enzyme $C_{17}$ hydroxylase catalyzes the $C_{17}$ hydroxylation of steroid substrates during the biosynthesis of cortisol. As $C_{17,20}$ lyase and $C_{17}$ hydroxylase are the same active site of the same enzyme, the inhibition of one usually results in the inhibition of the other. Cortisol excess results in a syndrome characterized by hypokalemia, metabolic alkalosis, polydipsia, polyuria, Cushing's syndrome and hypertensive conditions. Inhibition of cortisol synthesis via $C_{17}$ hydroxylase would, therefore, have a beneficial therapeutic effect for the treatment of these disorders or conditions.

SUMMARY OF THE INVENTION

More particularly, the present invention is directed to a group of compounds, and to their pharmaceutically acceptable salts, of the formula:

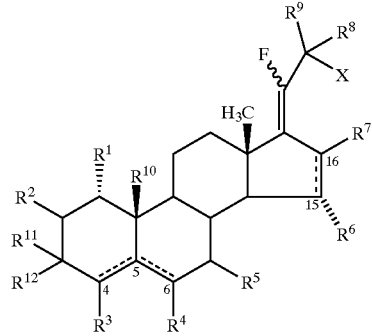

wherein:
$R^1$ is H or $C_{1-4}$ alkyl;
$R^2$ is H or $C_{1-4}$ alkyl;

$R^3$ is H, chloro, nitro, amino or $C_{1-4}$ alkyl;

$R^4$ is H or $C_{1-4}$ alkyl;

$R^5$ is H or $C_{1-4}$ alkyl;

$R^6$ is H or methyl;

$R^7$ is H or methyl;

$R^8$ is H or methyl;

$R^9$ is H or methyl;

or $R^8$ and $R^9$ taken together is oxo;

$R^{10}$ is H or methyl;

$R^{11}$ is H;

$R^{12}$ is hydroxy;

or $R^{11}$ and $R^{12}$ taken together is oxo;

X is H, hydroxy or methoxy;

with the proviso that when:

a) $R^{11}$ is H and $R^{12}$ is hydroxy, bond $C_{4,5}$ is a single bond, bond $C_{5,6}$ is a double bond and bond $C_{15,16}$ is optionally a single bond or a double bond, and b) $R^{11}$ and $R^{12}$ taken together is oxo, bond $C_{4,5}$ is a double bond, bond $C_{5,6}$ is a single bond, and bond $C_{15,16}$ is a single bond.

Another embodiment of the invention provides use of the compounds of the invention as inhibitors of $C_{17,20}$ lyase and 5α-reductase for the treatment of androgen or estrogen mediated or dependent disorders such as breast cancer, polycystic ovarian syndrome, prostatic hyperplasia, prostatic cancer, virilism, hirsutism, and acne.

In another embodiment, the invention provides use of the compounds of the invention for the treatment of Cushing's syndrome.

In yet another embodiment, the invention provides a pharmaceutical composition comprising a compound of the invention and a pharmaceutically acceptable carrier.

In another embodiment, the compounds of the invention may be administered in combination with other effective treatments for enhanced therapeutic effect. For example, in the treatment of androgen-dependent disorders, including prostatic cancer, flutamide, a known androgen receptor antagonist, may be used in combination with compounds of the invention.

A preferred embodiment of the invention are compounds wherein $R^1$, $R^2$, $R^3$, $R^4$, $R^5$, $R^6$, $R^7$, $R^8$, $R^9$, $R^{10}$, $R^{11}$ and X are hydrogen, $R^{10}$ is methyl, $R^{12}$ is hydroxy, bond $C_{4,5}$ and bond $C_{15,16}$ are each a single bond and bond $C_{5,6}$ is a double bond.

A most preferred embodiment of the invention are compounds wherein $R^1$, $R^2$, $R^3$, $R^4$, $R^5$, $R^6$, $R^7$, $R^8$, $R^9$ and $R^{11}$ are hydrogen, $R^{10}$ is methyl, X and $R^{12}$ are each hydroxy, bond $C_{4,5}$ and bond $C_{15,16}$ are each a single bond and bond $C_{5,6}$ is a double bond.

DETAILED DESCRIPTION OF THE INVENTION

As used herein, the term "$C_{1-4}$ alkyl" means any straight or branched chain alkyl radical of one to four carbon atoms, for example, methyl, ethyl, n-propyl, i-propyl, n-butyl, s-butyl, or t-butyl.

As used herein, the following structural designations as used in the formulas shall have the following meanings: ⦀⦀⦀ is defined as a bond below the plane of the steroid (the α-face). ◄ is defined as a bond above the plane of the steroid (the β-face). ∿ is defined as a cis or trans bond (or mixture of the two) whose stereochemistry is not defined. ═══ is defined as an optional double bond.

As used herein, the term "pharmaceutically acceptable salt" is intended to apply to any salt, whether previously known or future discovered, that is used by one skilled in the art that is a non-toxic organic or inorganic addition salt which is suitable for use as a pharmaceutical. Illustrative bases which form suitable salts include alkali metal or alkaline-earth metal hydroxides such as sodium, potassium, calcium or magnesium hydroxides; ammonia and aliphatic, cyclic or aromatic amines such as methylamine, dimethylamine, triethylamine, diethylamine, isopropyldiethylamine, pyridine and picoline. Illustrative acids which form suitable salts include inorganic acids such as, for example, hydrochloric, hydrobromic, sulfuric, phosphoric and like acids, and organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic and like acids, and organic sulfonic acids such as methanesulfonic and p-toluenesulfonic acids.

As used herein "stereoisomer" is a general term used for all isomers of individual molecules that differ only in the orientation of their atoms in space. The term stereoisomer includes mirror image isomers (enantiomers), geometric (cis/trans or E/Z) isomers, and isomers of compounds with more than one chiral center that are not mirror images of one another (diastereoisomers).

As used herein, the term "effective inhibitory amount," is such an amount wherein an enzyme inhibitory effect is achieved to cause a therapeutic effect in a patient. The exact amount of compound to be administered can be readily determined by the attending diagnostician, as one skilled in the art, by the use of conventional techniques and by observing the results obtained under analogous circumstances. Factors significant in determining the dose include: the species of animal, the animal's size, age and general health; the specific disease or disorder involved, the degree of involvement or the severity of the disease; the response of the individual patient; the particular compound administered; the mode of administration; the bioavailability characteristics of the preparation administered; the dose regimen selected; the use of concomitant medication; and other relevant circumstances. That said, the exact amount employed may vary over a wide range, for example, from about 0.625 to 200 mg/kg of body weight per day, preferably from about 5 to 100 mg/kg of body weight per day.

"Treat" or "treating" means any treatment, including but not limited to, alleviating symptoms, eliminating the causation of the symptoms either on a temporary or permanent basis, or to preventing or slowing the appearance of symptoms and progression of the named disease, disorder or condition.

As described herein, the term "patient" refers to a warm blooded animal such as a mammal which is afflicted with a particular disease, disorder or condition. It is explicitly understood that guinea pigs, dogs, cats, rats, mice, horses, cattle, sheep, and humans are examples of animals within the scope of the meaning of the term.

In practicing the methods of this invention, the active ingredient is preferably incorporated into a composition containing a pharmaceutical carrier, although the compounds are effective and can be administered, in and of themselves. The term "pharmaceutical carrier" refers to known pharmaceutical excipients useful in formulating pharmaceutically active compounds for administration, and which are substantially nontoxic and nonsensitizing under conditions of use. The exact proportion of these excipients are determined by the solubility and chemical properties of the active compound, the chosen route of administration as well as standard pharmaceutical practice. That said, the proportion of active ingredient can vary from about 5 to 90% by weight.

FORMULATIONS

The pharmaceutical compositions of the invention are prepared in a manner well known in the pharmaceutical arts. The carrier or excipients may be a solid, semisolid or liquid material which can serve as a vehicle or medium for the active ingredient. Suitable carriers or excipients are well known in the art. The pharmaceutical composition may be adapted for oral, inhalation, parenteral or topical use, and may be administered to the patient in the form of tablets, capsules, suspensions, syrups, aerosols, inhalants, suppositories, salves, powders, solutions and the like. As used herein, the term "pharmaceutical carrier" means one or more excipients.

In preparing formulations of the compounds of the invention, care should be taken to ensure bioavailability of an effective inhibitory amount, including oral, parenteral and subcutaneous routes. For example, effective routes of administration may include subcutaneously, intravenously, transdermally, intranasally, rectally, vaginally and the like including release from implants as well as direct injection of the active ingredient and/or composition directly into the tissue or tumor sites. Suitable pharmaceutical carriers and formulation techniques are found in standard texts, such as *Remington: The Science and Practice of Pharmacy*, 19$^{th}$ edition, Volumes 1 and 2, 1995, Mack Publishing Co., Easton, Pa., U.S.A., which is herein incorporated by reference.

For oral administration, the compounds can be formulated into solid or liquid preparations, with or without inert diluents or edible carriers, such as capsules, pills, tablets, troches, powders, solutions, suspensions or emulsions. The capsules, pills, tablets, troches and the like may also contain one or more of the following adjuvants: binders such as microcrystalline cellulose, gum tragacanth; excipients such as starch or lactose, disintegrating agents such as alginic acid, corn starch and the like; lubricants such as stearic acid, magnesium stearate or Sterotex®, (Stokely-Van Camp Inc., Indianapolis, Ind.) glidants such as colloidal silicon dioxide; sweetening agents such as sucrose or saccharin; and flavoring agents such as peppermint, methyl salicylate or fruit flavoring. When the dosage unit form is a capsule, it may also contain a liquid carrier such as polyethylene glycol or a fatty oil. Materials used should be pharmaceutically pure and nontoxic in the amounts used.

For parenteral administration, the compound may be administered as injectable dosages of a solution or suspension of the compound in a physiologically acceptable diluent with a pharmaceutical carrier which can be a sterile liquid such as water-in-oil or without the addition of a surfactant and other pharmaceutically acceptable excipients. Illustrative oils which can be employed in the preparations are those of petroleum, animal, vegetable or synthetic origin such as, for example, peanut oil, soybean oil and mineral oil. In general, water, saline, aqueous dextrose and related sugar solutions, ethanol and glycols, such as propylene glycol are preferred liquid carriers, particularly for injectable solutions. The parenteral preparation can be enclosed in ampoules, disposable syringes or multiple dose vials made of inert plastic or glass.

The solutions or suspensions described above may also include one or more of the following adjuvants: sterile diluents such as water for injection, saline solution, fixed oils, polyethylene glycols, glycerin, propylene glycol or other synthetic solvents, antibacterial agents such as ascorbic acid or sodium bisulfite; chelating agents such as ethylenediaminetetra-acetic acid; buffers such as acetates, citrates or phosphates and agents for the adjustment of tonicity such as sodium chloride or dextrose.

The compounds can be administered in the form of a cutaneous patch, a depot injection or implant preparation which can be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers and synthetic silicones. Further information on suitable pharmaceutical carriers and formulation techniques are found in standard texts such as *Remington: The Science and Practice of Pharmacy*, 19$^{th}$ edition, Volumes 1 and 2, 1995, Mack Publishing Co., Easton, Pa., U.S.A.

CHEMICAL SYNTHESES

The compounds of the present invention can be prepared by processes analogous to those known in the art. Reaction schemes A to O and the corresponding descriptive text describe the preparation of the various compounds of the invention. The methods disclosed and examples are provided for illustration purposes and in no way limit the scope of the present invention. Alternative reagents, reaction conditions, and other combinations and permutations of the steps herein described to arrive at individual compounds are readily apparent to one of ordinary skill in the art.

List of Abbreviations

DIBALH=diisobutylaluminum hydride; DMAP=4-dimethylaminopyridine; DMF=dimethylformamide; LAH=lithium aluminum hydride; LHMDS=lithium hexamethyldisilazide; NBS=N-bromosuccinimide; PCC=pyidinium chlorochromate; PDC=pyridinium dichromate; Pyr. $SO_3$=sulfur trioxide pyridine complex; TBAF=tetrabutylammuonium fluoride; TBDMS=t-butyldimethylsilyl; TEA=triethylamine; THF=tetrahydrofuran; $Ac_2O$=acetic anhydride; TsOH=tosic acid (p-toluenesulphonic acid); ξ=designation for undefined geometry about a double bond, g=grams; mmol=millimole, mL=milliliters; bp=boiling point; mp=melting point; ° C.=degrees Celsius; mm Hg=millimeters of mercury; $\mu$L=microliters, mm Hg=millimeters of mercury; $\mu$g=micrograms; $\mu$M=micromolar; mM=millimolar; $\mu$Ci=microcurie; M=molar; NADPH=hydrogenated nicotinamide adenine dinucleotide phosphate; DMSO=dimethylsulfoxide; EDTA=ethylenediaminetetraacetic acid; HPLC=high performance liquid chromatography.

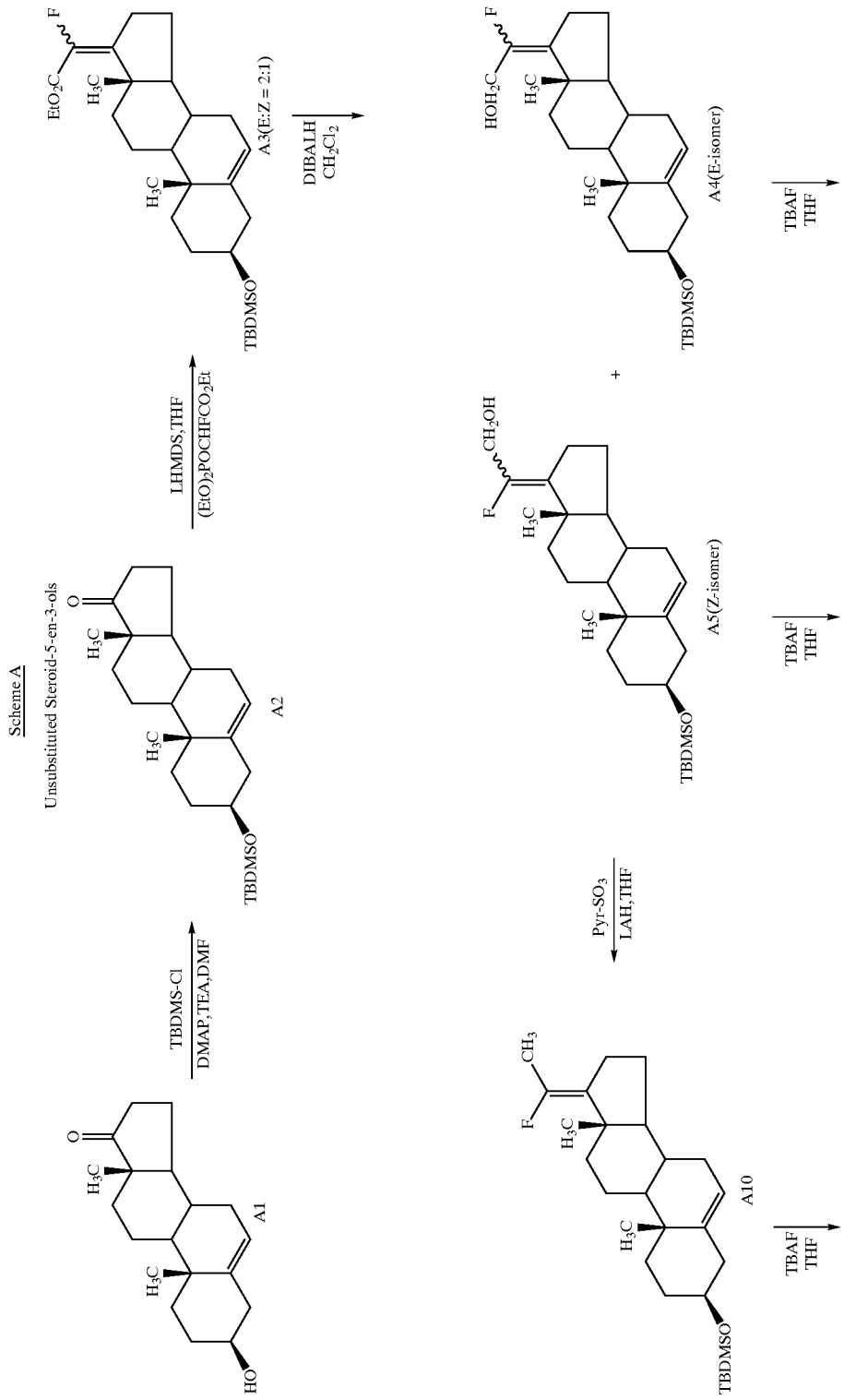

-continued
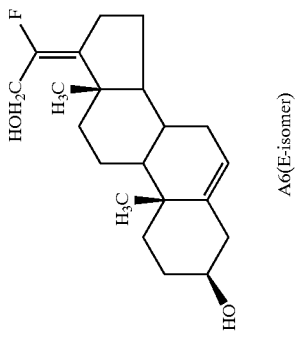
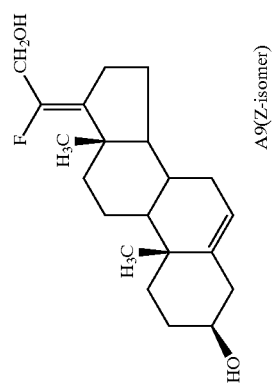
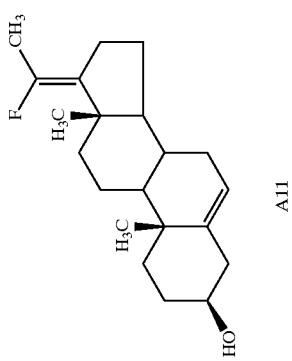
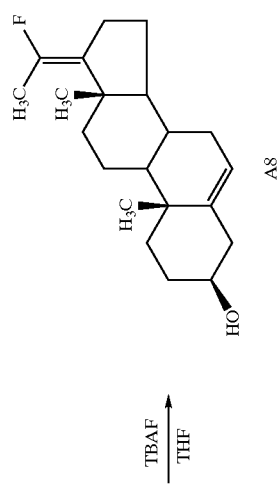
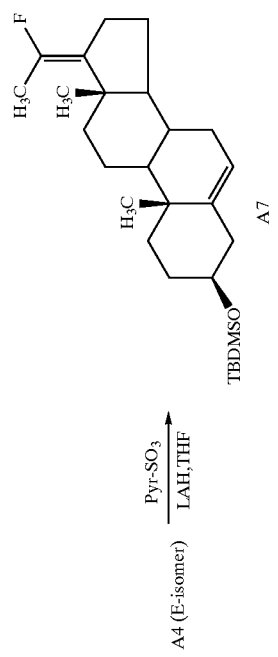

Scheme B
C21 Substituted Steroid-5-en-3-ols
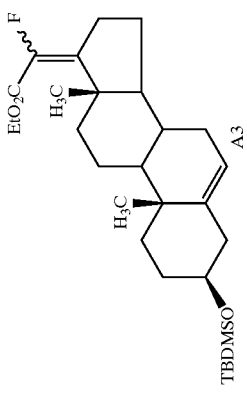
A3
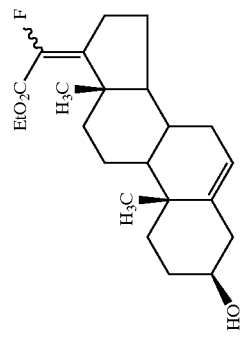
B12
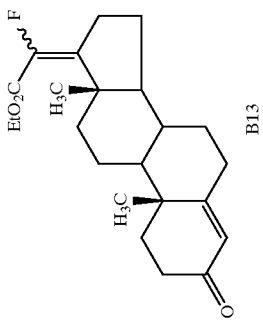
B13
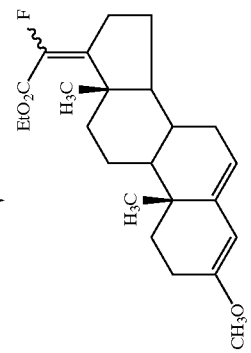
B14
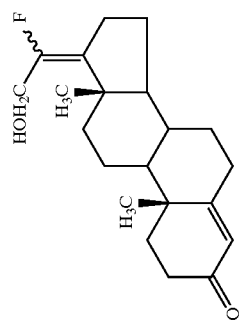
B15
B16
B17

The unsubstituted steroid-5-en-3-ols of this invention may be prepared by as depicted in Scheme A. Protecting the hydroxyl group of dehydroepiandrosterone (A1) by reaction with t-butyldimethylsilyl chloride gives silyl ether A2. Wittig reaction on the $C_{17}$ ketone of A2 with the ylid formed by reaction of triethyl 2-fluoro-2-phosphonoacetate with a suitable base such as lithium hexamethyldisilazide gives vinyl fluoride ester A3 as a mixture of E- and Z-isomers. A suitable base in this instance is any base that will function to form a ylid by reaction with triethyl 2-fluoro-2-phosphonoacetate such as, for example, lithium hexamethyldisilazide, alkyl lithium bases such as t-butyllithium, potassium t-butoxide and the like. Separation of the isomers is possible, but difficult at this point, so it is usually done after the next step. Reduction of ester A3 is accomplished with a suitable reducing agent such as diisobutylaluminum hydride in dichloromethane to give a mixture of hydroxymethyl vinyl fluorides which are separated into the individual E- and Z-isomers A4 and A5, respectively. Removal of the silyl protecting group of E-olefin A4 with tetrabutylammonium fluoride gives diol A6. Similarly, the silyl protecting group of Z-olefin A5 is removed to yield diol A9. Further reduction of alcohol A4 or A5 using sulfur trioxide pyridine complex in tetrahydrofuran followed by treatment with lithium aluminum hydride gives the corresponding $C_{21}$ deoxy derivatives A7 and A10, respectively. Removal of the silyl protecting groups from A7 and A10 as described above gives alcohols A8 and A16, respectively.

The $C_{21}$, substituted steroid-5-en-3-ols of this invention may be prepared following the methodology depicted in Scheme B. Using the mixture of vinyl fluoride esters A3 as starting material, the following transformations can be accomplished. The silyl group of A3 is removed using tetrabutylammonium fluoride giving alcohol B12. The latter is oxidized with pyridinium chlorochromate (see Parish, E. J. and Honda, H. *Syn. Commun.*, 1990, 20, 1167–1174) to give conjugated ketone B13. Reduction of the ester group of compound B13 required a two step sequence. Thus, treating B13 with trimethyl orthoformate in the presence of tosic acid provides dienol ether B14, and then the ester of B14 is reduced with DIBALH in methylene chloride ($CH_2Cl_2$). If the work-up involves treatment with dilute hydrochloric acid, hydroxy-enone B15 is isolated. Addition of excess methyl Grignard to A3 gives tertiary alcohol B16. Careful removal of the silyl protecting group from B16 with tetrabutylammonium fluoride in tetrahydrofuran gives the desired diol B17.

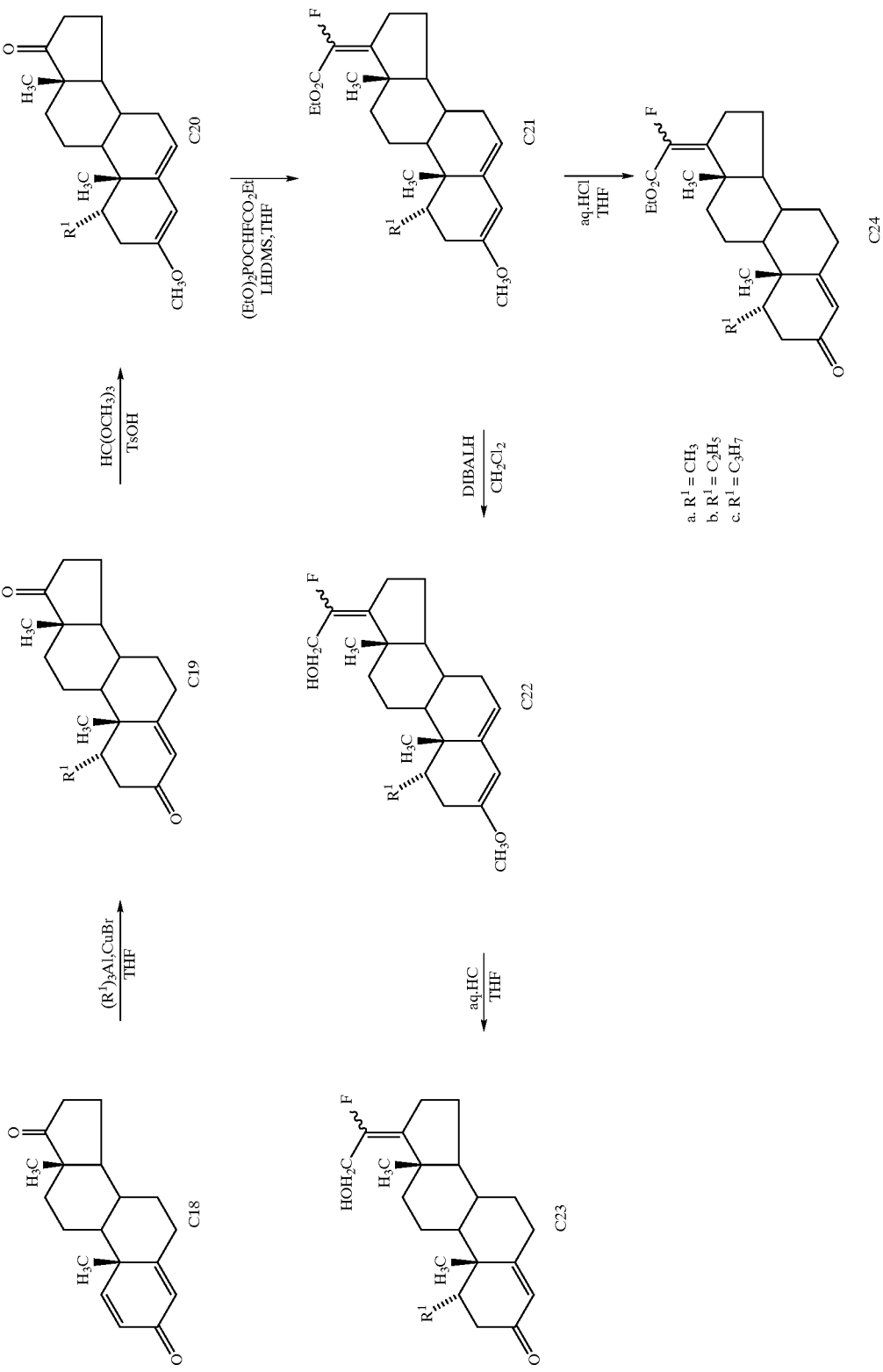

Scheme D

C₁ Substituted Steroid-5-en-3-ols

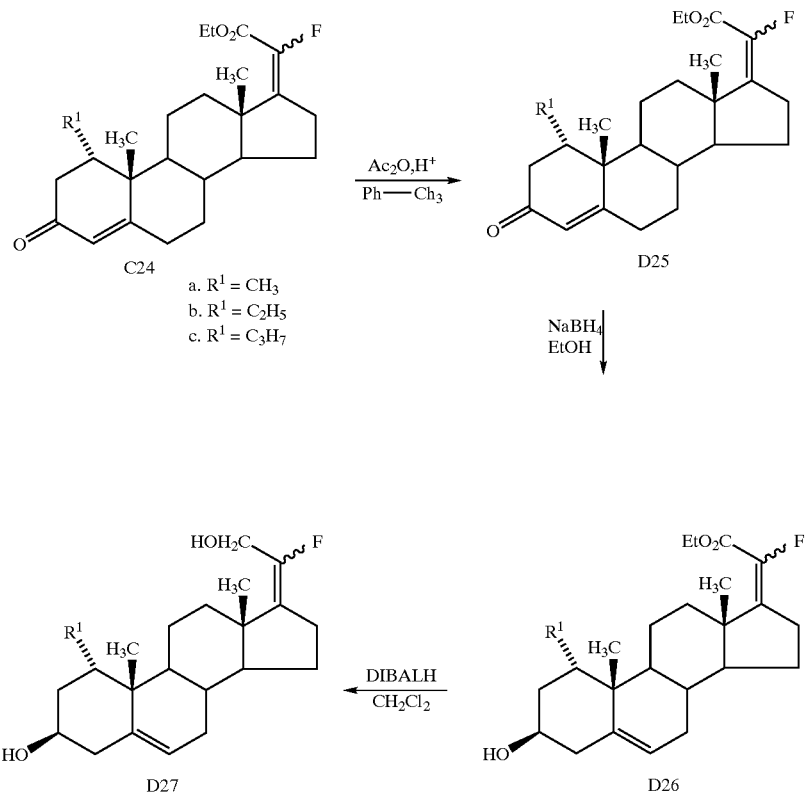

a. $R^1 = CH_3$
b. $R^1 = C_2H_5$
c. $R^1 = C_3H_7$

The C₁ substituted steroid-4-en-3-ones of this invention may be prepared as depicted in Scheme C. The starting 1α-alkylandrost-5-ene-3,17-diones (C19) are prepared from androsta-1,4-diene-3,17-dione (C18) according to Westermann and Nickisch (Westermann, J. and Nickisch, K., 1993, Angew. Chem. Int. Ed. Engl., 32, 1368–1370). The enone C19 is then protected as a dienol ether by treating C19 with trimethyl orthoformate in the presence of tosic acid. The resulting dienol ether C20 is reacted with the ylid formed by reaction of triethyl 2-fluoro-2-phosphonoacetate with base to give the vinyl fluoride C21. Diisobutylaluminum hydride reduction of the ester group in C21, followed by acid catalyzed hydrolysis of the dienol ether gives the desired 21-hydroxy-20ξ-fluoro-1α-methylpregna-4,17(20)-dien-3-one (C23). Similar hydrolysis of the dienol ether C21 gives the corresponding 20ξ-fluoro-1α-methyl-pregna-4,17(20)-dien-3-on-21-oic acid ethyl ester (C24).

The C₁ substituted steroid-5-en-3-ols of this invention may be prepared as depicted in Scheme D. The starting material, 20ξ-fluoro-1α-methylpregna4,17(20)-dien-3-on-21-oic acid ethyl ester (C24a), is first converted to the 3,5-dienol acetate D25a using acetic anhydride in refluxing toluene with a strong acid such as perchloric or tosic acid as a catalyst. Reduction of the 3,5-dienol acetate moiety with sodium borohydride is known to give the corresponding 5-en-3-βol, which, in this case, affords compound D26a. Further reduction of D26a with diisobutylaluminum hydride gives 20ξ-fluoro-1α-methylpregna-5,17(20)-diene-3β,21-diol (D27a). Compounds D27b and D27c are prepared in similar manner.

The C₂ substituted steroid-4-en-3-ones of this invention may be prepared as depicted in Scheme E. The known 2α-methylandrost-4-ene-3,17-dione (E29a, Iriarte, J. and Ringold, H. J., 1958, Tetrahedron, 3, 28–36) and 2α-ethylandrost-4-ene-3,17-dione (E29b, prepared by the methods of Ringold, H. J. and Rosenkranz, G., 1956, J. Org. Chem., 21, 1333–1335, and Tsuda, K. and Nozoe, S., 1959, Chem. Pharm. Bull. (Tokyo), 7, 232–237 and 238–240), serve as starting materials. Enone E29 is first protected as a dienol ether by treating E29 with trimethyl orthoformate in the presence of tosic acid. The resulting dienol ether E30 is reacted with the ylid formed by reaction of triethyl 2-fluoro-2-phosphonoacetate with base to give the vinyl fluoride ester E31. Diisobutylaluminum hydride reduction of the ester group, followed by acid catalyzed hydrolysis of the dienol ether gives the desired 21-hydroxy-20ξ-fluoro-2α-alkylpregna-4,17(20)-dien-3-ones (E33a and E33b). Similar hydrolysis of the dienol ethers E31 gives the corresponding 20ξ-fluoro-2α-alkylpregna-4,17(20)-dien-3-on-21-oic acid ethyl esters E34a and E34b.

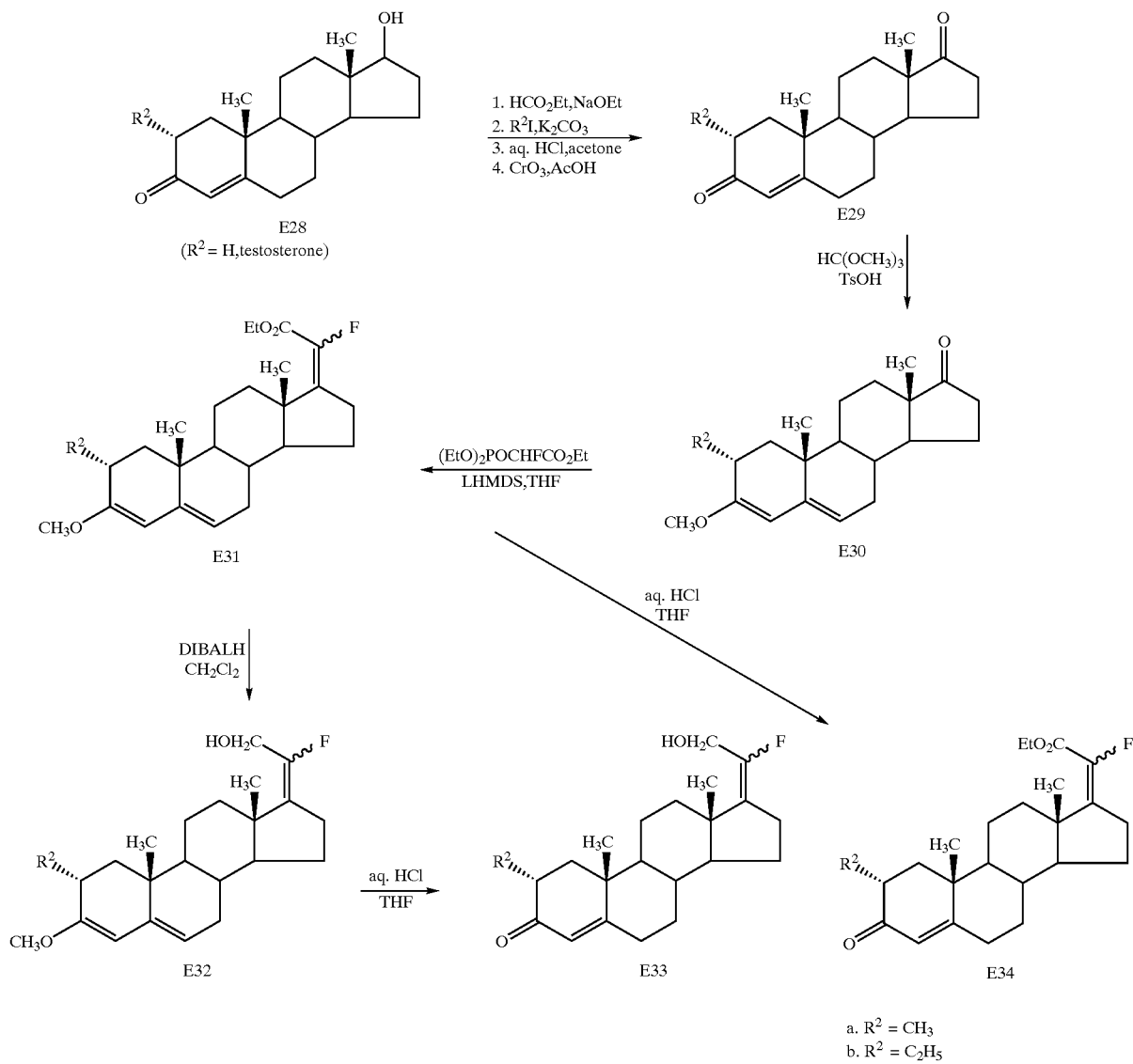

Scheme E
C₂ Substituted 4-en-3-ones a. R² = CH₃
b. R² = C₂H₅

The C₂ substituted steroid-5-en-3-ols of this invention may be prepared as depicted in Scheme F. The starting 20ξ-fluoro-2α-alkylpregna4,17(20)-dien-3-on-21-oic acid ethyl esters (E34a–c) are converted to the 3,5-dienol acetates F35 using acetic anhydride in refluxing toluene with a strong acid such as perchloric or tosic acid as a catalyst. Reduction of F35 with sodium borohydride gives the corresponding steroid-5-en-3-ols F36. Further reduction of F36 with diisobutylaluminum hydride and acid hydrolysis gives 20ξ-fluoro-2α-methyl-pregna- 5,17(20)-diene-3β,21-diol (F37a), 20ξ-fluoro-2α-ethylpregna-5,17(20)-diene-3β,21-diol (F37b), 20ξ-fluoro-2α-propylpregna-5,17(20)-diene-3β,21-diol (F37c).

The C₄ substituted steroid-4-en-3-ones of this invention may be prepared as depicted in Scheme G2. The starting point for the synthesis of each of these compounds is the appropriately substituted 4-alkytestosterone derivatives whose syntheses are detailed in Scheme G1. We found the most convenient route to these starting materials (G38) to be direct alkylation of testosterone (E28) by slow addition of alkyl iodide or alkyl bromide to a refluxing solution of testosterone and potassium t-butylate in t-butanol as described by Atwater (Atwater, N. W., *J. Am. Chem. Soc.*, 1960, 82, 2847–2852). These compounds are also prepared by addition of an appropriate Grignard reagent to enol lactone G40 followed by Robinson annelation (see Sondheimer, F. and Mazur, Y., 1957, J. Amer. Chem. Soc., 79, 2906–2910). By this latter process the branched alkyl substituted steroid 17β-hydroxy-4-(2-propyl)androst-4-en-3-one (G38c) is prepared. Jones oxidation of G38a–d provides 4-substituted steroid 4-en-3-ones G41a–d, respectively. 4-Chloroandrost-4-ene-3,17-dione (G41e) is prepared by reaction of androstenedione (G42) with sulfuryl chloride in pyridine as previously described (Kirk, D. N., Patel, D. K. and Petrow, V., *J. Chem. Soc.*, 1956, 1184–1186; Mori, H., *Chem. Pharm. Bull.*, 1962,10,429–432).

Transformation of the various 4-substituted steroid 4-en-3-ones G41a-e to vinyl fluorides G44a–e is shown in Scheme G2 and follows the general strategy previously developed. The steroid 4-en-3-one C41 is first protected as a dienol ether treating G41 with trimethyl orthoformate in the presence of tosic acid. The protected steroid G43 is then reacted with the ylid formed by reaction of triethyl 2-fluoro-2-phosphonoacetate with base to give the vinyl fluoride ester G44. Diisobutylaluminum hydride reduction of the ester group of G44, followed by acid catalyzed hydrolysis of the dienol ether gives the desired 21-hydroxy-20ξ,-fluoro4-substituted-pregna-4,17(20)-dien-3-ones (G46a–e). Similar acid hydrolysis of the dienol ether moiety of vinyl fluoride esters G44a–e gives the corresponding 20ξ-fluoro-4-substituted-pregna-4,17(20)-dien-3-on-21-oic acid ethyl esters (G47a–e).

The 4-nitro- and 4-aminosteroids (Scheme G3) are prepared using methodologies developed by Curran et al. (Curran, T. T., Flynn, G. A., Rudisill, D. E. and Weintraub, P. M., 1995, *Tetrahedron Lett.*, 36, 4761–4764). By way of example, 20ξ-fluoro-21-hydroxy-1α-methylpregna4,17(20)-dien-3-one (G48Aa) is reacted with t-butylate in t-butanol to form the thermodynamic enolate which then is reacted with i-propyl nitrate to give 20ξ-fluoro-21-hydroxy-1α-methyl-4-nitropregna-4,17(20)-dien-3-one (G49Aa). 20ξ-Fluoro-21-hydroxy-7α-methyl-4-nitropregna-4,17(20)-dien-3-one (G49Ab) and 20ξ-fluoro-21-hydroxy-15α-methyl-4-nitropregna-4,17(20)-dien-3-one (G49Ac) are prepared in an analogous manner. Chemoselective reduction of the nitro groups in G49Aa–c is accomplished by catalytic hydrogenation over Lindlar catalyst giving the corresponding amines: 4-amino-20ξ-fluoro-21-hydroxy-1α-methylpregna-4,17(20)-dien-3-one (G50Aa), 4-amino-20ξ-fluoro-21-hydroxy-7α-methylpregna-4,17(20)-dien-3-one (G50Ab) and 4-amino-20ξ-fluoro-21-hydroxy-15α-methylpregna-4,17(20)-dien-3-one (G50Ac), respectively. In the fashion just described, the 4-nitro-$C_{21}$-esters G49Ba–c are prepared and transformed into the 4-amino-$C_{21}$-esters G50Ba–c.

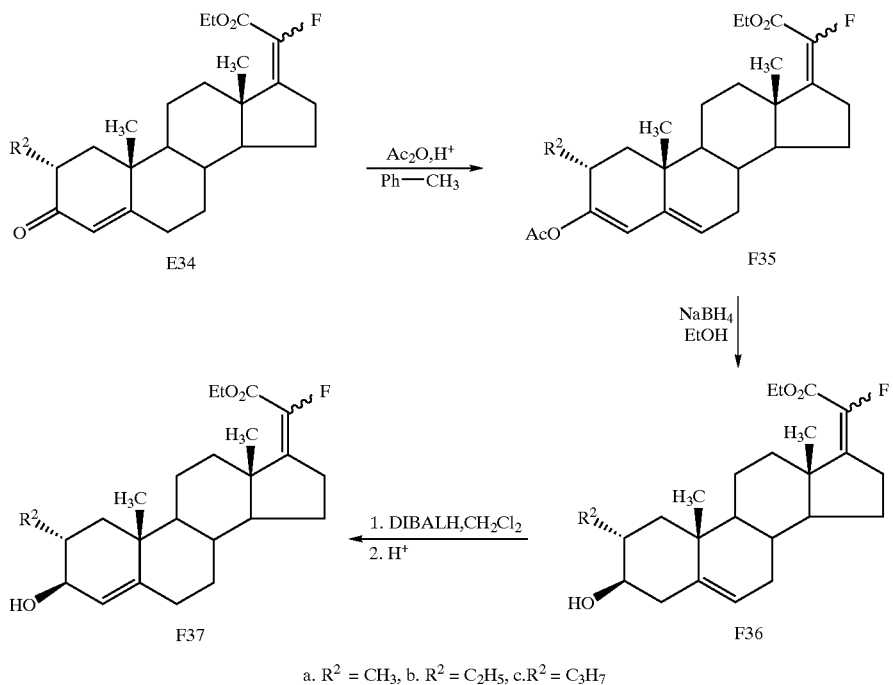

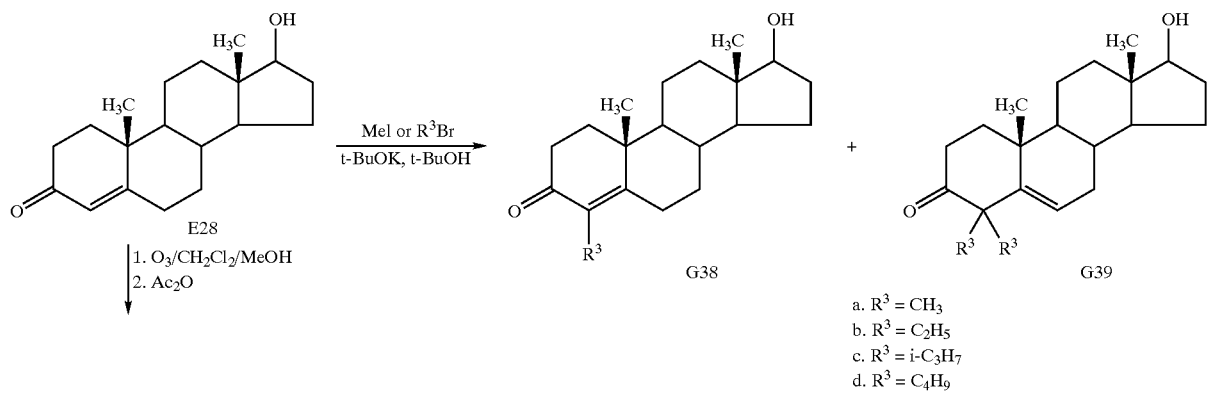

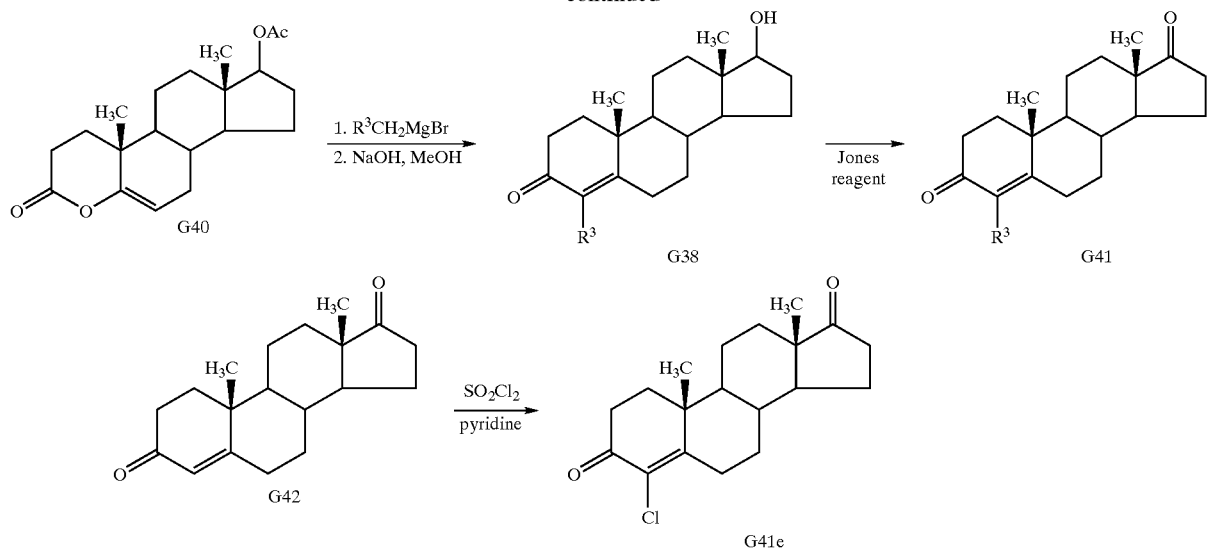

The C$_4$ substituted steroid-5-en-3-ols described in this invention may be prepared as depicted in Scheme H. Starting materials are the 4-alkyl- and 4-chloro-20ξ-fluoro-pregna-4,17(20)-dien-3-on-21-oic acid ethyl esters (G47a–e) described in Scheme G2. As in the previous examples, the steroid 4-en-3-ones G47 are first converted to the 3,5-dienol acetates H51 using acetic anhydride in refluxing toluene with a strong acid such as perchloric or tosic acid as a catalyst. Reduction of the 3,5-dienol acetates H51 to the corresponding 5-en-3-ols H52 is effected with sodium borohydride. Further reduction of H52 with diisobutylaluminum hydride gives the corresponding 20ξ-fluoro-4-substituted pregna-5,17(20)-diene-3β21-diols (H53a–e).

Scheme G2

C$_4$ Substituted Steroid-4-en-3-ones

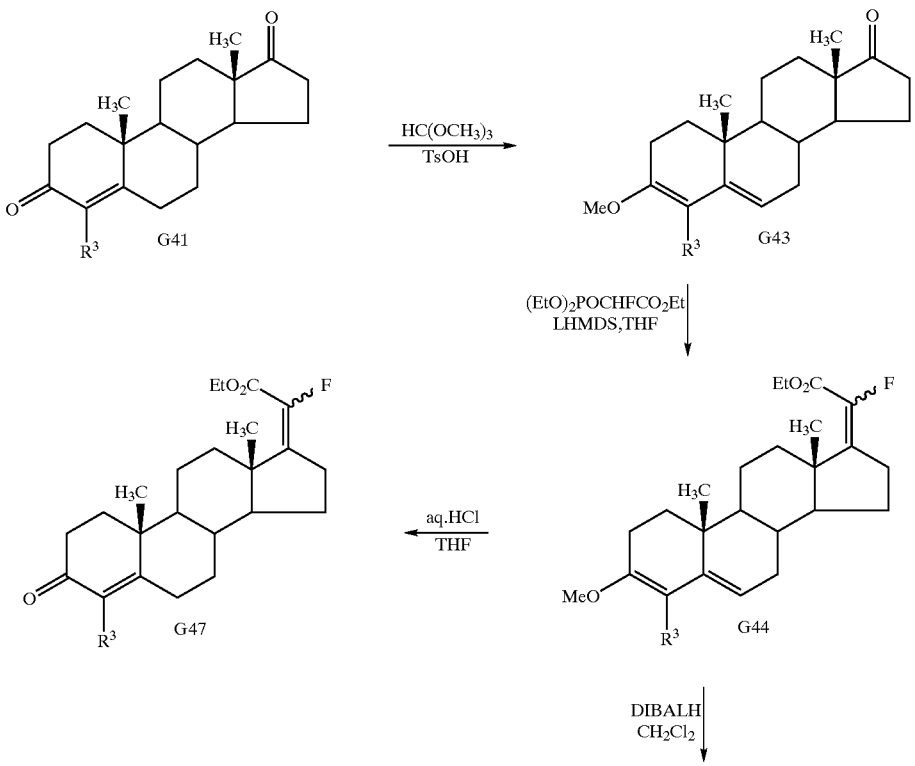

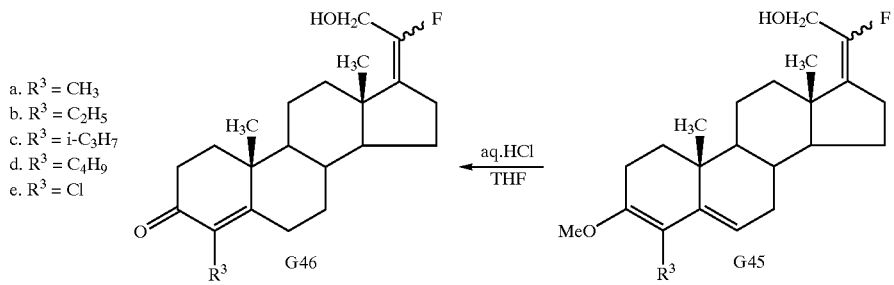

a. $R^3 = CH_3$
b. $R^3 = C_2H_5$
c. $R^3 = i-C_3H_7$
d. $R^3 = C_4H_9$
e. $R^3 = Cl$

The $C_6$-alkylandrost-4-ene-3,17-diones (I56a–c) which serve as starting materials for the $C_6$ substituted steroids of this invention are synthesized in five steps (the latter three steps are shown in Scheme I starting from I54) from androst-4-ene-3,17-dione using a method previously reported (Numazawa, M. and Oshibe, M. *J. Med. Clem.*, 1994, 37, 1312–1319). After the $C_3$ carbonyls of I56a–c are protected as dienol ethers I57a–c, a Wittig reaction is performed on the $C_{17}$ ketones with the ylid formed by reaction of triethyl 2-fluoro-2-phosphonoacetate with base to give the vinyl fluoride esters I58a–c as mixtures of E- and Z-isomers. Diisobutylaluminum hydride reduction of the ester group of I58a–c followed by mild acid hydrolysis of the dienol ether protecting group of I59a–c affords the 20ξ-fluoro-6-substituted-pregna-4,17(20)-dien-21-ol-3-ones I60a–c. Acid catalyzed unmasking of the $C_3$ carbonyl of I58a–c gives the corresponding 20ξ-fluoro-6-substituted-pregna-4,17(20)-dien-3-on-21-oic acid ethyl esters (I61a–c).

Scheme G3

$C_4$-Nitro and $C_4$-Amino Steroids

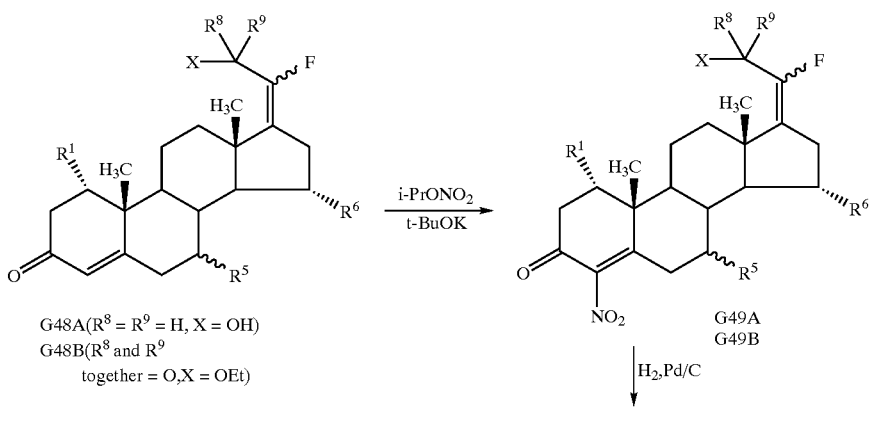

a. $R^1 = CH_3, R^5 = R^6 = H$
b. $R^5 = CH_3, R^1 = R^6 = H$
c. $R^6 = CH_3, R^1 = R^5 = H$

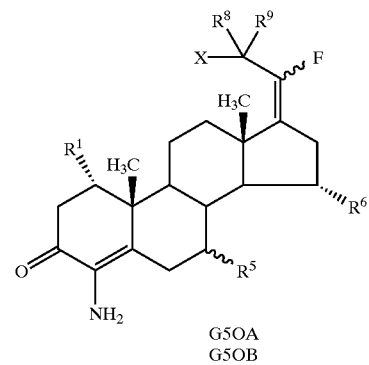

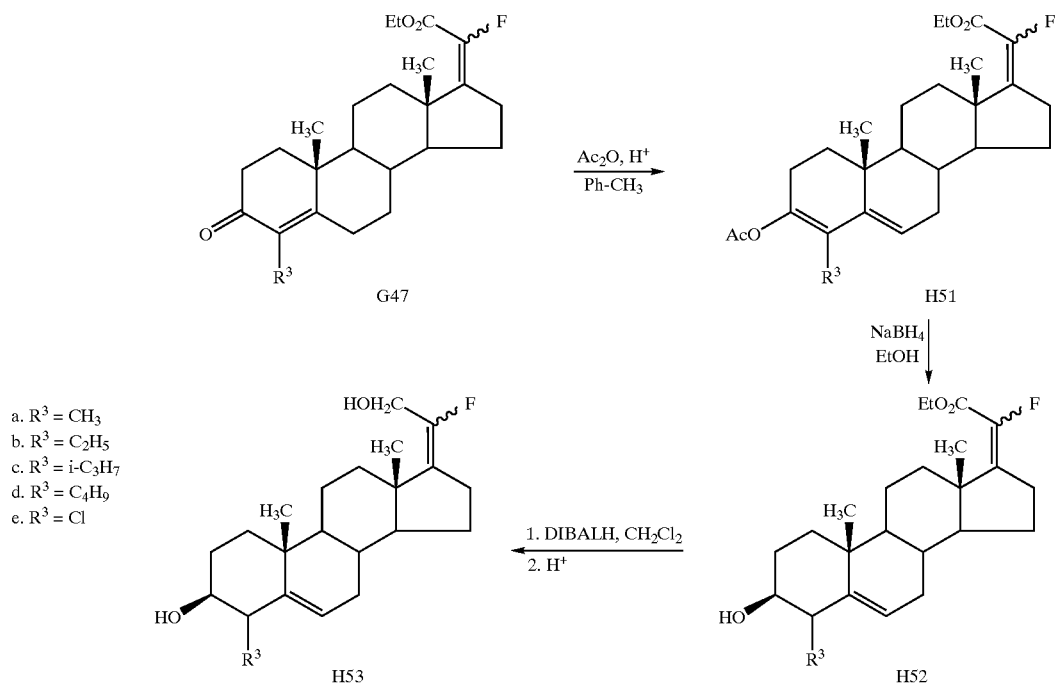
a. $R^3 = CH_3$
b. $R^3 = C_2H_5$
c. $R^3 = i\text{-}C_3H_7$
d. $R^3 = C_4H_9$
e. $R^3 = Cl$
Scheme I
$C_6$ Substituted Steroid-4-en-3-ones
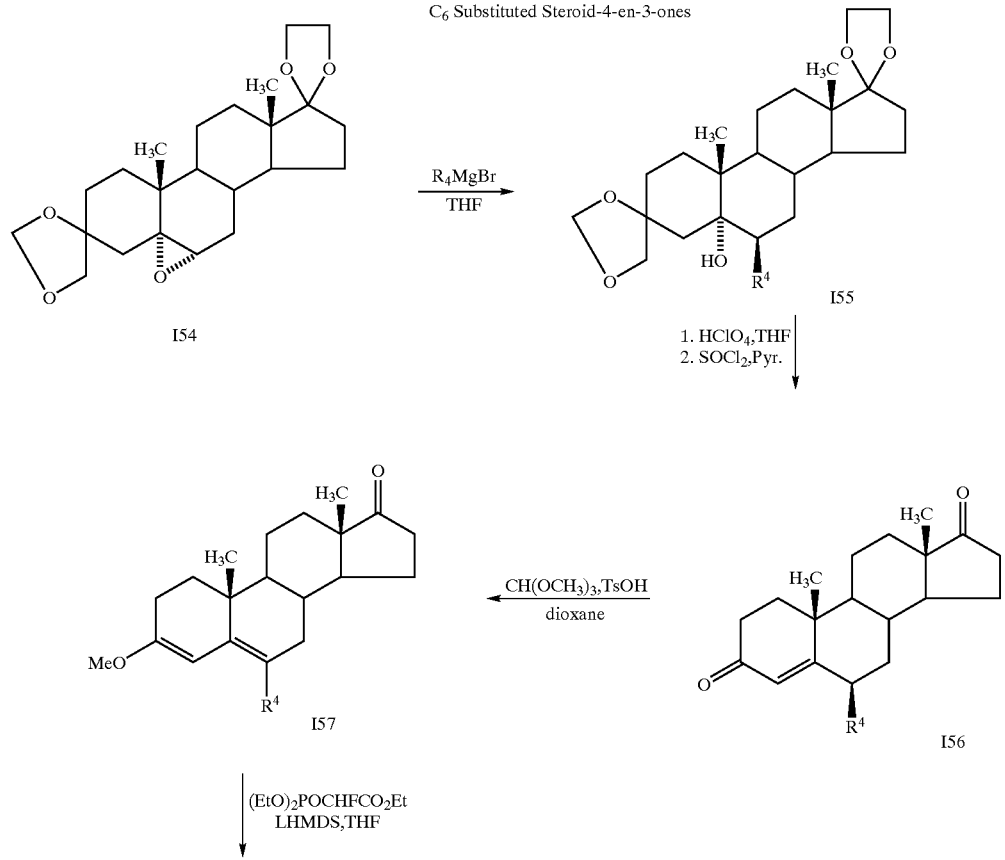

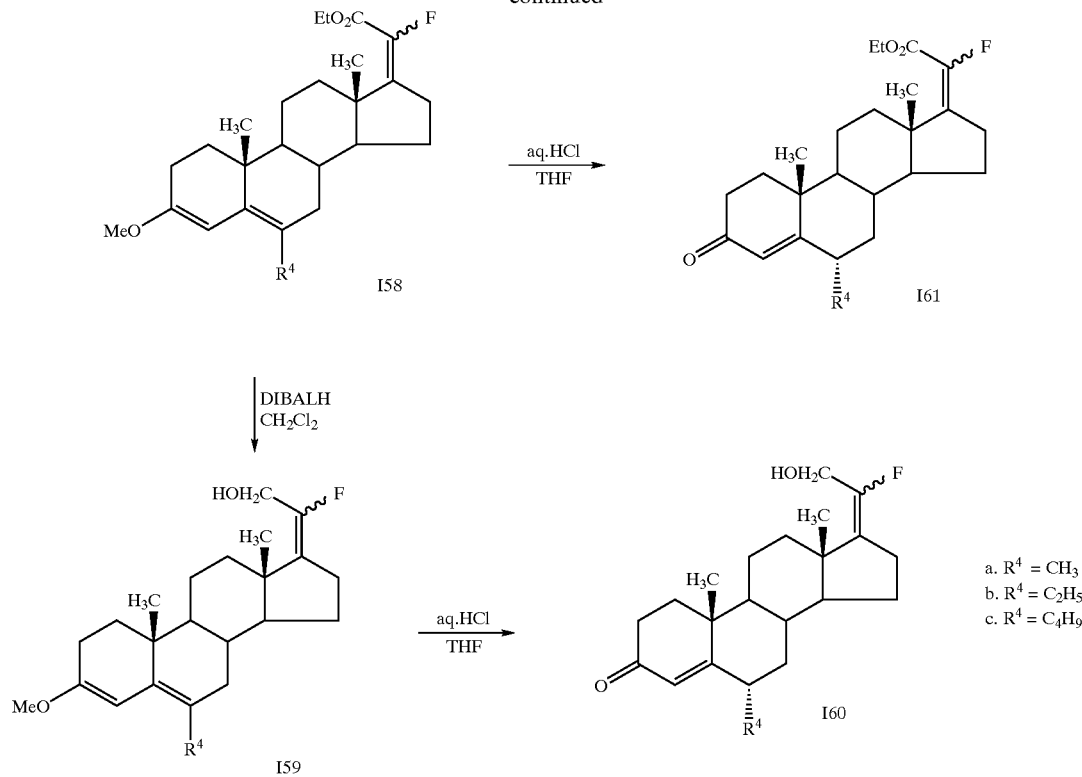
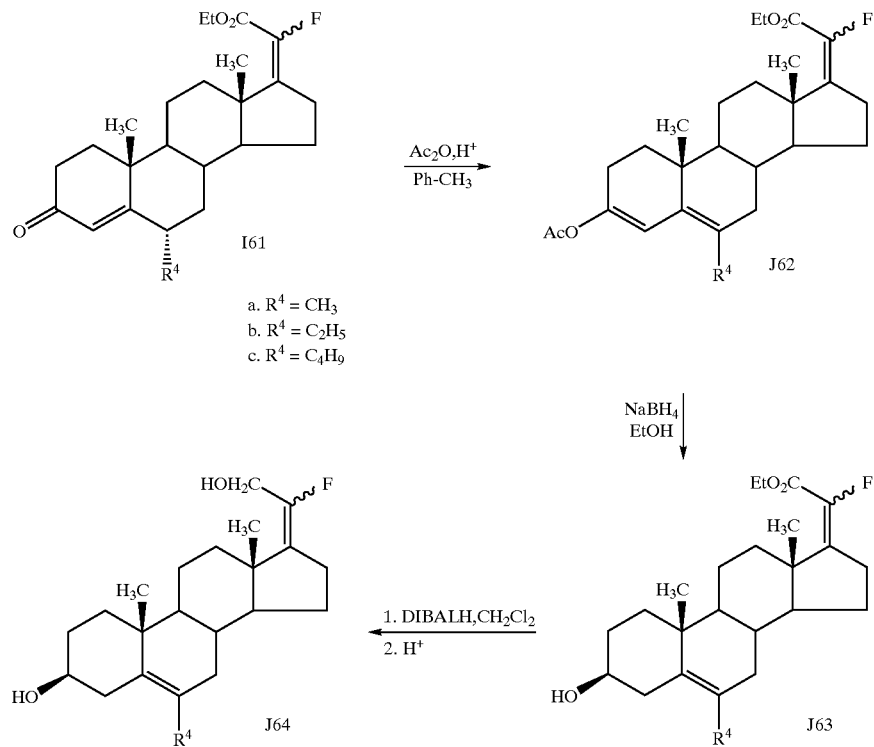
Scheme J
$C_6$ Substituted Steroid-5-en-3-ols

The C$_6$ substituted steroid-5-en-3-ols described in this invention may be prepared as depicted in Scheme J. Starting materials are the 20ξ-fluoro-6-alkylpregna-4,17(20)-dien-3-on-21-oic acid ethyl esters (I61a–c) described in Scheme I. As in the previous examples, the steroid 4-en-3-ones (I61a–c) are first converted to the 3,5-dienol acetates J62a–c using acetic anhydride in refluxing toluene with a strong acid such as perchloric or tosic acid as a catalyst. Reduction of the 3,5-dienol acetates J62a–c to the corresponding 5-en-3-ols J63a–c is effected with sodium borohydride. After further reduction of J63a–c with diisobutylaluminum hydride there is obtained 20ξ-fluoro-6-substituted-pregna-5,17(20)-diene-3β,21-diols J64a–c.

6-Dehydrotestosterone (K65) is converted to known C$_7$-substituted steroids K66a–h (Grunwell, J. F., Benson, H. D., Johnston, J. O. and Petrow, V. *Steroids*, 1976, 27, 759–771), and oxidation of K66a–d and K66e–h with Jones reagent affords C$_{7\alpha}$-alkylandrost-4-ene-3,17-diones (K67a–d) and C$_{7\beta}$-alkylandrost-4-ene-3,17-diones (K67e–h), respectively. The C$_3$ carbonyls are protected as dienol ethers K68a–h (see Scheme K). Wittig reaction on the C$_{17}$ ketones of dienol ethers K68a–h with the ylid formed by reaction of triethyl 2-fluoro-2-phosphonoacetate with base gives the vinyl fluoride esters K69a–h as mixtures of E- and Z-isomers. Reduction of the dienol esters K69a–h with diisobutylaluminum hydride and acidic removal of the C$_3$ protecting group gives 20ξ-fluoro-7-substituted-pregna-4,17(20)-dien-21-ol-3-ones K71a–h. Finally, acid catalyzed unmasking of the C$_3$ carbonyl of K69a–h gives the desired 20ξ-fluoro-7-substituted-pregna-4,17(20)-dien-3-on-21-oic acid ethyl esters K72a–h.

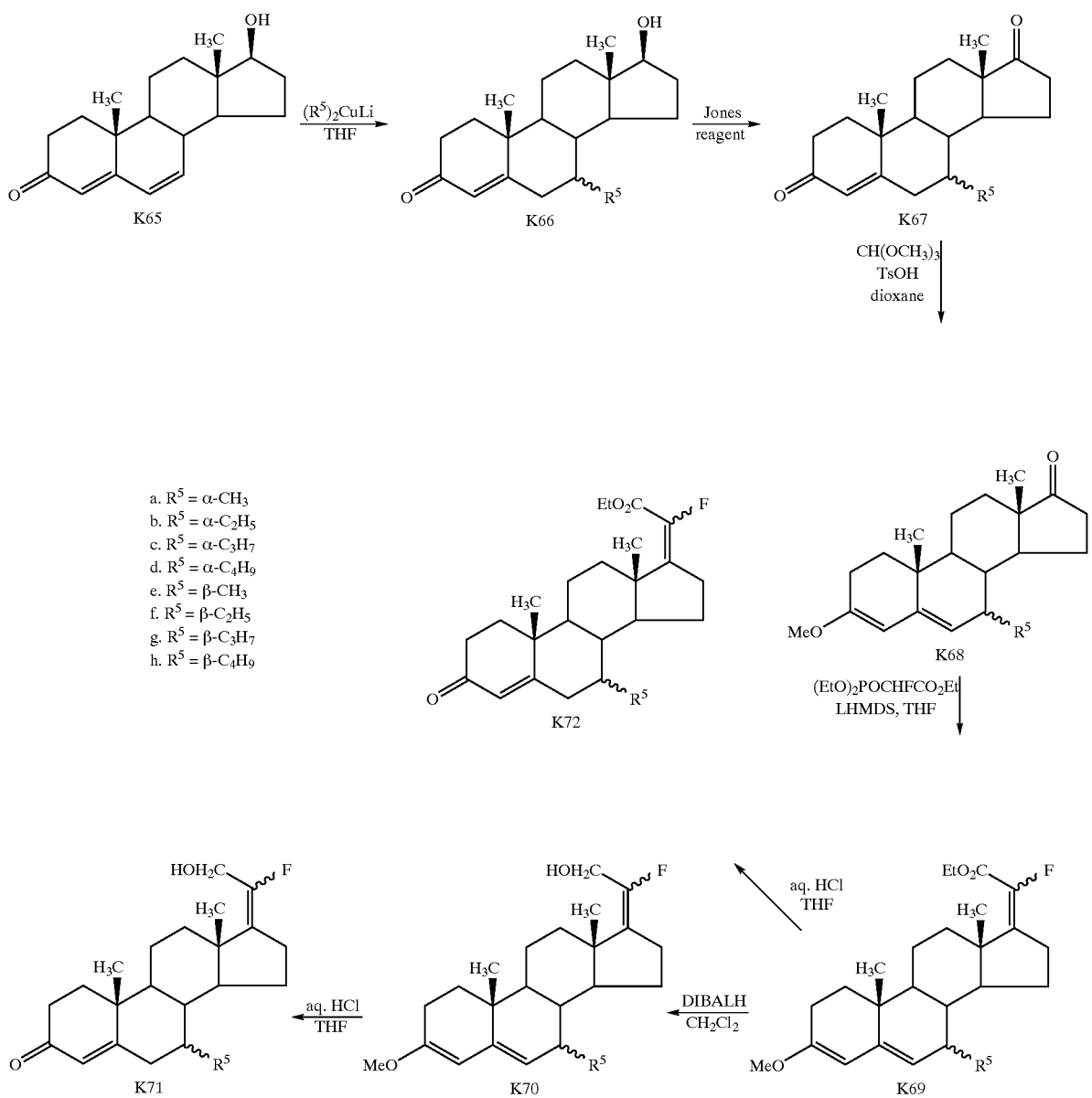

Scheme K
C$_7$ Substituted Steroid-4-en-3-ones a. R$^5$ = α-CH$_3$
b. R$^5$ = α-C$_2$H$_5$
c. R$^5$ = α-C$_3$H$_7$
d. R$^5$ = α-C$_4$H$_9$
e. R$^5$ = β-CH$_3$
f. R$^5$ = β-C$_2$H$_5$
g. R$^5$ = β-C$_3$H$_7$
h. R$^5$ = β-C$_4$H$_9$ Scheme L outlines the syntheses of $C_7$ substituted steroid-5-en-3-ols. The selectively $C_3$ protected $C_7\alpha$-alkylandrost-5-en-3,17-diols (L76a–d) and $C_7\beta$-alkylandrost-5-en-3,17-diols (L76e–h) are synthesized from the known $C_7$ substituted steroids L74a–h (Grunwell, J. F., Benson, H. D., Johnston, J. O. and Petrow, V. *Steroids*, 1976, 27, 759–771) by borohydride reduction of L74a–h to give L75a–h. Protection of the $C_3$ hydroxyl group as the t-butyldimethylsilyl ether with t-butyldimethylsilyl chloride in dimethylformamide and removal of the acetate moiety by saponification with lithium hydroxide in aqueous methanol/tetrahydrofuran gives 3β-[[(1,1-dimethylethyl)-dimethylsilyl]oxy]-7-substituted-androst-5-en-17β-ols (L76a–h). Oxidation of $C_{17}$ alcohols L76a–h with Jones reagent gives the corresponding ketones L77a–h. The latter undergo Wittig reaction at the $C_{17}$ ketone with the ylid formed by reaction of triethyl 2-fluoro-2-phosphonoacetate with base to afford the vinyl fluoride esters L78a–h as mixtures of E- and Z-isomers. Reduction of the ester groups with diisobutylaluminum hydride and tetrabutylammonium fluoride catalyzed removal of the $C_3$ silyl group gives the 20ξ-fluoro-7-substituted-pregna-5,17(20)-diene-3β,21-diols L80a–h.

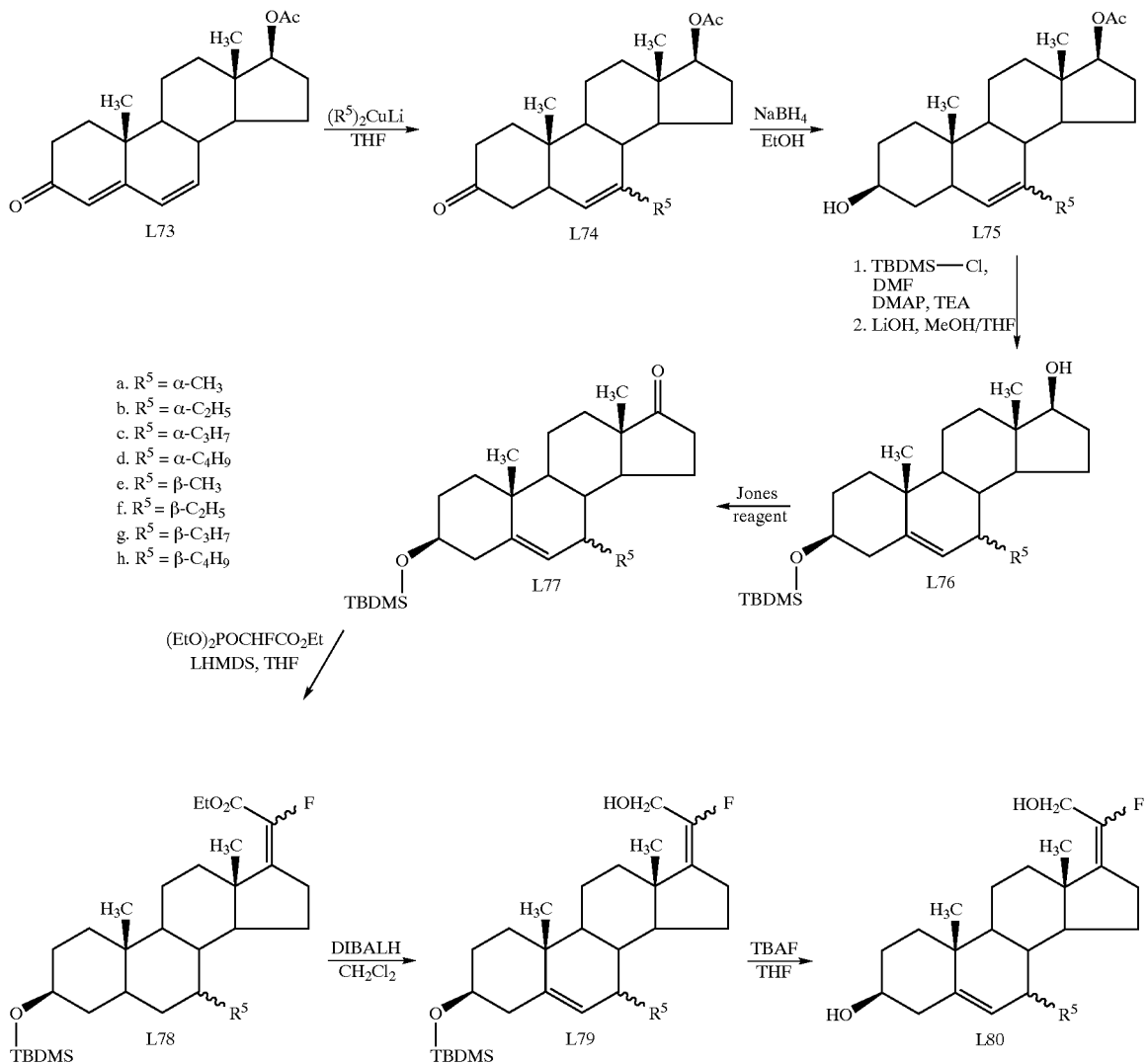

3β-Hydroxyandrosta-5,15-dien-17-one (Scheme M, M81) is prepared by the method of Reeder and Joannou (Reeder, A. Y. and Joannou, G. E., *Steroids*, 1996, 61, 74–81) and used as starting material for the preparation steroids containing an additional double bond at $C_{15}$ as shown in Scheme M. Alcohol M81 is first silylated by reaction with t-butyldimethylsilyl chloride to give silyl ether M82. Wittig reaction on the $C_{17}$ ketone with the ylid formed by reaction of triethyl 2-fluoro-2-phosphonoacetate with base gives vinyl fluoride ester M83 as a mixture of E- and Z-isomers. Reduction of ester M83 with diisobutylaluminum hydride in dichloromethane gives a mixture of alcohols which are separated by flash chromatography into the individual E- and Z-isomers M85 and M84, respectively. Removal of the silyl protecting group of Z-olefin M84 with tetrabutylammonium fluoride gives diol M86. Similar removal of the silyl protecting group of E-olefin M85 gives diol M87.

Scheme M
C$_{15}$ Unsaturated Steroid-5-en-3-ols

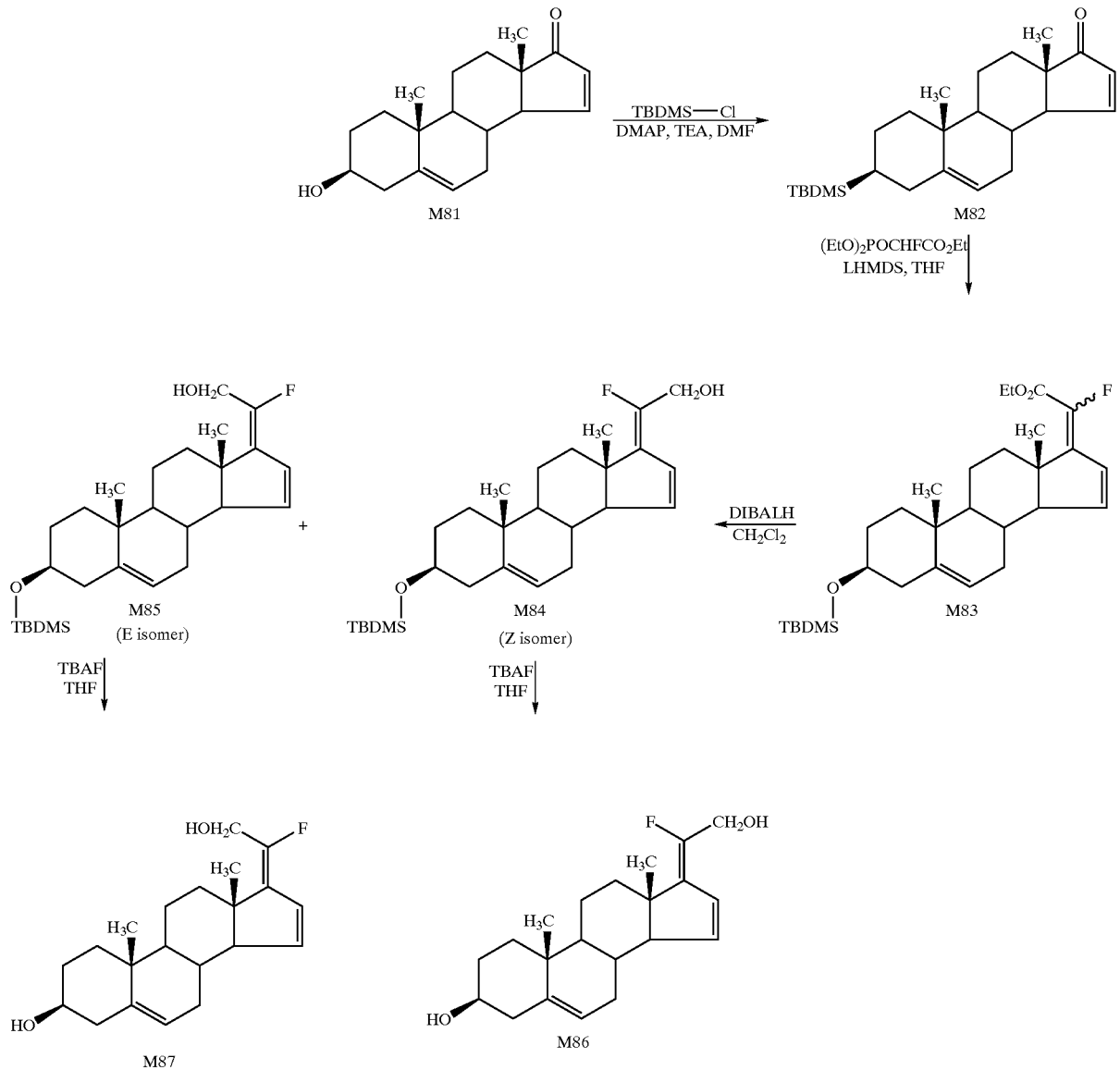

The C$_{15}$-alkyl-androst-5-en-17-ones (Scheme N, N88a–c), which serve as starting materials for the C$_{15}$ substituted steroids of this invention, are synthesized in two steps from 3β-hydroxyandrost-5,15-dien-17-ones M81 as shown in Scheme N. Wittig reaction on C$_{17}$ ketones N88a–c with the ylid formed by reaction of triethyl 2-fluoro-2-phosphonoacetate with base gives vinyl fluoride esters N89a–c as mixtures of E- and Z-isomers. Diisobutyl aluminum hydride reduction of the ester group of N89a–c gives alcohols N90a–c that on subsequent tetrabutylammonium fluoride catalyzed removal of the silyl protecting groups affords the 20ξ-fluoro-15-substituted-pregna-5,17(20)-diene-3β,21-diols N91a–c.

Silyl protected 19-nordehydroepiandrosterone (Scheme O, O97) is prepared in five steps from the known 19-nortestosterone (O92) by modification of the method of Campbell and Babcock (Campbell, J. A. and Babcock, J. C., 1971, U.S. Pat. No. 3,597,418) wherein the C$_3$ hydroxyl group is protected with a t-butyldimethylsilyl group rather than a tetrahydropyranyl group. Thus, alcohol O94 is prepared as described in U.S. Pat. No. 3,597,418 and is treated with t-butyldimethylsilyl chloride as previously described herein to give silyl ether O95. The C$_{17}$ acetate is hydrolyzed with potassium carbonate in aqueous methanol, and resulting alcohol O96 is oxidized with pyridinium chromate to C$_{17}$ ketone O97. Introduction of the vinyl fluoride via Wittig reaction as previously described herein affords vinyl fluoride ester O98. Reduction of O98 with diisobutylaluminum hydride and fluoride catalyzed removal of the silyl protecting group of O99 provides the desired diol O100 as a mixture of E and Z isomers.

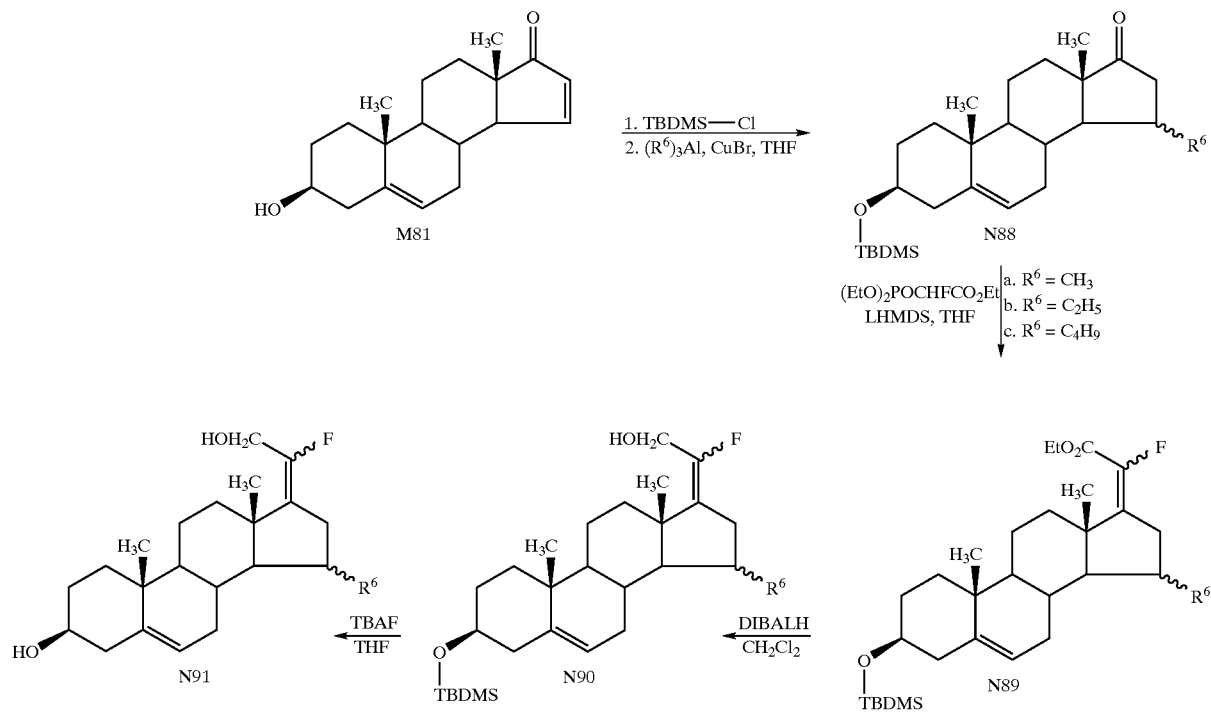
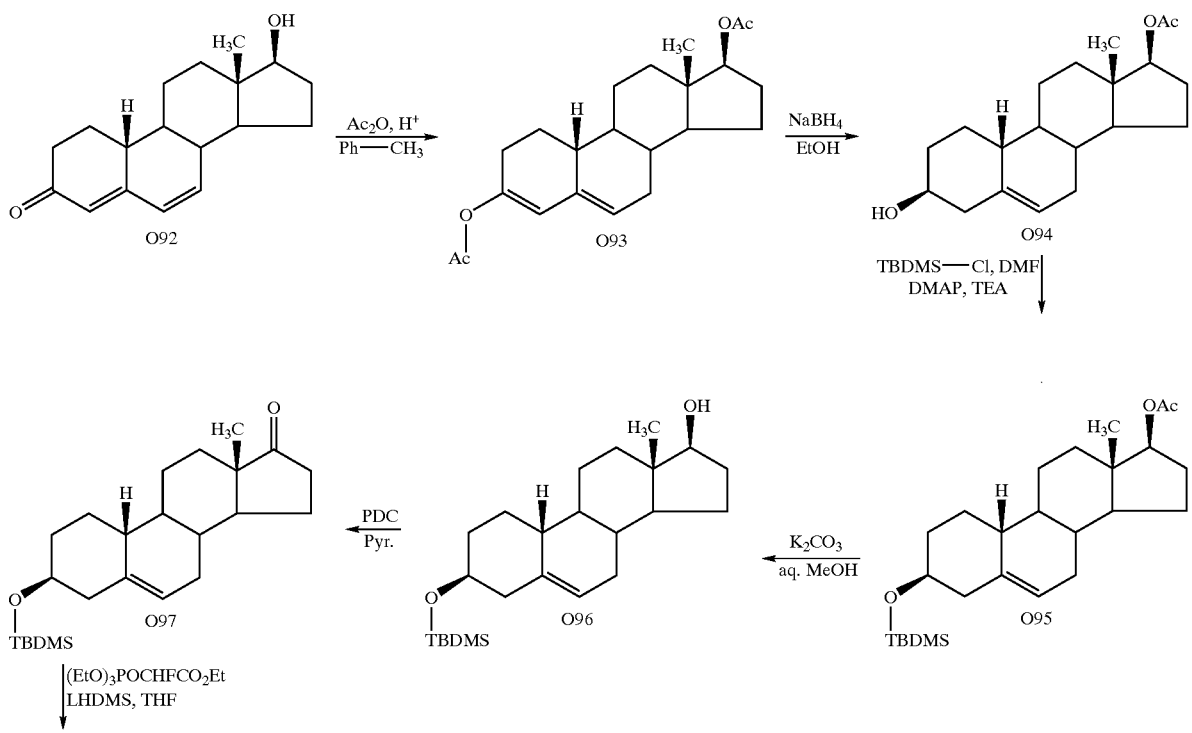

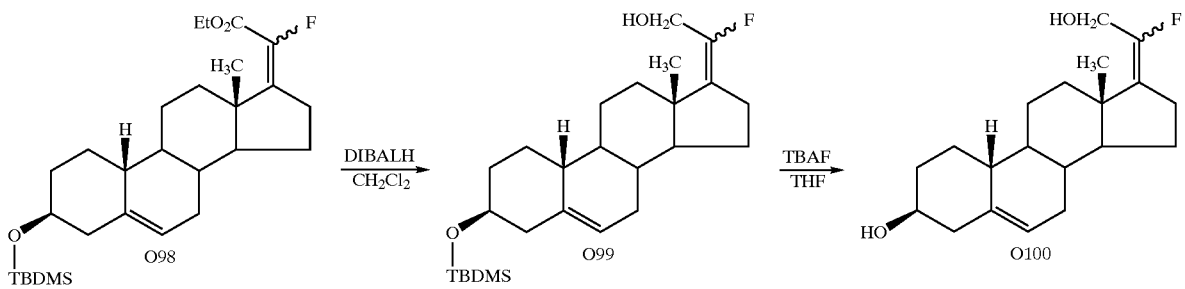

EXPERIMENTAL

General Experimental Conditions

Melting points were determined with a Thomas-Hoover capillary melting point apparatus and are uncorrected. TLC analyses were performed with Merck DC-F254 or Analtech GHLF silica gel plates, with visualization by alkaline permanganate and UV irradiation. Flash chromatography was performed with Merck silica gel 60 (0.040–0.063 mm). NMR spectra were recorded on Varian VXR-300, Unity 300, Unity 400 or Gemini-300 spectrometers in $CDCl_3$, unless otherwise stated. $^1H$ and $^{13}C$ NMR signals are reported in ppm from tetramethylsilane, $^{19}F$ NMR signals are reported in ppm from $CFCl_3$ and coupling constants are reported in Hertz (Hz). IR spectra were recorded on a Perkin-Elmer Model 1800 or Mattson Galaxy 5020 FT-IR spectrophotometer. MS data were collected at 70 eV on a Finnigan MAT 4600, Mat TSQ-700 or VG Analytical Limited ZAB2-SE mass spectrophotometer and computerized peak matching with perfluorokerosene as the reference is utilized for HRMS. Combustion analysis was performed using a Perkin-Elmer Model 2400 elemental analyzer and the results were within ±0.4% of the calculated values. Organic extracts were dried over anhydrous $MgSO_4$ or $Na_2SO_4$ prior to solvent removal on a rotary evaporator. Celite® (diatomaceous earth) (Celite Corporation, 137 West Central Avenue, Lompor, Calif. 93436) was used as a filtering, aid unless otherwise indicated.

EXAMPLE 1a

3β-[[(1,1-Dimethylethyl)dimethylsilyl]oxy]androst-5-en-17-one (A2)

Add t-butyldimethylsilyl chloride (10.97 g, 72.8 mmol), 4-dimethylaminopyridine (0.42 g, 3.47 mmol) and triethylamine (10.63 mL, 76.27 mmol) to a stirred solution of dehydroepiandrosterone (A1, 20.00 g, 69.3 mmol) in anhydrous DMF (350 mL) under nitrogen. Stir the resultant suspension at room temperature for 3 days and then pour into rapidly stirred water (1.5 L). Filter the resultant suspension and recrystallize the white solid from aqueous acetone to give A2 (24.64 g, 88%) as a white crystalline solid: mp 146–148° C. TLC $R_f$ 0.78, ethyl acetate/hexane (1:1); $^1H$ NMR δ 5.38–5.32 (m, 1H), 3.55–3.43 (m, 1H), 1.03 (s, 3H), 0.89 (s, 9H), 0.88(s, 3H), 0.06 (s, 6H); MS (CI, $CH_4$) m/z (rel intensity) 403 ($MH^+$, 3), 401 (5), 387 (9), 345 (18), 271 (100). Analysis Calculated for $C_{25}H_{42}SiO_2$: C, 74.57; H, 10.51. Found: C, 74.89; H, 10.84.

EXAMPLE 1b

3β-[[(1,1-Dimethylethyl)dimethylsilyl]oxy]-20ξ-fluoropregna-5,17(20)-dien-21-oic Acid, Ethyl Ester (A3)

Add lithium hexamethyldisilazide (3.50 mL of a 1.0M solution in THF, 3.50 mmol) to a stirred solution of triethyl 2-fluoro-2-phosphonoacetate (0.76 mL, 3.75 mmol) in THF (15 mL) under nitrogen. After 1 hour, add a solution of A2 (1.01 g, 2.50 mmol) in THF (5 mL) and heat the reaction mixture to reflux. After 2.5 hours, allow the reaction mixture to cool to room temperature and concentrate. Partition the residue between diethyl ether (40 mL) and 0.4M aqueous hydrochloric acid (40 mL). Separate the layers and wash the organic layer with 0.5M aqueous hydrochloric acid (20 mL), saturated aqueous sodium bicarbonate (20 mL), and brine (20 mL). Dry the organic phase, filter, and concentrate to give crude A3. Purify the material by flash chromatography (6×7 cm column) and elute with ethyl acetate/ hexane (2:98) to give A3 (mixture of E and Z isomers, 0.83 g, 67%) as a white solid. TLC $R_f$ 0.41 and 0.51, ethyl acetate/hexane (3:97); $^{19}F$ NMR δ −121.59 (s, E isomer) and −135.49 (s, Z isomer); MS (CI, $CH_4$) m/z (rel intensity) 491 ($MH^+$, 97), 475 (59), 445 (24), 433 (65), 359 (100), 339 (24). Analysis. Calculated for $C_{29}H_{47}OF_3Si$: C, 70.97; H, 9.65. Found: C, 71.32; H, 10.02.

EXAMPLE 1c (17E)-3β-[[(1,1-Dimethylethyl)dimethylsilyl]oxy]-20-fluoropregna-5,17(20)-dien-21-ol (A4) and (17Z)-3β-[[(1,1-Dimethylethyl)dimethylsilyl]oxy]-20-fluoropregna-5,17(20)-dien-21-ol (A5)

Add diisobutylaluminum hydride (6.55 mL of a 1.0M solution in dichloromethane, 65.5 mmol) to a stirred solution of A3 (7.29 g, 14.86 mmol) in dichloromethane (135 mL) under nitrogen and cool slowly to −78° C. After 1 hour, quench the reaction with a solution of glacial acetic acid (3.8 mL) in dichloromethane (9 mL) and pour the reaction mixture into dichloromethane (250 mL)/saturated aqueous potassium sodium tartrate (250 mL). Filter the resultant emulsion through a Celite® pad (3 cm), transfer the filtrates to a separatory funnel, and separate the layers. Wash the organic layer with saturated aqueous potassium sodium tartrate (130 mL), saturated aqueous sodium bicarbonate (250 mL), and brine (100 mL). Dry, filter, and concentrate the organic phase to give the crude product. Purify by flash chromatography (2 equal batches, 8×20 cm column) and elute with a gradient (10 to 15%) of ethyl acetate in hexane to give A4 (3.80 g, 57%) as a white solid: mp 144–147° C. TLC $R_f$ 0.37, ethyl acetate/hexane (15:85); $^1H$ NMR (400 MHz) δ 5.34–5.29 (m, 1H), 4.29 (ddd, 1H, J=21.4, 13.4, 6.4 Hz), 4.20 (ddd, 1H, J=21.4, 13.4, 6.4 Hz), 3.53–3.44 (m, 1H), 1.01 (s, 3H), 0.91 (d, 3H, J=1.1 Hz), 0.89 (s, 9H), 0.054 (s, 6H); $^{19}F$ NMR δ −114.32 (br t, J=24 Hz); MS (CI, $CH_4$) m/z (rel intensity) 449 ($MH^+$, 3), 448 (5), 447 (19), 431(10), 429 (5), 391 (32), 299 (100), 297 (17). Analysis. Calculated for $C_{27}H_{45}OF_2Si$: C, 72.27; H, 10.11. Found: C, 72.18; H, 10.28.

Also, isolate A5 (1.10 g, 16%) as a white solid: mp 174–176° C. TLC $R_f$ 0.29, ethyl acetate/hexane (15:85); $^1H$ NMR δ 5.36–5.31 (m, 1H), 4.15 (dd, 2H, J=21.2, 6.1 Hz), 3.56–3.44 (m, 1H), 1.03 (s, 3H), 0.94 (s, 3H), 0.91 (s, 9H), 0.075 (s, 6H); $^{19}$F NMR δ −128.10 (t, J=21.1 Hz); MS (CI, $CH_4$) m/z (rel intensity) 449 ($MH^+$, 2), 448 (4), 447 (15), 431 (10), 429 (5), 391 (26), 317 (47), 299 (100) 297 (15); Analysis. Calculated for $C_{27}H_{45}OF_2Si$: C, 72.27; H, 10.11. Found: C, 72.06; H, 10.22.

EXAMPLE 1d (17E)- 20-Fluoropregna-5,17(20)-diene-3β,21-diol (A6)

Add tetrabutylammonium fluoride (3.0 mL of a 1.0M solution in THF, 3.0 mmol) to compound A4 (307 mg, 0.68 mmol), under nitrogen, and stir the resultant solution at room temperature for 23 hours. Add the reaction solution dropwise to vigorously stirred water (50 mL), filter the resultant suspension and dry the filter cake to give A6 (218 mg, 95%) as a white solid: mp=214–216° C. TLC $R_f$ 0.15, ethyl acetate/hexane (45:55); $^1$H NMR (DMSO-$d_6$) δ 5.30–5.25 (m, 1H), 4.92 (t, 1H, J=5.5 Hz), 4.60 (d, 1H, J=4.8 Hz), 4.15–3.89 (m, 2H), 3.35–3.19 (m), 0.95 (s, 3H), 0.85 (d, 3H, J=1.1 Hz); $^{19}$F NMR (DMSO-$d_6$) δ −108.66 (dd, J=28.0, 24.1 Hz), MS (CI, $CH_4$) m/z (rel intensity) 335 ($MH^+$, 4), 334 (9), 333 (18), 317 (100), 299 (93), 297 (28). Analysis. Calculated for $C_{21}H_{31}OF_2$: C, 75.41; H, 9.34. Found: C, 75.61; H, 9.50.

EXAMPLE 1e (17E)-3β-[[(1,1-Dimethylethyl)dimethylsilyl]oxy]-20-fluoropregna-5,17(20)-diene (A7)

Add sulfur trioxide pyridine complex (0.84 g, 5.27 mmol) to a stirred solution of A4 (1.35 g, 3.00 mmol) in THF (30 mL), under nitrogen with cooling in an ice water bath. Stir the resultant suspension at ice bath temperature for 3 hours, and then store in a refrigerator overnight. Carefully add lithium aluminum hydride (0.80 g, 21.08 mmol) in portions to the stirred suspension. Quench the reaction by cautiously adding 0.6 mL of water, 0.6 mL of 1.0N aqueous sodium hydroxide and, finally, another 0.6 mL of water. Dilute the resultant suspension with diethyl ether (80 mL) and stir vigorously for several minutes. Filter the suspension and concentrate the filtrate to give crude A7. Purify by flash chromatography (5×14 cm column) and elute with ethyl acetate/hexane (5:95) to give A7 (0.99 g, 76%) as a white solid. Recrystallize a portion of A7 from aqueous acetone to give a white crystalline solid: mp 128–130° C. TLC $R_f$ 0.52, ethyl acetate/hexane (2:98); $^1$H NMR δ 5.35–5.31 (m, 1H), 3.55–3.42 (m, 1H), 1.92 (dt, 3H, J=18.9, 1.9 Hz) 1.01 (s, 3H) 0.89 (s, 9H), 0.86 (d, 3H, J=1.3 Hz), 0.06 (s, 6H); $^{19}$F NMR δ −95.86 (q, J=18.9 Hz); MS (CI,$CH_4$) m/s (rel intensity) 433 ($MH^+$, 9), 432 (10), 431 (38), 417 (43) 413 (70), 375 (55), 301 (100). Analysis. Calculated for $C_{27}H_{45}FOSi$: C, 74.94; H, 10.48. Found: C, 75.16; H, 10.46.

EXAMPLE 1f (17E)- 20-fluoropregna-5,17(20)-dien-3β-ol (A8)

Prepare A8 from A7 in a manner analogous to the preparation of A6 from A4 to give A8 (299 mg, 94%) as a white solid: mp 129–133° C. TLC $R_f$ 0.25, ethyl acetate/hexane (1:3); $^1$H NMR δ 5.38–5.34 (m, 1H), 3.60–3.47 (m, 1H), 1.92 (dt, 3H, J=18.9, 1.9 Hz), 1.02 (s, 3He), 0.86 (d, 3H, J=1.2 Hz); $^{19}$F NMR δ −95.79 (q, J=18.8 Hz); MS (CI, $CH_4$) m/z ( rel intensity) 319 ($MH^+$, 9), 318 (17), 317 (33), 301 (100), 299 (65), 281 (9). Analysis. Calculated for $C_{21}H_{31}OF$: C, 79.20; H, 9.81. Found: C, 79.10, H, 9.81.

EXAMPLE 1g (17Z)- 20-Fluoropregna-5,17(20)-diene-3β,21-diol (A9)

Prepare A9 from A5 in a manner analogous to the preparation of A6 from A4 to give A9 (299 mg, 94%) as a white solid: mp 198–203° C. TLC $R_f$ 0.19, ethyl acetate (45:55); $^1$H NMR δ 5.29–5.25 (m, 1H), 4.91 (t, 1H, J=5.7 Hz), 4.60 (d, 1H, J=4.5 Hz), 3.88 (dd, 1H, J=23.1, 5.7 Hz), 3.34–3.19 (m, 1H), 0.95 (s, 3H), 0.86 (s, 3H); $^{19}$F NMR δ −123.18 (t, J=23.1 Hz); MS (CI, $CH_4$) m/z (rel intensity) 335 ($MH^+$, 4), 334 (6), 333 (15) 317 (100) 299 (46). Analysis. Calculated for $C_{21}H_{31}OF_2$: C, 75.41; H, 9.34. Found: C, 75.37; H, 9.43.

EXAMPLE 1h (17Z)-3-[[(1,1-Dimethylethyl)dimethylsilyl]oxy]-20-fluoropregna-5,17(20)-dien-3β-ol (A10)

Prepare A10 (0.59 g, 91%) from A5 in a manner analogous to the preparation of A7 from A4. Crystallization from acetone gives A10 as a white crystalline solid: mp 138–140° C. TLC $R_f$ 0.52, ethyl acetate/hexane (2:98); $^1$H NMR δ 5.34–5.30 (m 1H), 3.54–3.42 (m, 1H), 1.79 (dt, 3H, J=17.2, 1.4 Hz), 101 (s, 3H), 0.89 (s, 12H), 0.057 (s); $^{19}$F NMR δ −110.32 (q of q, J=17.1, 2.0 Hz); MS (CI, $CH_4$) m/z (rel intensity) 433 ($MH^+$, 10), 432 (12), 431 (45), 417 (58), 413 (45), 375 (58), 301 (100). Analysis. Calculated for $C_{27}H_{45}FOSi$: C, 74.94; H, 10.48. Found: C, 75.20; H, 10.43.

EXAMPLE 1i (17Z)-20-Fluoropregna-5,17(20)-dien-3β-ol (A11)

Prepare A11 from A10 in a manner analogous to the preparation of A8 from A7 to give A11 (204 mg, 64%) as a white crystalline solid, after crystallization from methanol: mp 153–155° C. TLC $R_f$ 0.27, ethyl acetate/hexane (1:3); $^1$H NMR δ 5.37–5.33 (m, 1H), 3.59–3.46 (m, 1H), 3.49 (s, 0.6H, MeOH solvate), 179 (dt, 3H, J=17.2, 1.4 Hz, 21-Me), 1.02 (s, 3H, 19-Me), 0.89 (s, 3H,); $^{19}$F NMR δ −110.27 (q of q, J=17.2, 2.0 Hz); MS (CI, $CH_4$) m/z (rel intensity) 319 ($MH^+$, 7), 318 (15), 317 (28), 301 (100), 299 (39), 281 (8). Analysis. Calculated for $C_{21}H_{31}OF$. 0.2 MeOH: C, 78.38; H, 9.87. Found: C, 78.40; H, 9.82.

EXAMPLE 2a

20ξ-Fluoro-3β-hydroxypregna-5,17(20)-dien-21-oic Acid, Ethyl Ester (B12)

Add tetrabutylammonium fluoride (45.0 mL of a 1.0M solution in THF, 45.0 mmol) to compound A3 (7.3 g, 14.87 mmol) and stir the resultant solution at room temperature for 30 hours. Slowly add the reaction solution to vigorously stirred cold water (750 mL), filter the resultant suspension and dry to give crude B12. Purify B12 by flash chromatography.

EXAMPLE 2b

20ξ-Fluoropregna4,17(20)-dien-3-on-21-oic Acid, Ethyl Ester (B13)

Dissolve alcohol B12 (7.14 g, 18.96 mmol) in benzene (200 mL) and add 3 Å molecular sieves (1 g). Add pyridinium chlorochromate (81.7 g, 0.379 mol) and reflux the mixture under an argon atmosphere for 5 hours with mechanical stirring. Decant the benzene solution, and wash the residue with ether (4×200 mL). Combine the organic layers, wash with saturated brine, dry, filter, concentrate and purify the residue by flash chromatography to give B13.

EXAMPLE 2c

20ξ-Fluoro-21-hydroxypregna-4,17(20)-dien-3-one (B 15)

Add methyl orthoforrnate (6 g) and p-tolenesulphonic acid (0.3 g) to a solution of ketone B13 (5.0 g, 18.2 mmol) in dioxane (50 mL) and stir for two hours. Add pyridine (1.2 mL), dilute the reaction with water (60 mL) and extract with ether (3×30 mL). Dry the combined ether extracts, treat with charcoal, filter and evaporate to give B14 which is used without further purification for the next step.

Slowly and cautiously add diisobutylaluminum hydride (8.0 mL, 80.2 mmol) to a stirred cooled (−78° C.) solution of the above crude B14 and dichloromethane (250 mL). Quench the reaction after 1 hour with a solution of acetic acid (5 mL) in dichloromethane (10 mL). Dilute the reaction mixture with dichloromethane (300 mL) and shake with saturated potassium sodium tartrate (300 mL). Filter the resultant emulsion through a Celite® pad, separate the organic layer and wash sequentially with saturated potassium sodium tartrate (150 mL), saturated sodium bicarbonate (150 mL), and brine (150 mL). Dry, filter and concentrate the organic phase. Hydrolyze the enol ether moiety with hydrochloric acid as described in General Procedure 4 to afford crude B15 after concentration. Dissolve the residue in dichloromethane, place atop a column of silica gel and purify by flash chromatography to afford pure 20ξ-fluoro-21-hydroxypregna-4,17(20)-dien-3-one (B15).

EXAMPLE 2d 21,21-Dimethyl-3β-[[(1,1-dimethylethyl) dimethylsilyl]oxy]-20ξ-fluoropregna-5,17(20)-dien-21-ol (B16)

Dissolve ester A3 (5.0 g, 10.2 mmol) in anhydrous diethyl ether (200mL) and THF (100 mL). Cool the resulting solution in an ice-water bath and treat with methylmagnesium bromide (13.5 mL of a 3.0M solution in ether, 40.5 mmol). Quench the reaction after 4 hours by pouring the reaction mixture into cold water (200 mL) containing acetic acid (10 mL). Separate the aqueous layer and extract with ether (2×200 mL). Wash the combined organic layer and ether extract with water, dry, filter and concentrate to give a solid. Purify the solid by flash chromatography to afford B16 as a mixture of stereoisomers.

EXAMPLE 2e 21,21-Dimethyl-20ξ-fluoropregna-5,17(20)-diene-3β,21-diol (B17)

Add tetrabutyl-ammonium fluoride. (3.0 mL of a 1.0 M solution in THF, 3.0 mmol) to compound B16 (500 mg, 1.05 mmol), under nitrogen, and stir the resultant solution at room temperature for 23 hours. Add the reaction solution dropwise to vigorously stirred water (50 mL) and filter the resultant suspension. Dry the filter cake to give crude B17 and purify B17 by flash chromatography.

EXAMPLE 3a

1α-propylandrosta-3,17-dione (C19c)

Add a 10% solution of tri-propylaluminum in toluene (42.6 mL, 49.5 mmol) to a solution of androsta-1,4-diene-3,17-dione (C18, 12.38 g, 45 mmol) and cuprous bromide (129 mg, 0.9 rtnol) dissolved in tetrahydrofuran (200 mL) under a nitrogen atmosphere. Add trimethylsilyl chloride (5.88 g, 54 mmol) dropwise to the solution. After 2 hours, cautiously add water (5 mL). Filter the solids off and wash. Purify the crude product by flash chromatography to give 1α-propylandrosta-3,17-dione (C19c).

Similarly prepared are the known compounds (Westerrnann, J. and Nickisch, K., 1993, *Angew. Chem. Int. Ed. Engl.*, 32, 1368–1370):

1α-methylandrosta-3,17-dione (C19a)

1α-ethylandrosta-3,17-dione (C19b)

EXAMPLE 3b

Experimental procedures for the synthesis of compounds C20a–c from C19a–c can be found in General Procedure 1.

3-Methoxy- 1α-methylandrost-5-en-17-one (C20a)

1α-Ethyl-3-methoxyandrost-5-en-17-one (C20b)

3-Methoxy-1α-propylandrost-5-en-17-one (C20c)

EXAMPLE 3c

Experimental procedures for the synthesis of compounds C21a–c from C20a–c can be found in General Procedure 2.

20ξ-Fluoro-3-methoxy-1α-methylpregna-3,5,17(20)-trien-21-oic Acid Ethyl Ester (C21a)

1α-Ethyl-20ξ-fluoro-3-methoxypregna-3,5,17(20)-trien-21-oic Acid Ethyl Ester (C21b)

20ξ-Fluoro-3-methoxy-1α-propylpregna-3,5,17(20)-trien-21-oic Acid Ethyl Ester (C21c)

EXAMPLE 3d

Experimental procedures for the synthesis of compounds C23 from C21 and their intermediates C22 can be found in General Procedures 4.

20ξ-Fluoro-21-hydroxy-1α-methylpregna-4,17(20)-dien-3-one (C23a);

1α-Ethyl-20ξ-fluoro-21-hydroxypregna-4,17(20)-dien-3-one (C23b)

20ξ-Fluoro-21-hydroxy-1α-propylpregna-4,17(20)-dien-3-one (C23c)

EXAMPLE 3e

Experimental procedures for the synthesis of compounds C24 from C21 can be found in General Procedures 3.

20ξ-Fluoro-1α-methylpregna-4,17(20)-dien-3-on-21-oic Acid Ethyl Ester (C24a)

1α-Ethyl-20ξ-fluoropregna-4,17(20)-dien-3-one-21-oic Acid Ethyl Ester (C24b)

20ξ-Fluoro-1α-propylpregna-4,17(20)-dien-3-one-21-oic Acid Ethyl Ester (C24c)

EXAMPLE 4a

3-Acetoxy-20ξ-fluoro-1α-methylpregna-3,5,17(20)-triene-21-oic Acid Ethyl Ester (D25a)

Stir a solution of 20ξ-fluoro-1α-methylpregna-4,17(20)-dien-3-on-21-oic acid ethyl ester (C24a, 2.5 g 6.43 mmol) in ethyl acetate (250 mL), acetic anhydride (25 mL) and 70% perchloric acid (0.10 mL) at room temperature for 1 hour. Extract the solution with saturated sodium bicarbonate (100 mL) and brine (100 mL). Dry and concentrate to give 3-acetoxy-20ξ-fluoro-1α-methylpregna-3,5,17(20)-triene- 21-oic acid ethyl ester (D25a) which one may purify by crystallization or use directly in the next step.

By this means the following compounds may be prepared:

3-acetoxy-1α-ethyl-20ξ-fluoropregna-3,5,17(20)-triene-21-oic acid ethyl ester (D25b)

3-acetoxy-20ξ-fluoro-1α-propylpregna-3,5,17(20)-triene-21-oic acid ethyl ester (D25c)

EXAMPLE 4b

20ξ-Fluoro-3β-hydroxy-1α-methylpregna-5,17(20)-dien-21-oic Acid Ethyl Ester (D26a)

Add sodium borohydride (0.40 g, 10.6 mmol) to a solution of 3-acetoxy-20ξ-fluoro-1α-methylpregna-3,5,17(20)-triene-21-oic acid ethyl ester (D25a, 2.23 g, 5.18 mmol) in ethanol (400 mL) and tetrahydrofuran (just enough to effect solution). Stir overnight and add formic acid dropwise until gas evolution ceases. Concentrate to remove the solvents. Dissolve the residue in ethyl acetate (300 mL), wash with water (3×100 mL), dry and concentrate. Purify the residue by flash chromatography to give 20ξ-fluoro-3β-hydroxy-1α-methylpregna-5,17(20)-dien-21-oic acid ethyl ester (D26a).

By this means the following compounds are prepared:

1α-Ethyl-20ξ-fluoro-3β-hydroxypregna-5,17(20)-dien-21-oic Acid Ethyl Ester (D26b)

20ξ-Fluoro-3β-hydroxy-1α-propylpregna-5,17(20)-dien-21-oic Acid Ethyl Ester (D26c)

EXAMPLE 4c

The experimental procedure for the reduction of D26a–c to D27a–e can be found in General Procedures 4 wherein the final acid hydrolysis step is omitted.

20ξ-Fluoro-1α-methylpregna-5,17(20)-diene-3β,21-diol (D27a)

1α-Ethyl-20ξ-fluoro-pregna-5,17(20)-diene-3β,21-diol (D27b)

20ξ-Fluoro-1α-propylpregna-5,17(20)-diene-3β,21-diol (D27c)

EXAMPLE 5a

2α-Ethylandrost-4-ene-3-dione (E28b)

Add ethyl formate (3.03 g, 40.9 mmol) to a mixture of testosterone (E28 R=H, 1.92 g, 6.66 mmol) in toluene (125 mL). Add sodium ethylate (3.40 g, 50 mmol), stopper the mixture and allow to stand at room temperature for 5 days. Remove the solids by filtration, wash with ether, suspend in ether (200 mL) and make acidic with 10% aq hydrochloric acid. Separate the organic layer, wash with brine, dry, and concentrate to give crude 2-hydroxymethylenetestosterone.

Dissolve the above crude material in acetone (10 mL), add iodoethane (1.0 mL, 9.60 mmol) and potassium carbonate (0.60 g, 4.34 mmol), and reflux the mixture overnight. Cool the reaction; dilute with ether (150 mL); wash with water (1×25 mL), 10% aq sodium hydroxide (3×25 mL), and water (1×25 mL); and concentrate. Dissolve the residue in acetone (50 mL), treat with 1 N hydrochloric acid (25 mL) and stir overnight at room temperature. Remove the acetone on a rotary evaporator and extract the residue with ether (3×100 mL). Combine the ether extracts, dry, and concentrate to give crude 2α-ethyl-17β-hydroxyandrost-4-en-3-one (E28b) which is purified by flash chromatography.

Add a solution of chromium trioxide (1.67 g, 16.7 mmol) in water (10 mL) and acetic acid (50 mL) to a solution of 2α-ethyltestosterone (E28b, 3.49 g, 11.0 mmol) in acetic acid (100 mL). Stir at room temperature for 1 hour, pour the reaction into water (200 mL) and collect the solids by filtration. Wash the filter cake with water, dry and purify by flash chromatography to give 2α-ethylandrost-4-ene-3,17-dione (E29b).

EXAMPLE 5b

The experimental procedure for the synthesis of E30a–b from steroid-4-en-3-ones E29a–b can be found in General Procedures 1.

3-Methoxy-2α-methylandrost-5-en-17-one (E30a)

2α-Ethyl-3-methoxy-androst-5-en-17-one (E30b)

EXAMPLE 5c

The experimental procedure for the synthesis of E31a–b from ketones E30a–b can be found in General Procedures 2.

20ξ-Fluoro-3-methoxy-2α-methylpregna-3,5,17(20)-trien-21-oic acid ethyl ester (E31a)

2α-Ethyl-20ξ-fluoro-3-methoxypregna-3,5,17(20)-trien-21-oic acid ethyl ester (E31b)

EXAMPLE 5d The experimental procedure for the synthesis of E33a–b from esters E31a–b can be found in General Procedure 4.

20ξ-Fluoro-21-hydroxy-2α-methylpregna-4,17(20)-dien-3-one (E33a)

2α-Ethyl-20ξ-fluoro-21-hydroxypregna-4,17(20)-dien-3-one (E33b)

EXAMPLE 5e

The experimental procedure for the synthesis of E34a–b from esters E31a–b can be found in General Procedures 3.

20ξ-Fluoro-2α-methylpregna-4,17(20)-dien-3-one-21-oic acid ethyl ester (E34a)

2α-Ethyl-20ξ-fluoropregna-4,17(20)-dien-3-one-21-oic acid ethyl ester (E34b)

EXAMPLE 6a

3-Acetoxy-20ξ-fluoro-2α-methylpregna-3,5,17(20)-triene-21-oic acid ethyl ester (F35a)

Stir a solution of 20ξ-fluoro-2α-methylpregna-4,17(20)-dien-3-on-21-oic acid ethyl ester (E34a, 2.5 g, 6.43 mmol) in ethyl acetate (250 mL), acetic anhydride (25 mL) and 70% perchloric acid (0.10 mL) at room temperature for 1 hour. Extract the solution with saturated sodium bicarbonate (100 mL) and brine (100 mL). Dry and concentrate to give F35a which one can purify by crystallization or use directly in the next step.

By this procedure the following compounds may be prepared:

3-acetoxy-2α-ethyl-20ξ-fluoropregna-3,5,17(20)-triene-21-oic acid ethyl ester (F35b)

3-acetoxy-2ξ-fluoro-2α-propylpregna-3,5,17(20)-triene-21-oic acid ethyl ester (F35c)

EXAMPLE 6b

20ξ-Fluoro-3β-hydroxy-2α-methylpregna-5,17(20)-dien-21-oic acid ethyl ester (F36a)

Add sodium borohydride (0.40 g, 10.6 mmol) to a solution of 3-acetoxy-20ξ-fluoro-2α-methylpregna-3,5,17(20)- triene-21-oic acid ethyl ester (F35a, 2.23 g 5.18 mmol) in ethanol (400 mL) and tetrahydrofuran (just enough to effect solution). Stir overnight and add formic acid dropwise until gas evolution ceases. Remove the solvents, dissolve the residue in ethyl acetate (300 mL), wash with water (3×100 mL), dry and concentrate. Purify the residue by flash chromatography to give 20ξ-fluoro-3β-hydroxy-2α-methylpregna-5,17(20)-dien-21-oic acid ethyl ester (F36a).

By this means the following compounds may be prepared:
2α-Ethyl-20ξ-fluoro-3β-hydroxypregna-5,17(20)-dien-21-oic acid ethyl ester (F36b)
20ξ-Fluoro-3β-hydroxy-2α-propylpregna-5,17(20)-dien-21-oic acid ethyl ester (F36c)

EXAMPLE 6c

The experimental procedure for the synthesis of F37a–c starting from esters F36a–c can be found in General Procedures 4.
20ξ-Fluoro-2α-methylpregna-5,17(20)-diene-3β,21-diol (F37a)
2α-Ethyl-20ξ-fluoropregna-5,17(20)-diene-3β,21-diol (F37b)
20ξ-Fluoro-2α-propylpregna-5,17(20)-diene-3β,21-diol (F37c)

EXAMPLE 7a

17β-Hydroxy-4-(2-propyl)androst-4-en-3-one (G38c)

Stir and treat a cooled (0° C. in a salt-ice bath) solution of 4-nor-4-oxasteroid G40 (7 g, 21.1 mmol) in ether (100 mL) and tetrahydrofuran (30 mL) with 2N isobutylmagnesium bromide in ether (15 mL, 30 mmol). Stir the reaction for 18 hours and pour into cold water (500 mL). Acidify the mixture by addition of 10% hydrochloric acid. Remove the aqueous layer and extract with ether (3×150 mL). Wash the combined ether layer and extracts with 20% hydrochloric acid (150 mL), water (150 mL), saturated sodium bicarbonate (150 mL), and brine (150 mL), and then dry and concentrate. Dissolve the residue in methanol (500 mL), add a solution of sodium hydroxide (21 g) in water (100 mL) and reflux the reaction for 6 hours. Cool to room temperature, acidify the reaction with acetic acid and concentrate the solution is to a volume of approximately 50 mL. Pour into water and extract with ethyl acetate (3×150 mL). Wash the combined organic extract with water (150 mL), dry and concentrate to a gum. Purify the gum by flash chromatography to give 17β-hydroxy-4-(2-propyl)androst-4-en-3-one (G38c).

EXAMPLE 7b 4-(2-propyl)androst-4-ene-3,17-dione (G41c)

Cool a solution of alcohol G38c (2.20 g, 6.70 mmol) in acetone (200 mL) to 3° C. in an ice-water bath. Add Jones reagent (ca 3 mL, Djerassi, C., Engle, R. R. and Bowers, A., J. Org. Chem., 1956, 21, 1547) until the greenish color persists. Decompose excess reagent by addition of isopropanol. Remove the solids by filtration and wash with acetone. Combine the filtrate, wash and concentrate to a greenish gum. Purify the gum by flash chromatography to give 4-(2-propyl)androst-4-ene-3,17-dione (G41c).

By this procedure the following compounds may be prepared:
4-methylandrost-4-ene-3,17-dione (G41a)
4-ethylandrost-4-ene-3,17-dione (G41b)
4-butylandrost-4-ene-3,17-dione (G41d)

EXAMPLE 7c

The experimental procedure for the syntheses of G43a–e starting from the steroid-4-en-3-ones G41a–e can be found in General Procedures 1.
3-Methoxy-4-methylandrosta-3,5-dien-17-one (G43a)
4-Ethyl-3-methoxyandrosta-3,5-dien-17-one (G43b)
4-Isopropyl-3-methoxyandrosta-3,5-dien-17-one (G43c)
4-Butyl-3-methoxyandrosta-3,5-dien-17-one (G43d)
4-Chloro-3-methoxyandrosta-3,5-dien-17-one (G43e)

EXAMPLE 7d

The experimental procedure for the syntheses of G44a–e starting from the $C_{17}$ ketones G43a–e can be found in General Procedures 2.
20ξ-Fluoro-3-methoxy-4-methylpregna-3,5,17(20)-trien-21-oic acid ethyl ester (G44a)
4-Ethyl-20ξ-fluoro-3-methoxypregna-3,5,17(20)-trien-21-oic acid ethyl ester (G44b)
4-Isopropyl-20ξ-fluoro-3-methoxypregna-3,5,17(20)-trien-21-oic acid, ethyl ester (G44c)
4-Butyl-20ξ-fluoro-3-methoxypregna-3,5,17(20)-trien-21-oic acid ethyl ester (G44d)
4-Chloro-20ξ-fluoro-3-methoxypregna-3,5,17(20)-trien-21-oic acid ethyl ester (G44e)

EXAMPLE 7e

The experimental procedure for the syntheses of G46a–e starting from esters G44a–e can be found in General Procedures 4.
20ξ-Fluoro-21-hydroxy-4-methylpregna-4,17(20)-diene-3-one (G46a)
4-Ethyl-20ξ-fluoro-21-hydroxypregna-4,17(20)-diene-3-one (G46b)
4-Isopropyl-20ξ-fluoro-21-hydroxypregna-4,17(20)-diene-3-one (G46c)
4-Butyl-20ξ-fluoro-21-hydroxypregna-4,17(20)-diene-3-one (G46d)
4-Chloro-20ξ-fluoro-21-hydroxypregna-4,17(20)-diene-3-one (G46e)

EXAMPLE 7f

The experimental procedure for the syntheses of G47a–e starting from esters G44a–e can be found in General Procedure 3.
20ξ-Fluoro-4-methylpregna-4,17(20)-dien-3-on-21-oic acid ethyl ester (G47a)
4-Ethyl-20ξ-fluoropregna-4,17(20)-dien-3-on-21-oic acid ethyl ester (G47b)
4-Isopropyl-20ξ-fluoropregna-4,17(20)-dien-3-on-21-oic acid ethyl ester (G47c)
4-Butyl-20ξ-fluoropregna-4,17(20)-dien-3-on-21-oic acid ethyl ester (G47d)
4-Chloro-20ξ-fluoropregna-4,17(20)-dien-3-on-21-oic acid ethyl ester (G47e)

EXAMPLE 7g

20ξ-Fluoro-21-hydroxy-1α-methyl-4-nitropregna-4,17(20)-diene-3-one (G49Aa)

Stir a mixture of potassium t-butylate (1.70 g, 15 mmol), and 20ξ-fluoro-21-hydroxy-1α-methylpregna-4,17(20)-diene-3-one (G48Aa, 1.73 g, 5.0 mmol) in t-butanol (25 mL) at room temperature for 2.5 nitrogen atmosphere. Add to the resulting yellow solution isopropyl nitrate (0.51 mL, 5.0 mmol). The reaction becomes deep violet in color. Stir the reaction overnight. Acidify the reaction mixture with acetic acid and dilute the mixture with dichloromethane. Remove the solids by filtration and wash with the same solvent. Combine the filtrate, wash and concentrate to a red-brown semi-solid. Purify the semi-solid by flash chromatography to give 20ξ-fluoro-21-hydroxy-1α-methyl-4-nitropregna-4,17(20)-diene-3-one (G49Aa).

By this procedure the following compounds may be prepared:

20ξ-Fluoro-21-hydroxy-7α-methyl-4-nitropregna-4,17(20)-diene-3-one (G49Ab)

20ξ-Fluoro-21-hydroxy-15α-methyl-4-nitropregna-4,17(20)-diene-3-one (G49Ac)

EXAMPLE 7h

4-Amino-20ξ-fluoro-21-hydroxy-1α-methylpregna-4,17(20)-diene-3-one (G50Aa)

Treat a solution of 20ξ-fluoro-21-hydroxy-1α-methyl-4-nitropregna-4,17(20)-diene-3-one (G49Aa, 2.09 g, 5.35 mmol) in absolute ethanol (30 mL) with Lindlar's catalyst (0.81 g) and quinoline (37 μL) and shake (Paar shaker) under 1 atmosphere of hydrogen for 24 hours. Filter the mixture through a Celite® pad and concentrate the filtrate to a yellow solid. Purify the solid by flash chromatography to afford 4-amino-20ξ-fluoro-21-hydroxy-1α-methylpregna-4,17(20)-diene-3-one (G50Aa).

By this procedure the following compounds may be prepared:

4-amino-20ξ-fluoro-21-hydroxy-7α-methylpregna-4,17(20)-diene-3-one (G50Ab)

4-amino-20ξ-fluoro-21-hydroxy-15α-methylpregna-4,17(20)-diene-3-one (G50Ac).

EXAMPLE 7i

Utilizing the procedures described in examples 7g and 7h, one may prepare G50Ba–c from G48Ba–c.

4-Amino-20ξ-fluoro-1α-methylpregna-4,17(20)-diene-3-on-21-oic acid ethyl ester (G50Ba)

4-Amino-20ξ-fluoro-7α-methylpregna-4,17(20)-diene-3-on-21-oic acid ethyl ester (G50Bb)

4-Amino-20ξ-fluoro-15α-methylpregna-4,17(20)-diene-3-on-21-oic acid ethyl ester (G50Bc)

EXAMPLE 8a

3-Acetoxy-20ξ-fluoro-4-methylpregna-3,5,17(20)-triene-21-oic Acid Ethyl Ester (H51a)

Stir a solution of 20ξ-fluoro-4-methylpregna-4,17(20)-dien-3-on-21-oic acid ethyl ester (G47a, 2.5 g, 6.43 mmol) in ethyl acetate (250 mL), acetic anhydride (25 mL) and 70% perchloric acid (0.10 mL) at room temperature for 1 hour. Extract the solution with saturated sodium bicarbonate (100 mL) and brine (100 mL). Dry and concentrate the organic phase to give 3-acetoxy-20ξ-fluoro-4-methylpregna-3,5,17(20)-triene-21-oic acid ethyl ester (H51a). Purify by crystallization or use directly in the next step.

By this procedure the following compounds may be prepared:

3-acetoxy-4-ethyl-20ξ-fluoropregna-3,5,17(20)-triene-21-oic acid ethyl ester (H51b)

3-acetoxy-4-isopropyl-20ξ-fluoropregna-3,5,17(20)-triene-21-oic acid ethyl ester (H51c)

3-acetoxy-4-butyl-20ξ-fluoropregna-3,5,17(20)-triene-21-oic acid ethyl ester (H51d)

3-acetoxy-4-chloro-20ξ-fluoropregna-3,5,17(20)-triene-21-oic acid ethyl ester (H51e)

EXAMPLE 8b

20ξ-Fluoro-3β-hydroxy-4-methylpregna-5,17(20)-dien-21-oic Acid Ethyl Ester (H52a)

Add sodium borohydride (0.40 g, 10.6 mmol) to a solution of 3-acetoxy-20ξ-fluoro-4-methylpregna-3,5,17(20)-triene-21-oic acid ethyl ester (H51a, 2.23 g, 5.18 mmol) in ethanol (400 mL) and tetrahydrofuran (just enough to effect solution). Stir overnight, add formic acid dropwise until gas evolution ceases. Remove the solvents, dissolve the residue in ethyl acetate (300 mL) and wash with water (3×100 mL). Dry and concentrated the organic phase. Purify the residue by flash chromatography to give 20ξ-fluoro-3β-hydroxy-4-methylpregna-5,17(20)-dien-21-oic acid ethyl ester (H52a).

By this procedure the following compounds may be prepared:

4-Ethyl-20ξ-fluoro-3β-hydroxypregna-5,17(20)-dien-21-oic acid ethyl ester (H52b)

4-Isopropyl-20ξ-fluoro-3β-hydroxypregna-5,17(20)-dien-21-oic acid ethyl ester (H52c)

4-Butyl-20ξ-fluoro-3β-hydroxypregna-5,17(20)-dien-21-oic acid ethyl ester (H52d)

4-Chloro-20ξ-fluoro-3β-hydroxypregna-5,17(20)-dien-21-oic acid ethyl ester (H52e)

EXAMPLE 8c

20ξ-Fluoro-4-methylpregna-5,17(20)-diene-3β,21-diol (H53a)

The experimental procedure for the synthesis of H53a–e starting from esters H52a–e can be found in General Procedures 4.

20ξ-Fluoro-4-methylpregna-5,17(20)-diene-3β,21-diol (H53a)

4-Ethyl-20ξ-fluoropregna-5,17(20)-diene-3β,21-diol (H53b)

20ξ-Fluoro-4-isopropyl-pregna-5,17(20)-diene-3β,21-diol (H53c)

4-Butyl-20ξ-fluoropregna-5,17(20)-diene-3β,21-diol (H53d)

4-Chloro-20ξ-fluoropregna-5,17(20)-diene-3β,21-diol (H53e)

EXAMPLE 9a

The experimental procedure for the syntheses of I57a–c starting from the steroid-4-en-3-ones I56a–c can be found in General Procedures 1.

3-Methoxy-6-methylpregna-3,5-dien-17-one (I57a)

6-Ethyl-3-methoxypregna-3,5-dien-17-one (I57b)

6-Butyl-3-methoxypregna-3,5-dien-17-one (I57c)

EXAMPLE 9b

The experimental procedure for the syntheses of I58a–c starting from the $C_{17}$ ketones I57a–c can be found in General Procedures 2.

20ξ-Fluoro-3-methoxy-6-methylpregna-3,5,17(20)-trien-21-oic acid ethyl ester (I58a)

6-Ethyl-20ξ-fluoro-3-methoxypregna-3,5,17(20)-trien-21-oic acid ethyl ester (I58b)

6-Butyl-20ξ-fluoro-3-methoxypregna-3,5,17(20)-trien-21-oic acid ethyl ester (I58c)

EXAMPLE 9c

The experimental procedure for the syntheses of I60a–c starting from the esters I58a–c can be found in General Procedures 4.

20ξ-Fluoro-21-hydroxy-6-methylpregna-4,17(20)-dien-3-one (I60a)

6-Ethyl-20ξ-fluoro-21-hydroxypregna-4,17(20)-dien-3-one (I60b)

6-Butyl-20ξ-fluoro-21-hydroxypregna-4,17(20)-dien-3-one (I60c)

EXAMPLE 9d

The experimental procedure for the syntheses of I61a–c starting from the esters I60a–c can be found in General Procedures 3.

20ξ-Fluoro-6-methypregna-4,17(20)-dien-3-one-21-oic acid ethyl ester (I612a)

6-Ethyl-20ξ-fluoropregna-4,17(20)-dien-3-one-21-oic acid ethyl ester (I61b)

6-Butyl-20ξ-fluoropregna-4,17(20)-dien-3-one-21-oic acid ethyl ester (I61c)

EXAMPLE 10a

3-Acetoxy-20ξ-fluoro-6-methylpregna-3,5,17(20)-triene-21-oic Acid Ethyl Ester (J62a)

Stir a solution of 20ξ-fluoro-6α-methylpregna-4,17(20)-dien-3-on-21-oic acid ethyl ester (I61a, 2.5 g, 6.43 mmol) in ethyl acetate (250 mL), acetic anhydride (25 mL) and 70% perchloric acid (0.10 mL) at room temperature for 1 hour. Extract the solution with saturated sodium bicarbonate (100 mL) and brine (100 mL). Dry and concentrate the organic phase to give 3-acetoxy-20ξ-fluoro-6-methylpregna-3,5,17(20)-triene-21-oic acid ethyl ester (J62a). Purify the material by crystallization or use it directly in the next step.

By this procedure the following compounds may be prepared:

3-acetoxy-6-ethyl-20ξ-fluoropregna-3,5,17(20)-triene-21-oic acid ethyl ester (J62b)

3-acetoxy-6-butyl-20ξ-fluoropregna-3,5,17(20)-triene-21-oic acid ethyl ester (J62c)

EXAMPLE 10b

20ξ-Fluoro-3-hydroxy-6-methylpregna-5,17(20)-dien-21-oic Acid Ethyl Ester (J63a)

Add sodium borohydride (0.40 g, 10.6 mmol) to a solution of 3-acetoxy-20ξ-fluoro-6-methylpregna-3,5,17(20)-triene-21-oic acid ethyl ester (J62a, 2.23 g, 5.18 mmol) in ethanol (400 mL) and tetrahydrofuran (just enough to effect solution). Stir overnight and add formic acid dropwise until gas evolution ceases. Remove the solvents and dissolve the residue in ethyl acetate (300 mL). Wash with water (3×100 mL), dry and concentrate the organic phase. Purify the residue by flash chromatography to give 20ξ-fluoro-3β-hydroxy-6-methylpregna-5,17(20)-dien-21-oic acid ethyl ester (J63a).

By this procedure the following compounds may be prepared:

4-ethyl-20ξ-fluoro-3β-hydroxypregna-5,17(20)-dien-21-oic acid ethyl ester (J63b)

4-butyl-20ξ-fluoro-3β-hydroxypregna-5,17(20)-dien-21-oic acid ethyl ester (J63c)

EXAMPLE 10c

The experimental procedure for the synthesis of J64a–c starting from esters J63a–c can be found in General Procedures 4.

20ξ-Fluoro-6-methylpregna-5,17(20)-diene-3β,21-diol (J64a)

6-Ethyl-20ξ-fluoropregna-5,17(20)-diene-3β,21-diol (J64b)

6-Butyl-20ξ-fluoropregna-5,17(20)-diene-3β,21-diol (J64c)

EXAMPLE 11a

The experimental procedure for the syntheses of K68a–h starting from the steroid-4-en-3-ones K67a–h can be found in General Procedures 1.

3-methoxy-7α-methylpregna-3,5-dien-17-one (K68a)

7α-Ethyl-3-methoxypregna-3,5-dien-17-one (K68b), 3-methoxy-7α-propylpregna-3,5-dien-17-one (K68c)

7α-Butyl-3-methoxypregna-3,5-dien-17-one (K68d)

3-methoxy-7β-methylpregna-3,5-dien-17-one (K68e)

7β-Ethyl-3-methoxypregna-3,5-dien-17-one (K68f)

3-methoxy-7β-propylpregna-3,5-dien-17-one (K68g)

7β-Butyl-3-methoxypregna-3,5-dien-17-one (K68h)

EXAMPLE 11b

The experimental procedure for the syntheses of K69a–h starting from the $C_{17}$ ketones K68a–h can be found in General Procedures 2.

20ξ-Fluoro-3-methoxy-7α-methylpregna-3,5,17(20)-trien-21-oic acid ethyl ester (K69a)

7α-Ethyl-20ξ-fluoro-3-methoxypregna-3,5,17(20)-trien-21-oic acid ethyl ester (K69b)

20ξ-Fluoro-3-methoxy-7α-propylpregna-3,5,17(20)-trien-21-oic acid ethyl ester (K69c)

7α-Butyl-20ξ-fluoro-3-methoxypregna-3,5,17(20)-trien-21-oic acid ethyl ester (K69d)

20ξ-Fluoro-3-methoxy-7β-methylpregna-3,5,17(20)-trien-21-oic acid ethyl ester (K69e)

7β-Ethyl-20ξ-fluoro-3-methoxypregna-3,5,17(20)-trien-21-oic acid ethyl ester (K69f)

20ξ-Fluoro-3-methoxy-7β-propylpregna-3,5,17(20)-trien-21-oic acid ethyl ester (K69g)

7β-Butyl-20ξ-fluoro-3-methoxypregna-3,5,17(20)-trien-21-oic acid ethyl ester (K69h)

EXAMPLE 11c

The experimental procedure for the syntheses of K71a–h starting from the esters K69a–h can be found in General Procedures 4.

20ξ-Fluoro-21-hydroxy-7α-methylpregna-4,17(20)-dien-3-one (K71a)

7α-Ethyl-20ξ-fluoro-21-hydroxypregna-4,17(20)-dien-3-one (K71b)

20ξ-Fluoro-21-hydroxy-7α-propylpregna-4,17(20)-dien-3-one (K71c)

7α-Butyl-20ξ-fluoro-21-hydroxypregna-4,17(20)-dien-3-one (K71d)

20ξ-Fluoro-21-hydroxy-7β-methylpregna-4,17(20)-dien-3-one (K71e)

7β-Ethyl-20ξ-fluoro-21-hydroxypregna-4,17(20)-dien-3-one (K71f)

20ξ-Fluoro-21-hydroxy-7β-propylpregna-4,17(20)-dien-3-one (K71g)

7β-Butyl-20ξ-fluoro-21-hydroxypregna-4,17(20)-dien-3-one (K71h)

EXAMPLE 11d

The experimental procedure for the syntheses of K72a–h starting from the esters K69a–h can be found in General Procedures 3.

20ξ-Fluoro-7α-methylpregna-4,17(20)-dien-3-one-21-oic acid ethyl ester (K72a)

7α-Ethyl-20ξ-fluoropregna-4,17(20)-dien-3-one-21-oic acid ethyl ester (K72b)

20ξ-Fluoro-7α-propylpregna-4,17(20)-dien-3-one-21-oic acid ethyl ester (K72c)

7α-Butyl-20ξfluoropregna-4,17(20)-dien-3-one-21-oic acid ethyl ester (K72d)

20ξ-Fluoro-7β-methylpregna-4,17(20)-dien-3-one-21-oic acid ethyl ester (K72e)

7β-Ethyl-20ξ-fluoropregna-4,17(20)-dien-3-one-21-oic acid ethyl ester (K72f)

20ξ-Fluoro-7β-propylpregna-4,17(20)-dien-3-one-21-oic acid ethyl ester (K72g)

7β-Butyl-20ξ-fluoropregna-4,17(20)-dien-3-one-21-oic acid ethyl ester (K72h)

EXAMPLE 12a

7α-Methylandrost-5-ene-3β,17β-diol 17 Acetate (L75a)

Add slowly a solution of 7α-methylandrost-5-en-3-on-17β-ol 17 acetate (L74a, 6.3 g, 18.9 mmol) in tetrahydrofuran (50 mL) to a solution of sodium borohydride (0.72 g, 18.9 mmol) in 95% ethanol (200 mL) cooled to −3° C. in a salt/ice bath with stirring. Stir at this temperature for 3 hours and decompose the excess reagent by cautious addition of acetic acid (10 mL). Remove the solvents and purify the resulting crude product by flash chromatography to give 7α-methylandrost-5-ene-3β,17β-diol 17 acetate (L75a) as a white solid. Similarly prepare the following analogs:

7α-Ethylandrost-5-ene-3β,17β-diol 17 Acetate (L75b)

7α-Propylandrost-5-ene-3β,17β-diol 17 Acetate (L75c)

7α-Butylandrost-5-ene-3β,17β-diol 17 Acetate (L75d)

7β-Methylandrost-5-ene-3β,17β-diol 17 Acetate (L75e)

7β-Ethylandrost-5-ene-3β,17β-diol 17 Acetate (L75f)

7-βPropylandrost-5-ene-3β,17β-diol 17 Acetate (L75g)

7β-Butylandrost-5-ene-3β,17β-diol 17 Acetate (L75h)

EXAMPLE 12b

3ξ-[[(1,1-Dimethylethyl)dimethylsilyl]oxy]-7α-methylandrost-5-en-17-ol (L76a)

Add to a stirred solution of 7α-methylandrost-5-ene-3β,17β-diol 17 acetate (L75a, 3.20 g, 9.57 anhydrous DMF (50 mL), under nitrogen, t-butyldimethylsilyl chloride (1.51 g, 10.0 mmol), 4-dimethylaminopyridine (0.06 g, 0.48 mmol) and triethylamine (1.5 mL, 10.6 mmol). Stir the resultant suspension at room temperature for 3 days and then pour into rapidly stirred water (200 mL). Filter the resultant suspension and crystallize the white solid from aqueous acetone to give L76a acetate ester. Standard lithium hydroxide hydrolysis gives L76a. Prepare the following compounds by this procedure:

3β-[[(1,1-Dimethylethyl)dimethylsilyl]oxy]-7α-ethylandost-5-en-17-ol (L76b)

3β-[[(1,1-Dimethylethyl)dimethylsilyl]oxy]-7α-propylandost-5-en-17-ol (L76c)

7α-Butyl-3β-[[(1,1-dimethylethyl)dimethylsilyl]oxy]androst-5-en-17-ol (L76d)

3β-[[(1,1-Dimethylethyl)dimethylsilyl]oxy]-7β-methylandrost-5-en-17-ol (L76e)

3β-[[(1,1-Dimethylethyl)dimethylsilyl]oxy]-7β-ethylandrost-5-en-17-ol (L76f)

3β-[[(1,1-Dimethylethyl)dimethylsilyl]oxy]-7β-propylandrost-5-en-17-ol (L76g)

7β-Butyl-3β-[[(1,1-dimethylethyl)dimethylsilyl]oxy]androst-5-en-17-ol (L76h)

EXAMPLE 12c

3-[[(1,1-Dimethylethyl)dimethylsilyl]oxy]-7α-methylandrost-5-en-17-one (L77a)

Cool a solution of alcohol L76a (5.23 g, 12.49 mmol) in acetone (350 mL) to 3° C. in an ice-water bath and add Jones reagent until the greenish color persists. Decompose the excess reagent by addition of isopropanol. Remove the solids by filtration and wash with acetone. Combine the filtrate and wash, and concentrate to a greenish gum. Purify the gum by flash chromatography to give 3β-[[(1,1-dimethylethyl)dimethylsilyl]-oxy]-7α-methylandrost-5-en-17-one (L77a).

By this procedure the following compounds may be prepared:

3β-[[(1,1-dimethylethyl)dimethylsilyl]oxy]-7α-ethylandrost-5-en-17-one (L77b);

3β-[[(1,1-dimethyethyl)dimethylsilyl]oxy]-7α-propylandrost-5-en-17-one (L77c);

3β-[[(1,1-dimethylethyl)dimethylsilyl]oxy]-7α-butylandrost-5-en-17-one (L77d)

3β-[[(1,1-dimethylethyl)dimethylsilyl]-oxy]-7-methylandrost-5-en-17-one (L77e)

3β-[[(1,1-dimethylethyl)dimethylsilyl]oxy]-7β-ethylandrost-5-en-17-one (L77f);

3β-[[(1,1-dimethylethyl)dimethylsilyl]oxy]-7β-propylandrost-5-en-17-one (L77g);

3β-[[(1,1-dimethylethyl)dimethylsilyl]oxy]-7β-butylandrost-5-en-17-one (L77h)

EXAMPLE 12d

The experimental procedure for the syntheses of L78a–h starting from the $C_{17}$ ketones L77a–h can be found in General Procedure 2.

3-[[(1,1-Dimethylethyl)dimethylsilyl]oxy]-20ξ-fluoro-7α-methylpregna-5,17(20)-dien-21-oic acid ethyl ester (L78a)

3-[[(1,1-Dimethylethyl)dimethylsilyl]oxy]-7α-ethyl-20ξ-fluoropregna-5,17(20)-dien-21-oic acid ethyl ester (L78b)

3-[[(1,1-Dimethylethyl)dimethylsilyl]oxy]-20ξ-fluoro-7α-propylpregna-5,17(20)-dien-21-oic acid ethyl ester (L78c)

7α-Butyl-3-[[(1,1-dimethylethyl)dimethylsilyl]oxy]-20ξ-fluoropregna-5,17(20)-dien-21-oic acid ethyl ester (L78d)

3-[[(1,1-Dimethylethyl)dimethylsilyl]oxy]-20ξ-fluoro-7β-methylpregna-5,17(20)-dien-21-oic acid ethyl ester (L78e)

3-[[(1,1-Dimethylethyl)dimethylsilyl]oxy]-7β-ethyl-20ξ-fluoropregna-5,17(20)-dien-21-oic acid ethyl ester (L78f)

3-[[(1,1-Dimethylethyl)dimethylsilyl]oxy]-20ξ-fluoro-7β-propylpregna-5,17(20)-dien-21-oic acid ethyl ester (L78g)

7β-Butyl-3-[[(1,1-dimethylethyl)dimethylsilyl]oxy]-20ξ-fluoropregna-5,17(20)-dien-21-oic acid ethyl ester (L78h)

EXAMPLE 12e

3-[[(1,1-Dimethylethyl)dimethylsilyl]oxy]-20ξ-fluoro-7α-methylpregna-5,17(20)-dien-21-ol (L79a)

Slowly add diisobutylaluminum hydride (6.75 mL of a 1.0M solution in dichloromethane, 67.5 mmol) to a stirred solution of ester L78a (7.57 g, 15 mmol) in dichloromethane (135 mL) under nitrogen and cooled to −78° C. After 1 hour, quench the reaction with a solution of glacial acetic acid (3.8 mL) in dichloromethane (9 mL) and pour the reaction mixture into dichloromethane (250 mL)/saturated aqueous potassium sodium tartrate (250 mL). Filter the resultant emulsion through a Celite® pad (3 cm), transfer the filtrates to a separatory funnel, and separate the layers. Wash the organic layer with saturated aqueous potassium sodium tartrate (130 mL), saturated aqueous sodium bicarbonate (250 mL), and brine (100 mL). Dry the organic phase, filter, and concentrate to give crude 3-[[(1,1-dimethylethyl)dimethylsilyl]oxy]-20ξ-fluoro-7α-methylpregna-5,17(20)-dien-21-ol (L79a) and purify by flash chromatography.

By this procedure the following compounds are prepared:

3-[[(1,1-Dimethyl-ethyl)dimethylsilyl]oxy]-7α-ethyl-20ξ-fluoropregna-5,17(20)-dien-21-ol (L79b)

3-[[(1,1-Dimethylethyl)dimethylsilyl]oxy]-20ξ-fluoro-7α-propylpregna-5,17(20)-dien-21-ol (L79c)

7α-Butyl-3-[[(1,1-dimethylethyl)dimethylsilyl]oxy]-20ξ-fluoropregna-5,17(20)-dien-21-ol (L79d)

3-[[(1,1-Dimethylethyl)dimethylsilyl]oxy]-20ξ-fluoro-7β-methyl-pregna-5,17(20)-dien-21-ol (L79e)

3-[[(1,1-Dimethylethyl)dimethylsilyl]oxy]-7β-ethyl-20ξ-fluoropregna-5,17(20)-dien-21-ol (L79f)

3-[[(1,1-Dimethylethyl)dimethylsilyl]oxy]-20ξ-fluoro-7β-propylpregna-5,17(20)-dien-21-ol (L79g)

7β-Butyl-3-[[(1,1-dimethylethyl)dimethylsilyl]oxy]-20ξ-fluoropregna-5,17(20)-dien-21-ol (L79h)

EXAMPLE 12f

20ξ-Fluoro-7α-methylpregna-5,17(20)-diene-3β,21-diol (L80a)

Add tetrabutylammonium fluoride (9.0 mL of a 1.0M solution in THF, 9.0 mmol) to t-butyldimethylsilyl ether L79a (923 mg, 2.0 mmol), under nitrogen, and stir the resultant solution at room temperature for 23 hours. Add the reaction solution dropwise to vigorously stirred water (150 mL). Filter the resultant suspension and dry to give 20ξ-fluoro-7α-methylpregna-5,17(20)-diene-3β,21-diol (L80a) as a white solid. Purify the solid by chromatography.

By this procedure the following compounds are prepared:

7α-Ethyl-20ξ-fluoropregna-5,17(20)-diene-3β,21-diol (L80b)

20ξ-Fluoro-7α-propylpregna-5,17(20)-diene-3β,21-diol (L80c)

7α-Butyl-20ξ-fluoropregna-5,17(20)-diene-3β,21-diol (L80d)

20ξ-Fluoro-7β-methylpregna-5,17(20)-diene-3β,21-diol (L80e)

7β-Ethyl-20ξ-fluoropregna-5,17(20)-diene-3β,21-diol (L80f)

20ξ-Fluoro-7β-propylpregna-5,17(20)-diene-3β,21-diol (L80g)

7β-Butyl-20ξ-fluoropregna-5,17(20)-diene-3β,21-diol (L80h)

EXAMPLE 13a

3β-[[(1,1-Dimethylethyl)dimethylsilyl]oxy]androst-5,15-dien-17-one (M82)

Add t-butyldimethylsilyl chloride (5.49 g, 36.4 mmol), 4-dimethylaminopyridine (0.21 g, 1.74 mmol) and triethylarmine (5.32 mL, 38.14 mmol) to a stirred solution of 3β-hydroxyandrosta-5,15-dien-17-one (M81, 10.00 g, 34.8 mmol) in anhydrous DMF (175 mL) under nitrogen. Stir the resultant suspension at room temperature for 3 days and then pour into rapidly stirred water (750 mL). Filter the resultant suspension and crystallize the white solid to give 3β-[[(1,1-dimethylethyl)dimethylsilyl]oxy]androst-5,15-dien-17-one (M82).

EXAMPLE 13b

3β-[[(1,1-Dimethylethyl)dimethylsilyl]oxy]-20ξ-fluoropregna-5,15,17(20)-trien-21-oic Acid Ethyl Ester (M83)

Add lithium hexamethyldisilazide (7.0 mL of a 1.0M solution in THF, 7.0 mmol) to a stirred solution of triethyl 2-fluoro-2-phosphonoacetate (1.52 mL, 7.50 mmol) in THF (30 mL) under nitrogen. Add after 1 hour, a solution of M82 (2.01 g, 5.0 mL) in THF (10 mL) and heat he reaction mixture to reflux. After 2.5 hours, allow the reaction mixture to cool to room temperature and concentrate. Partition the residue between diethyl ether (80 mL) and 0.4M aqueous hydrochloric acid (80 mL). Separate the layers and wash the organic layer with 0.5M aqueous hydrochloric acid (40 mL), saturated aqueous sodium bicarbonate (40 mL), and brine (40 mL). Dry, filter, and concentrate the organic phase to give crude 3β-[[(1,1-dimethylethyl)dimethylsilyl]oxy]-20ξ-fluoropregna-5,15,17(20)-trien-21-oic acid ethyl ester (M83). Purify the material by flash chromatography.

EXAMPLE 13c (17Z)-3β-[[(1,1-Dimethylethyl)dimethylsilyl]oxy]-20-fluoropregna-5,15,17(20)-trien-21-ol (M84) and (17E)-3β[[(1,1-Dimethylethyl)dimethylsilyl]oxy]-20-fluoropregna-5,15,17(20)-trien-21-ol (M85)

Slowly add diisobutylaluminum hydride (21.8 mL of a 1.0M solution in dichloromethane, 21.8 mmol) to a stirred, cooled (−78° C.) solution of M83 (2.43 g, 4.95 mmol) in dichloromethane (50 mL) under nitrogen. After 1 hour quench the reaction with a solution of glacial acetic acid (1.3 mL) in dichloromethane (3 mL) and pour the reaction mixture into dichloromethane (100 mL)/saturated aqueous potassium sodium tartrate (100 mL). Filter the resultant emulsion through a Celite® pad (3 cm), transfer the filtrates to a separatory funnel, and separate the layers. Wash the organic layer with saturated aqueous potassium sodium tartrate (130 mL), saturated aqueous sodium bicarbonate (250 mL), and brine (100 mL). Dry, filter, and concentrate the organic phase to give the crude product. Purification by flash chromatography gives M84 and M85.

EXAMPLE 13d (17Z)-20-Fluoropregna-5,15,17(20)-triene-3β,21-diol (M86)

Add tetrabutylammonium fluoride (0.85 mL of a 1.0M solution in THF, 0.85 mmol) to compound M84 (100 mg, 0.192 mmol), under nitrogen, and stir the resultant solution at room temperature for 23 hours. Add the reaction solution dropwise to vigorously stirred water (20 mL) and filter the resultant suspension. Dry the filter cake to give (17Z)-20-fluoropregna-5,15,17(20)-triene-3β,21-diol (M86) a white solid.

EXAMPLE 13e (17E)-20-Fluoropregna-5,15,17(20)-triene-3β,21-diol (M87)

Add tetrabutylammonium fluoride (6.0 mL of a 1.0M solution in THF, 6.0 mmol) to compound M85 (704 mg, 1.35 mmol), under nitrogen, and stir the resultant solution at room temperature for 23 hours. Add the reaction solution dropwise to vigorously stirred water (100 mL) and filter the resultant suspension. Dry the filter cake to give (17E)-20-fluoropregna-5,15,17(20)-triene-3β,21-diol (M87) as a white solid.

EXAMPLE 14a

3β-[[(1,1-Dimethylethyl)dimethylsilyl]oxy]-15α-methylandrost-5-en-17-one (N88a)

Prepare M82 by treating a solution of M81 in DMF with t-butyldimethylsilyl chloride following the procedure described in example 13a. To a solution of 3β-[[(1,1-dimethylethyl)dimethylsilyl]oxy]androst-5,15-dien-17-one (M82) (10.0 g, 24.96 mmol) and cuprous bromide (71.5 mg, 0.5 mmol) dissolved in tetrahydrofuran (100 mL) under a nitrogen atmosphere, add a 2M solution of trimethylaluminum in toluene (13.8 mL, 27.6 mmol). Add trimethylsilyl chloride (5.88 g, 54 mmol) dropwise to the solution. After 2 hours, add water (5 mL) cautiously. Remove the solids by filtration and wash. Purify the crude product by flash chromatography to give 3β-[[(1,1-dimethylethyl)dimethylsilyl]oxy]-15α-methylandrost-5-en-17-one (N88a).

By this procedure the following compounds are prepared:

3β-[[(1,1-Dimethylethyl)dimethylsilyl]oxy]-15α-ethylandrost-5-en-17-one (N88b)

15α-Butyl-3β-[[(1,1-dimethylethyl)dimethylsilyl]oxy]androst-5-en-17-one (N88c)

EXAMPLE 14b

The experimental procedure for the syntheses of N89a–c starting from the $C_{17}$ ketones N88a–c can be found in General Procedure 2.

3β-[[(1,1-Dimethylethyl)dimethylsilyl]oxy]-20ξ-fluoro-15α-methylpregna-5,17(20)-dien-21-oic acid ethyl ester (N89a)

3β-[[(1,1-Dimethylethyl)dimethylsilyl]oxy]-15α-ethyl-20ξ-fluoropregna-5,17(20)-dien-21-oic acid ethyl ester (N89b)

15α-Butyl-3β-[[(1,1-dimethylethyl)dimethylsilyl]oxy]-20ξ-fluoropregna-5,17(20)-dien-21-oic acid ethyl ester (N89c)

EXAMPLE 14c

3β-[[(1,1-Dimethylethyl)dimethylsily]oxy]-20ξ-fluoro-15α-methylpregna-5,17(20)-dien-21-ol (N90a)

Slowly add diisobutylaluminum hydride (9.34 mL of a 1.0M solution in dichloromethane, 9.34 mmol) to a stirred, cooled (−78° C.) solution of N89a (1.07 g, 2.12 mmol) in dichloromethane (25 mL) under nitrogen. Quench the reaction after 1 hour with a solution of glacial acetic acid (0.6 mL) in dichloromethane (2 ml), and pour the reaction mixture into dichloromethane (50 mL)/saturated aqueous potassium sodium tartrate (50 mL). Filter the resultant emulsion through a Celite® pad (3 cm), transfer the filtrates to a separatory funnel, and separate the layers. Wash the organic layer with saturated aqueous potassium sodium tartrate (60 mL), saturated aqueous sodium bicarbonate (100 mL), and brine (50 mL). Dry, filter, and concentrate the organic phase to give the crude product. Purify the material by flash chromatography to give 3β-[[(1,1-dimethylethyl)dimethylsilyl]oxy]-20ξ-fluoro-15α-methylpregna-5,17(20)-dien-21-ol (N90a).

By this procedure the following compounds are prepared:

3β-[[(1,1-Dimethylethyl)dimethylsilyl]oxy]-15α-ethyl-20ξ-fluoropregna-5,17(20)-dien-21-ol (N90b)

15α-Butyl-3β-[[(1,1-dimethylethyl)dimethylsily]oxy]-20ξ-fuoropregna-5,17(20)-dien-21-ol (N90c)

EXAMPLE 14d

20ξ-fluoro-15α-methylpregna-5,17(20)-dien-3β,21-ol (N91a)

Add tetrabutylammnonium fluoride (0.85 mL of a 1.0M solution in THF, 0.85 mmol) to compound N90a (100 mg, 0.192 mmol), under nitrogen, and stir the resultant solution at room temperature for 23 hours. Add the reaction solution dropwise to vigorously stirred water (20 mL) and filter the resultant suspension. Dry the filter cake to give 20ξ-fluoro-15α-methylpregna-5,17(20)-dien-3β,21-ol (N91a) a white solid.

By this procedure the following compounds are prepared:

15α-Ethyl-20ξ-fluoropregna-5,17(20)-dien-3β,21-ol (N91b)

15α-Butyl-20ξ-fluoropregna-5,17(20)-dien-3β,21-ol N91c)

EXAMPLE 15a

3β-[[(1,1-Dimethylethyl)dimethylsilyl]oxy]-20ξ-fluoro-19-norpregna-5,17(20)-dien-21-oic Acid, Ethyl Ester (O98)

Prepare O93 from O92 by treating with acetic anhydride as described for the synthesis of J62 in example 10a, and then treat O93 with sodium borohydride to provide O94 as described for the preparation of J63 in example 10b. Add t-butyldimethylsilyl chloride (16.44 g, 109.1 mmol), 4-dimethylaminopyridine (0.62 g, 5.20 mmol) and triethylamine (15.9 mL, 114.3 mmol) to a stirred solution of estr-5-ene-3β,17β-diol 17-acetate (O94, 33.1 g, 103.9 mmol, Campbell, J. A. and Babcock, J. C., 1971, U.S. Pat. No. 3,597,418) in anhydrous DMF (350 mL) under nitrogen. Stir the resultant suspension at room temperature for 3 days and then pour into vigorously stirred water (2.5 L). Filter the resultant suspension to give 3β-[[(1,1-dimethylethyl) dimethylsilyl]oxy]estr-5-en-17β-ol 17 acetate (O95) as an off-white solid.

Add methanol (150 mL) to a solution of acetate O95 (38.2 g, 88.3 mmol) in tetrahydrofuran (350 mL) and then add a solution of potassium carbonate (15 g, 109 mmol) in water (150 mL). Heat the resulting solution to reflux for 2.5 hours. Remove the organic solvents and partition the remaining mixture between dichloromethane (500 mL) and water (200 mL). Separate the organic layer, dry and concentrate to give 3β-[[(1,1-dimethylethyl)dimethylsilyl]oxy]estr-5-en-17β-ol (O96).

Add pyridinium dichromate (90 g, 239 mmol) to a solution of the above $C_{17}$ alcohol O96 (30.6 g, 81.3 mmol) dissolved in pyridine (500 mL). Stir the mixture at room temperature for 2 days. Dilute the reaction with ether (1 L) and toluene (1 L), and filter the resulting mixture through a pad of Celite®. Wash the filtrate with water (3×750 mL) and then with saturated brine. Dry the organic phase and concentrate. Purify the residue by flash chromatography to give 3β-[[(1,1-dimethylethyl)dimethylsilyl]oxy]-estr-5-en-17-one (O97).

Added lithium hexamethyldisilazide (80 mL of a 1.0M solution in THF, 80 mmol) to a stirred solution of triethyl 2-fluoro-2-phosphonoacetate (17.3 mL, 85.4 mmol) in THF (350 mL) under nitrogen. After 1 hour, add a solution of ketone O97 (21.3 g, 56.9 mmol) in THF (100 mL) and heat the reaction mixture to reflux. After 2.5 hours, cool the reaction mixture to room temperature and concentrate. Partition the residue between diethyl ether (750 mL) and 0.4M aqueous hydrochloric acid (750 mL). Separate the layers and wash the organic layer with 0.5M aqueous hydrochloric acid (400 mL), saturated aqueous sodium bicarbonate (400 mL), and brine (400 mL). Dry, filter, and concentrate the organic phase to give crude 3β-[[(1,1-dimethylethyl)-dimethylsilyl] oxy]-20ξ-fluoro-19-norpregna-5,17(20)-dien-21-oic acid ethyl ester (O98). Purify the crude material by flash chromatography.

EXAMPLE 15b

3β-[[(1,1-Dimethylethyl)dimethylsilyl]oxy]-20ξ-fluoro-19-norpregna-5,17(20)-dien-21-ol (O99)

Slowly add diisobutylaluminum hydride (2.18 mL of a 1.0M solution in dichloromethane, 2.18 mmol) to a stirred, cooled (−78° C.) solution of O98 (2.36 g, 4.95 mmol) in dichloromethane (50 mL) under nitrogen. After 1 hour, quench the reaction with a solution of glacial acetic acid (1.3 mL) in dichloromethane (3 mL) and pour the reaction mixture into dichloromethane (100 mL)/saturated aqueous potassium sodium tartrate (100 mL). Filter the resultant emulsion through a Celite® pad (3 cm), transfer the filtrates to a separatory funnel, and separate the layers. Wash the organic layer with saturated aqueous potassium sodium tartrate (45 mL), saturated aqueous sodium bicarbonate (100 mL), and brine (50 mL). Dry, filter, and concentrate the organic phase to give crude O99. Purify the crude material by flash chromatography or use the crude material directly in the next step.

EXAMPLE 15c

20ξ-Fluoro-19-norpregna-5,17(20)-diene-3β,21-diol (O100)

Add tetrabutylammonium fluoride (14.0 mL of a 1.0M solution in THF, 14.0 mmol) to compound O99 (0.652 g, 1.50 mmol) and stir the resultant solution at room temperature for 30 hours. Add the reaction solution slowly to vigorously stirred cold water (250 mL), filter the resultant suspension and dry the filter cake. Purify the crude material by flash chromatography to give 20ξ-fluoro-19-norpregna-5,17(20)-diene-3β,21-diol (O100).

General Procedure 1: Protection of the $C_3$ Ketones

Method A. (After the method described in Dusza et al., *J. Org. Chem.*, 1962, 27, 4046–4049 and Burn, D., Cooley, G., Davies, M. T., Ducker, J. W., Ellis, B., Feather, P., Hiscock, A. K., Kirk, D. N., Leftwick, A. P., Petrow, V. and Williamson, D. M., 1964, *Tetrahedron*, 20, 597–609) Add methyl orthoformate (12 mL) and p-tolenesulphonic acid (0.3 g) to a solution of $\Delta^4$-3-ketosteroid (5.0 g) in dioxane (50 mL) and stir the resulting solution for 2 hours. Add pyridine (1.2 mL) and pour the reaction into water (500 mL). Collect the solids by filtration, wash with water and dry to give the crude material. Purify the dienol ethers by crystallization.

Method. B. Following the method of Broess et al. (Broess, A. I. A., van Vliet, N. P., Groen, M. B. and Hamersma, H. *Steroids*, 1992, 57, 514–521) cool a suspension of $\Delta^4$-3-ketosteroid (3.30 g) in a mixture of anhydrous methanol (10 mL) and trimethyl orthoformate (5 mL) to 0° C. Add to this suspension p-toluenesulfonic acid (50 mg) and stir the mixture for 7 hours. Basify the reaction mixture by addition of triethylarmine (1 mL) and collect the resulting solids by filtration to give the desired dienol ether.

3-Methoxy-1α-methylandrost-5-en-17-one (C20a) (Method B)

1α-Ethyl-3-methoxy-androst-5-en-17-one (C20b) (Method B)

3-Methoxy-1α-propylandrost-5-en-17-one (C20c) (Method B)

3-Methoxy-2α-methylandrost-5-en-17-one (E30a) (Method B)

2α-Ethyl-3-methoxyandrost-5-en-17-one (E30b) (Method B)

3-Methoxy-4-methylandrosta-3,5-dien-17-one (G43a) (Method B)

4-Ethyl-3-methoxyandrosta-3,5-dien-17-one (G43b) (Method B)

4-Isopropyl-3-methoxyandrosta-3,5-dien-17-one (G43c) (Method B)

4-Butyl-3-methoxyandrosta-3,5-dien-17-one (G43d) (Method B)

4-Choro-3-methoxyandrosta-3,5-dien-17-one (G43e) (Method A)

3-Methoxy-6-methylpregna-3,5-dien-17-one (I57a) (Method A)

6-Ethyl-3-methoxypregna-3,5-dien-17-one (I57b) (Method A)

6-Butyl-3-methoxypregna-3,5-dien-17-one (I57c) (Method A)

3-methoxy-7α-methylpregna-3,5-dien-17-one (K68a) (Method B)

7α-Ethyl-3-methoxypregna-3,5-dien-17-one (K68b) (Method B)

3-methoxy-7α-propylpregna-3,5-dien-17-one (K68c) (Method B)

7α-Butyl-3-methoxypregna-3,5-dien-17-one (K68d) (Method B)

3-methoxy-7β-methylpregna-3,5-dien-17-one (K68e) (Method B)

7β-Ethyl-3-methoxypregna-3,5-dien-17-one (K68f) (Method B)

3-methoxy-7β-propylpregna-3,5-dien-17-one (K68g) (Method B)

7β-Butyl-3-methoxypregna-3,5-dien-17-one (K68h) (Method B)

General Procedure 2: Wittig Reaction of $C_{17}$ Ketones

Add lithium hexamethyldisilazide (3.50 mL of a 1.0M solution in THF, 3.50 mmol) to a stirred solution of triethyl 2-fluoro-2-phosphonoacetate (0.76 mL, 3.75 mmol) in THF (15 mL) under nitrogen. After 1 hour, add a solution of the $C_{17}$ ketone (1.01 g) in tetrahydrofuran (5 mL) and heat the reaction mixture to reflux. After 2.5 hours, cool the reaction mixture to room temperature and concentrate. Partition the residue between diethyl ether (40 mL) and 0.4M aqueous hydrochloric acid (40 mL). Separate the layers and wash the organic layer with 0.5M aqueous hydrochloric acid (20 mL), saturated aqueous sodium bicarbonate (20 mL), and brine (20 mL). Dry, filter, and concentrate the organic phase to give the crude vinyl fluoride. Normal phase flash chromatography gives pure vinyl fluoride. Prepare the following $C_3$ protected $C_{20}$-fluoro-$C_{21}$-carboxylates by this method:

20ξ-Fluoro-3-methoxy-1α-methylpregna-3,5,17(20)-trien-21-oic Acid, Ethyl Ester (C21a)

1α-Ethyl-20ξ-fluoro-3-methoxypregna-3,5,17(20)-trien-21-oic Acid, Ethyl Ester (C21b)

20ξ-Fluoro-3-methoxy-1α-propylpregna-3,5,17(20)-trien-21-oic Acid, Ethyl Ester (C21c)

20ξ-Fluoro-3-methoxy-2α-methylpregna-3,5,17(20)-trien-21-oic Acid, Ethyl Ester (E31a)

2α-Ethyl-20ξ-fluoro-3-methoxypregna-3,5,17(20)-trien-21-oic Acid, Ethyl Ester (E31b)

20ξ-Fluoro-3-methoxy-4-methylpregna-3,5,17(20)-trien-21-oic Acid, Ethyl Ester (G44a)

4-Ethyl-20ξ-fluoro-3-methoxypregna-3,5,17(20)-trien-21-oic Acid, Ethyl Ester (G44b)

4-Isopropyl-20ξ-fluoro-3-methoxypregna-3,5,17(20)-trien-21-oic Acid, Ethyl Ester (G44c)

4-Butyl-20ξ-fluoro-3-methoxypregna-3,5,17(20)-trien-21-oic Acid, Ethyl Ester (G44d)

4-Chloro-20ξ-fluoro-3-methoxypregna-3,5,17(20)-trien-21-oic Acid, Ethyl Ester (G44e)

20ξ-Fluoro-3-methoxy-6-methylpregna-3,5,17(20)-trien-21-oic Acid, Ethyl Ester (I58a)

6-Ethyl-20ξ-fluoro-3-methoxypregna-3,5,17(20)-trien-21-oic Acid, Ethyl Ester (I58b)

6-Butyl-20ξ-fluoro-3-methoxypregna-3,5,17(20)-trien-21-oic Acid, Ethyl Ester (I58c)

20ξ-Fluoro-3-methoxy-7α-methylpregna-3,5,17(20)-trien-21-oic Acid, Ethyl Ester (K69a)

7α-Ethyl-20ξ-fluoro-3-methoxypregna-3,5,17(20)-trien-21-oic Acid, Ethyl Ester (K69b)

20ξ-Fluoro-3-methoxy-7α-propylpregna-3,5,17(20)-trien-21-oic Acid, Ethyl Ester (K69c)

7α-Butyl-20-fluoro-3-methoxypregna-3,5,17(20)-trien-21-oic Acid, Ethyl Ester (K69d)

20ξ-Fluoro-3-methoxy-7β-methylpregna-3,5,17(20)-trien-21-oic Acid, Ethyl Ester (K69e)

7β-Ethyl-20ξ-fluoro-3-methoxypregna-3,5,17(20)-trien-21-oic Acid, Ethyl Ester (K69f)

20ξ-Fluoro-3-methoxy-7β-propylpregna-3,5,17(20)-trien-21-oic Acid, Ethyl Ester (K69g)

7β-Butyl-20ξ-fluoro-3-methoxypregna-3,5,17(20)-trien-21-oic Acid, Ethyl Ester (K69h)

3-[[(1,1-Dimethylethyl)dimethylsilyl]oxy]-20ξ-fluoro-7α-methylpregna-5,17(20)-dien-21-oic Acid, Ethyl Ester (L78a)

3-[[(1,1-Dimethylethyl)dimethylsilyl]oxy]-7α-ethyl-20ξ-fluoropregna-5,17(20)-dien-21-oic Acid, Ethyl Ester (L78b)

3-[[(1,1-Dimethylethyl)dimethylsilyl]oxy]-20ξ-fluoro-7α-propylpregna-5,17(20)-dien-21-oic Acid, Ethyl Ester (L78c)

7α-Butyl-3-[[(1,1-dimethylethyl)dimethylsilyl]oxy]-20ξ-fluoropregna-5,17(20)-dien-21-oic Acid, Ethyl Ester (L78d)

3-[[(1,1-Dimethylethyl)dimethylsilyl]oxy]-20ξ-fluoro-7β-methylpregna-5,17(20)-dien-21-oic Acid, Ethyl Ester (L78e)

3-[[(1,1-Dimethylethyl)dimethylsilyl]oxy]-7β-ethyl-20ξ-fluoropregna-5,17(20)-dien-21-oic Acid, Ethyl Ester (L78f)

3-[[(1,1-Dimethylethyl)dimethylsilyl]oxy]-20ξ-fluoro-7β-propylpregna-5,17(20)-dien-21-oic Acid, Ethyl Ester (L78g)

7β-Butyl-3-[[(1,1-dimethylethyl)dimethylsilyl]oxy]-20ξ-fluoropregna-5,17(20)-dien-21-oic Acid, Ethyl Ester (L78h)

3β-[[(1,1-Dimethylethyl)dimethylsilyl]oxy]-15α-methylpregna-5-en-21-oic Acid Ethyl Ester (N89a)

3β-[[(1,1-Dimethylethyl)dimethylsilyl]oxy]-15α-ethylpregna-5-en-21-oic Acid Ethyl Ester (N89b)

15α-Butyl-3β-[[(1,1-dimethylethyl)dimethylsilyl]oxy]pregna-5-en-21-oic Acid Ethyl Ester (N89c)

General Procedure 3: Hydrolysis of the Dienol Ethers

Dissolve the dienol ether (5 g) in THF (100 mL). Add 0.1 N aq hydrochloric acid (10 mL) and stir the solution for 3 hours at room temperature. Basify the reaction by addition of solid sodium bicarbonate and remove the solvent keeping the bath temperature below 30° C. Dissolve the residue in dichloromethane, place atop a column of silica gel and purify by flash chromatography to give the pure steroid 4-en-3-one. Prepare the following steroid 4-en-3-ones are prepared by this means:

20ξ-Fluoro-1α-methylpregna-4,17(20)-dien-3-one-21-oic Acid, Ethyl Ester (C24a)

1α-Ethyl-20ξ-fluoropregna-4,17(20)-dien-3-one-21-oic Acid, Ethyl Ester (C24b)

20ξ-Fluoro-1α-propylpregna-4,17(20)-dien-3-one-21-oic Acid, Ethyl Ester (C24c)

20ξ-Fluoro-2α-methylpregna-4,17(20)-dien-3-one-21-oic Acid, Ethyl Ester (E34a)

2α-Ethyl-20ξ-fluoropregna-4,17(20)-dien-3-one-21-oic Acid, Ethyl Ester (E34b)

20ξ-Fluoro-4-methylpregna-4,17(20)-dien-3-on-21-oic Acid, Ethyl Ester (G47a)

4-Ethyl-20ξ-fluoropregna-4,17(20)-dien-3-on-21-oic Acid, Ethyl Ester (G47b)

4-Isopropyl-20ξ-fluoropregna-4,17(20)-dien-3-on-21-oic Acid, Ethyl Ester (G47c)

4-Butyl-20ξ-fluoropregna-4,17(20)-dien-3-on-21-oic Acid, Ethyl Ester (G47d)

4-Chloro-20ξ-fluoropregna-4,17(20)-dien-3-on-21-oic Acid, Ethyl Ester (G47e)

20ξ-Fluoro-6-methylpregna-4,17(20)-dien-3-one-21-oic Acid, Ethyl Ester (I61a)

6-Ethyl-20ξ-fluoropregna-4,17(20)-dien-3-one-21-oic Acid, Ethyl Ester (I61b)

6-Butyl-20ξ-fluoropregna-4,17(20)-dien-3-one-21-oic Acid, Ethyl Ester (I61c)
20ξ-Fluoro-7α-methylpregna-4,17(20)-dien-3-one-21-oic Acid, Ethyl Ester (K72a)
7α-Ethyl-20ξ-fluoropregna-4,17(20)-dien-3-one-21-oic Acid, Ethyl Ester (K72b)
20ξ-Fluoro-7α-propylpregna-4,17(20)-dien-3-one-21-oic Acid, Ethyl Ester (K72c)
7α-Butyl-20ξ-fluoropregna-4,17(20)-dien-3-one-21-oic Acid, Ethyl Ester (K72d)
20ξ-Fluoro-7β-methylpregna-4,17(20)-dien-3-one-21-oic Acid, Ethyl Ester (K72e)
7β-Ethyl-20ξ-fluoropregna-4,17(20)-dien-3-one-21-oic Acid, Ethyl Ester (K72f)
20ξ-Fluoro-7β-propylpregna-4,17(20)-dien-3-one-21-oic Acid, Ethyl Ester (K72g)
7β-Butyl-20ξ-fluoropregna-4,17(20)-dien-3-one-21-oic Acid, Ethyl Ester (K72h)

General Procedure 4: Reduction of $C_{21}$ Carboxylates and Hydrolysis of the Dienol Ethers Slowly add diisobutylaluminum hydride (6.75 mL of a 1.0M solution in dichworomethane, 67.5 mmol) to a stirred, cooled (−78° C.) solution of the steroid ester (15 mmol) in dichloromethane (135 mL) under nitrogen. After 1 hour, quench the reaction with a solution of glacial acetic acid (3.8 mL) in dichloromethane (9 mL) and pour the reaction mixture into dichloromethane (250 mL)/saturated aqueous potassium sodium tartrate (250 mL). Filter the resultant emulsion through a Celite® pad (3 cm), transfer the filtrates to a separatory funnel, and separate the layers. Wash the organic layer with saturated aqueous potassium sodium tartrate (130 mL), saturated aqueous sodium bicarbonate (250 mL), and brine (100 mL). Dry, filter, and concentrate. the organic phase to give the crude $C_{21}$ hydroxy dienol ether product. Compounds D27a–c do not require subsequent acidic hydrolysis.

Dissolve the above $C_{21}$ hydroxy dienol ether (1 g) in THF (20 mL), add 0.1 N aqueous hydrochloric acid (2 mL) and stir the solution 3 hours at room temperature. Basify the reaction by addition of solid sodium bicarbonate and remove the solvent keeping the bath temperature below 30° C. By careful flash chromatography, the $C_{20}$ double bond stereoisomers are generally more separable at this point. If not, isolate the mixture of cis and trans isomers and use as is. Prepare by this means the following 3-keto-20-fluoro-21-hydroxy compounds:

20ξ-Fluoro-21-hydroxy-1α-methylpregna-4,17(20)-dien-3-one (C23a)
1α-Ethyl-20ξ-fluoro-21-hydroxypregna-4,17(20)-dien-3-one (C23b)
20ξ-Fluoro-21-hydroxy-1α-propylpregna-4,17(20)-dien-3-one (C23c)
20ξ-Fluoro-1α-methylpregna-5,17(20)-diene-3β,21-diol (D27a)
1α-Ethyl-20ξ-fluoro-pregna-5,17(20)-diene-3β,21-diol (D27b)
20ξ-Fluoro-1α-propylpregna-5,17(20)-diene-3β,21-diol (D27c)
20ξ-Fluoro-21-hydroxy-2α-methylpregna-4,17(20)-dien-3-one (E33a)
2α-Ethyl-20ξ-fluoro-21-hydroxypregna-4,17(20)-diene-3-one (E33b)
20ξ-Fluoro-2α-methylpregna-5,17(20)-diene-3β,21-diol (F37a)
2α-Ethyl-20ξ-fluoro-pregna-5,17(20)-diene-3β,21-diol (F37b)
20ξ-Fluoro-2α-propylpregna-5,17(20)-diene-3β,21-diol (F37c)
20ξ-Fluoro-21-hydroxy-4-methylpregna-4,17(20)-diene-3-one (G46a)
4-Ethyl-20ξ-fluoro-21-hydroxypregna-4,17(20)-diene-3-one (G46b)
4-Isopropyl-20ξ-fluoro-21-hydroxypregna-4,17(20)-diene-3-one (G46c)
4-Butyl-20ξ-fluoro-21-hydroxypregna-4,17(20)-diene-3-one (G46d)
4-Chloro-20ξ-fluoro-21-hydroxypregna-4,17(20)-diene-3-one (G46e)
20ξ-Fluoro-4-methylpregna-5,17(20)-diene-3β,21-diol (H53a)
4-Ethyl-20ξ-fluoropregna-5,17(20)-diene-3β,21-diol (H53b)
20ξ-Fluoro-4-isopropyl-pregna-5,17(20)-diene-3β,21-diol (H53c)
4-Butyl-20ξ-fluoropregna-5,17(20)-diene-3β,21-diol (H53d)
4-Chloro-20ξ-fluoropregna-5,17(20)-diene-3β,21-diol (H53e)
20ξ-Fluoro-21-hydroxy-6-methylpregna-4,17(20)-dien-3-one (I60a)
6-Ethyl-20ξ-fluoro-21-hydroxypregna-4,17(20)-dien-3-one (I60b)
6-Butyl-20ξ-fluoro-21-hydroxypregna-4,17(20)-dien-3-one (I60c)
20ξ-Fluoro-6-methylpregna-5,17(20)-diene-3β,21-diol (J64a)
6-Ethyl-20ξ-fluoropregna-5,17(20)-diene-3β,21-diol (J64b)
6-Butyl-20ξ-fluoropregna-5,17(20)-diene-3β,21-diol (J64c)
20ξ-Fluoro-21-hydroxy-7α-methylpregna-4,17(20)-dien-3-one (K71a)
7α-Ethyl-20ξ-fluoro-21-hydroxypregna-4,17(20)-dien-3-one (K71b)
20ξ-Fluoro-21-hydroxy-7α-propylpregna-4,17(20)-dien-3-one (K71c)
7α-Butyl-20ξ-fluoro-21-hydroxypregna-4,17(20)-dien-3-one (K71d)
20ξ-Fluoro-21-hydroxy-7β-methylpregna-4,17(20)-dien-3-one (K71e)
7β-Ethyl-20ξ-fluoro-21-hydroxypregna-4,17(20)-dien-3-one (K71f)
20ξ-Fluoro-21-hydroxy-7β-propylpregna-4,17(20)-dien-3-one (K71g)
7β-Butyl-20ξ-fluoro-21-hydroxypregna-4,17(20)-dien-3-one (K71h)

Biological Methods and Results

In vitro $C_{17,20}$ lyase assay: Compounds were tested for inhibition of cynomologous monkey $C_{17,20}$ lyase in vitro using microsomal preparations of the enzyme from testicular tissue. Testes were removed from anesthetized animals and flash frozen in liquid nitrogen. Microsomes were isolated as described in Schatzman et al., Anal. Biochem., 175, 219–226 (1988). The compound to be tested was dissolved in DMSO and diluted in 0.05M potassium phosphate buffer, pH 7.4, to give the desired concentrations of test compound, in an amount which contributes 0.1% v/v DMSO to the total assay volume. Assays contained 0.05M potassium phosphate, pH 7.4, an NADPH regenerating system (1 mM NADPH, 5 mM glucose-6-phosphate, 1 IU/mL glucose-6-phosphate dehydrogenase), test compound, substrate and microsomal protein in a total volume of 0.2 mL. Control assays contained all components, including DMSO, but no test compound. All assays were performed in duplicate. The reaction was initiated by the addition of substrate, 7-$^3$H-17α-hydroxypregnenolone (11.2 mCi/mmole; 0.20 mCi per assay) plus unlabeled 17α-hydroxypregnenolone dissolved in DMSO, contributing 2.5% v/v to the final assay mix, and phosphate buffer, yielding a final concentration of 0.05 mM 17α-hydroxypregnenolone (ca. equal to the $K_m$ vale) to the other assay components. The complete assay was incubated at 34° C. for 6 minutes. Each assay was terminated by addition of 5 mL of chloroform:methanol (2:1) and 0.9 mL water. Carrier steroids representing substrates and products (2.5 μg each of 17α-hydroxypregnenolone, dehydroepiandrosterone, and androst-5-ene-3β,17β-diol and 0.8 mL of distilled, deionized water were added. The steroids were then extracted by the method of Moore and Wilson (Methods in Enzymol., eds, O. Malley, B. W. and Hardman, J. G. 36, 466–474 (1975). The organic phase containing the steroids was evaporated using nitrogen gas, the residues were dissolved in 18% tetrahydrofuran (v/v) in hexane, and the steroids were separated by HPLC on a Si60 (5 mm) column (4×250 mm) using a gradient of 18–22% tetrahydrofuran (v/v) in hexane. Radioactivity in the steriod peaks was measured using a Radiometric Model HS or Model A515 Flo-One detector. The enzyme activity for each assay was calculated from the conversion of substrate to products, and. the results expressed as percent inhibition of control.

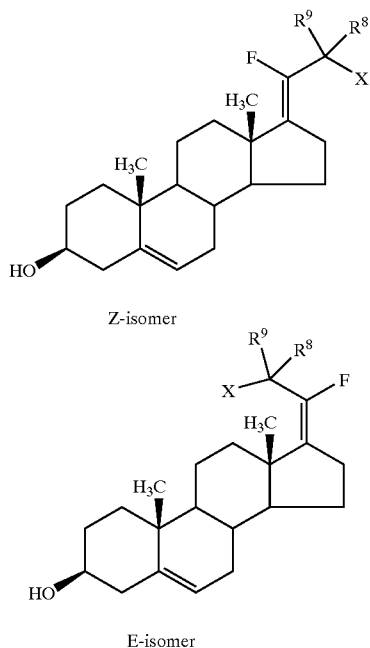

Z-isomer

E-isomer

Inhibition of Cynomolgus Monkey Testicular Lyase

| Isomer | —$CR^8R^9$—X | Conc. (mM) | Preinc. (min.) | % Inhibition |
|---|---|---|---|---|
| Z | $CH_2OH$ | 10 | 0 | 100 |
|   |   | 1 | 0 | 96 |
|   |   | 10 | 40 | 100 |
|   |   | 1 | 40 | 94 |

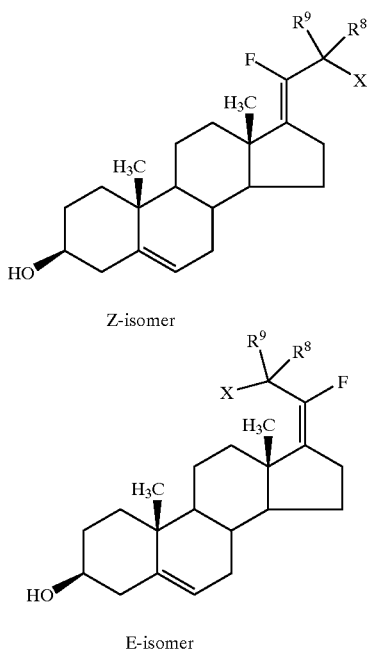

Z-isomer

E-isomer

Inhibition of Cynomolgus Monkey Testicular Lyase

| Isomer | —$CR^8R^9$—X | Conc. (mM) | Preinc. (min.) | % Inhibition |
|---|---|---|---|---|
| E | $CH_2OH$ | 10 | 0 | 85 |
|   |   | 1 | 0 | 63 |
|   |   | 10 | 40 | 87 |
|   |   | 1 | 40 | 61 |
| Z | $CH_3$ | 10 | 0 | 78 |
|   |   | 1 | 0 | 49 |
|   |   | 10 | 40 | 94 |
|   |   | 1 | 40 | 72 |
| E | $CH_3$ | 10 | 0 | 88 |
|   |   | 1 | 0 | 54 |
|   |   | 10 | 40 | 94 |
|   |   | 1 | 40 | 60 |

In vitro 5α-reductase assay: The activity of the present compounds as inhibitors of steroid 5α-reductase was determined using microsomal preparations of the 5α-reductase enzyme from human or laboratory animal prostate tissue. Specifically, prostate tissue was rapidly frozen in liquid nitrogen following removal from the human patient or from a cynomologus monkey (Macaca fascicularis) and subsequently stored at −80° C. The tissue was thawed, minced, and then homogenized in 5 volumes of 0.05M potassium phosphate buffer, pH 7.0, using a Tekmar homogenizer with 3×5 second bursts, followed by 10 strokes in a Dounce homogenizer. The homogenate was sonified in three pulses of 5 seconds each at 50% of maximum power. The homogenate was subjected to differential centrifugation with each supernatant successively centrifuged at 600×G and 900×G in a Beckman J21 centrifuge followed by 120,000×G in a Beckman Model L5-75 ultracentrifuge. The final pellet, containing the microsomal fraction, was reserved and resuspended in 0.05M potassium phosphate buffer, pH 7.0, containing 25% (w/v) glycerol equal to 1 mL per 3 g wet tissue. The suspension was divided into aliquots, flash frozen using dry ice in methanol, and stored at −80° C. Enzyme activity was stable for at least 1 year under these conditions. Rat prostate tissue was treated in a similar manner as described above except that fresh prostate tissue was removed from male Sprague-Dawley rats (Charles Rivers), 0.05M potassium phosphate buffer, pH 6.6, was used for homogenization and 0.05M potassium phosphate buffer, pH 6.6, containing 25% (w/v) glycerol was used for storage. Protein concentration was determined by the BioRad dye binding method (BioRad, Richmond, Calif., USA).

Assays of human, cynomologus monkey and rat prostatic 5α-reductase contained 100 mM potassium phosphate-sodium citrate buffer (pH 5.6), 0.1% bovine serum albumin (w/v, Sigma Chemicals), 1.0 mM sodium EDTA, 7–96 μg of microsomal protein, 1.0 mM NADPH, 5.0 mM glucose-6-phosphate, 1 IU/mL glucose-6-phosphate dehydrogenase, [1,2-$^3$H]-testosterone (0.15 μCi, DuPont-New England Nuclear,), unlabeled testosterone to yield the desired concentration of substrate, and test compound which was dissolved in DMSO and then diluted in 100 mM potassium phosphate-sodium citrate buffer (pH 6.5) to yield a final assay concentration of 0.1% (v/v) DMSO. The same buffer and DMSO without test compound were used in control assays. Background radioactivity was determined from assays containing all components except enzyme. Assays were performed in duplicate. The reaction was initiated by the addition of testosterone and incubated for 30 minutes at 25° C. in a Dubnoff shaker incubator. The compound to be tested for inhibition was added simultaneously with testosterone. The total volume of the assay was 100 μL. The assay was linear with time to 30 minutes under these conditions. For IC$_{50}$ determinations, a single concentration of testosterone at the K$_m$ level was used. Testosterone concentration was varied over a range of 0.5K$_m$ to 8K$_m$ for determination of inhibition mechanism and K$_i$ values. The K$_m$ values of testosterone, determined in multiple experiments, ranged from 0.125–0.273 μM for human 5α-reductase, 0.025–0.091 μM for cynomolgus monkey 5α-reductase, and 0.74–0.90 μM for rat 5α-reductase.

Each assay was terminated by addition of 5 mL of chloroform:methanol (2:1) and 0.9 mL of water. Carrier steroids representing substrates and products (2.5 μg each of testosterone, 5α-dihydrotestosterone, and 3,17-androstenediol) were added. The steroids were extracted by the method of Moore and Wilson (Methods in Enzymol., eds, O. Malley, B. W. and Hardman, J. G. 36, 466–474 (1975).

The organic phase containing the steroids was evaporated using nitrogen gas, the residues were dissolved in 3% isopropanol (v/v) in hexane, and the steroids were separated by normal phase HPLC (LiCrosorb® DIOL derivatized silica gel column (10 μM; 4×250 mm; EM Sciences, Gibbstown, N.J.). After injection of sample, the steroids were separated with a 3% to 7.5% isopropanol in hexane gradient over 24 minutes, and then under isocratic conditions for 2 minutes at 75% (v/v) isopropanol in hexane using a flow rate of 1 mL per minute. The column was re-equilibrated with 3% (v/v) isopropanol in hexane prior to the next injection. The retention times were: 5α-dihydrotestosterone, 10.1–11.2 minutes; testosterone, 14.2–16.1 minutes; and 3β,17β-androstanediol, 17.1–20.2 minutes. The HPLC system used to separate the steroid components of the human and rat 5α-reductase assays consisted of Beckman 114M pumps and a 421A controller, a Waters WISP 710B autosampler, a Kratos Spectraflow 783 UV detector (wavelength set at 238 nm) and a Radiomatic model HS radioactivity analyzer. The HPLC system used for analysis of the cynomolgus monkey 5α-reductase assay was composed of a Waters 600E controller and dual pump unit, a Waters WiSP model 715 autosampler, a Waters 486 UV detector (wavelength, 238 nm), and a Radiomatic A515 radioactivity analyzer. FloScint II was used at a ratio of 1.6:1 (scintillant to column effluent) for detection of [$^3$H]-dihydrotestosterone. FloOne HS radioactivity data from the human and rat 5α-reductase assays were analyzed using the Beckman Data Transporter (Beckman Instruments, Fullerton, Calif.), which transferred integrated data collected from the FloOne HS to a mainframe computer and data were analyzed using RS1 (BBN Software Products Corp., Cambridge, Md.). Radioactivity data from the FloOne arising from the cynomolgus monkey 5α-reductase assays were analyzed using Waters Millennium software. Reaction rates were determined by multiplying the initial testosterone concentration by the percent of dihydrotestosterone and 3,17-androstenediol formed.

Concentrations of 10 μM and 1 μM of test compound were used to evaluate inhibitory activity. IC$_{50}$ values were obtained using 6 concentrations of inhibitor. The data from these experiments were fitted to Equation 1 using a Vax computer.

$$f(x)=100/\{1+[X/B_3]^{**}[(B_2{}^*B_3)/-25]\} \qquad \text{Eq. 1}$$

where B$_2$ is the slope at IC$_{50}$ and B$_3$ is the IC$_{50}$ value. Inhibition constants (K$_i$) were determined by fitting the data to the competitive inhibition model using Equation 2 (W. W. Cleland (1963) Biochim. Biophys. Acta, 67, 188–196) by nonlinear regression on a Compaq 386s using Dexter Northrop's MegaBasic program which was adapted from R. Duggleby's procedure (R. Duggleby, (1984) Comput. Biol. Med. 14, 447–455.).

$$v=V_{max}A/[K_m(1+I/K_i)+A] \qquad \text{Eq. 2}$$

where V$_{max}$ is the maximal velocity, A is the concentration of testosterone, I is the test compound concentration and K$_i$ is the inhibition constant. The enzyme activity for each assay was calculated from the percent conversion of substrate to products, and the results were expressed as percent inhibition of control.

What is claimed is:

1. A compound, or a pharmaceutically acceptable salt thereof of the formula:

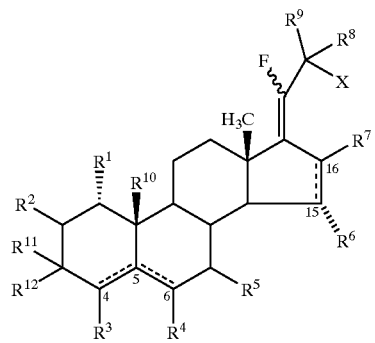

wherein:
R$^1$ is H or C$_{1-4}$ alkyl;
R$^2$ is H or C$_{1-4}$ alkyl;
R$^3$ is H, chloro, nitro, amino or C$_{1-4}$ alkyl;
R$^4$ is H or C$_{1-4}$ alkyl;
R$^5$ is H or C$_{1-4}$ alkyl;
R$^6$ is H or methyl;
R$^7$ is H or methyl;

$R^8$ is H or methyl;
$R^9$ is H or methyl;
  or $R^8$ and $R^9$ taken together is oxo;
$R^{10}$ is H or methyl;
$R^{11}$ is H;
$R^{12}$ is hydroxy;
  or $R^{11}$ and $R^{12}$ taken together is oxo;
X is H, hydroxy or methoxy;
with the proviso that when:
  a) $R^{11}$ is H and $R^{12}$ is hydroxy, bond $C_{4,5}$ is a single bond, bond $C_{5,6}$ is a double bond and bond $C_{15,16}$ is optionally a single bond or a double bond, and
  b) $R^{11}$ and $R^{12}$ taken together is oxo, bond $C_{4,5}$ is a double bond, bond $C_{5,6}$ is a single bond, bond $C_{15,16}$ is a single bond, and $R^8$ and $R^9$ are each methyl or $R^8$ and $R^9$ taken together is oxo.

2. The compound according to claim 1 wherein:
$R^8$ and $R^9$ taken together is oxo;
$R^{11}$ and $R^{12}$ taken together is oxo;
X is hydroxy or methoxy.

3. The compound according to claim 1 wherein:
$R^8$ and $R^9$ are H;
$R^{11}$ and $R^{12}$ taken together is oxo;
X is hydroxy.

4. The compound according to claim 3 wherein $R^{10}$ methyl.

5. The compound according to claim 1 wherein:
$R^8$ and $R^9$ taken together is oxo;
$R^{11}$ is H;
$R^{12}$ is hydroxy;
X is hydroxy or methoxy.

6. The compound according to claim 1 wherein:
$R^8$, $R^9$ and $R^{11}$ are H;
$R^{12}$ is hydroxy;
X is H or hydroxy.

7. The compound according to claim 6 wherein X is hydroxy.

8. The compound according to claim 7 wherein $R^{10}$ is methyl.

9. The compound according to claim 8 wherein $R^1$, $R^2$, $R^3$ and $R^4$ are H.

10. The compound according to claim 9 wherein bond $C_{15-16}$ is a single bond.

11. The compound according to claim 10 which is (17E)-20-fluoropregna-5,17(20)-diene-3β,21-diol.

12. The compound according to claim 10 which is (17Z)-20-fluoropregna-5,17(20)-diene-3β,21-diol.

13. The compound according to claim 6 wherein X is H.

14. The compound according to claim 13 wherein $R^{10}$ is methyl.

15. The compound according to claim 14 wherein $R^1$, $R^2$, $R^3$ and $R^4$ are H.

16. The compound according to claim 15 wherein bond $C_{15-16}$ is a single bond.

17. The compound according to claim 16 which is (17E)-20-fluoropregna-5,17(20)-dien-3β-ol.

18. The compound according to claim 16 which is (17Z)-20-fluoropregna-5,17(20)-dien-3β-ol.

19. A pharmaceutical composition having $C_{17-20}$ lyase and 5α-reductase inhibitory activity comprising a pharmaceutical carrier and an effective inhibitory amount of a compound, or a pharmaceutically acceptable salt thereof, of the formula:

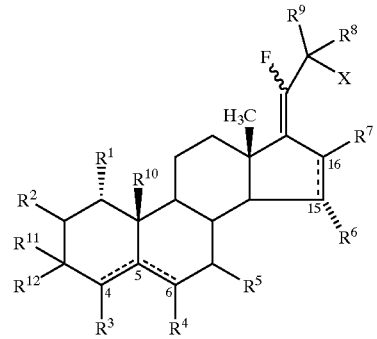

wherein:
$R^1$ is H or $C_{1-4}$ alkyl;
$R^2$ is H or $C_{1-4}$ alkyl;
$R^3$ is H, chloro, nitro, amino or $C_{1-4}$ alkyl;
$R^4$ is H or $C_{1-4}$ alkyl;
$R^5$ is H or $C_{1-4}$ alkyl;
$R^6$ is H or methyl;
$R^7$ is H or methyl;
$R^8$ is H or methyl;
$R^9$ is H or methyl;
  or $R^8$ and $R^9$ taken together is oxo;
$R^{10}$ is H or methyl;
$R^{11}$ is H;
$R^{12}$ is hydroxy;
  or $R^{11}$ and $R^{12}$ taken together is oxo;
X is H, hydroxy or methoxy;
with the proviso that when:
  a) $R^{11}$ is H and $R^{12}$ is hydroxy, bond $C_{4,5}$ is a single bond, bond $C_{5,6}$ is a double bond and bond $C_{15,16}$ is optionally a single bond or a double bond, and
  b) $R^{11}$ and $R^{12}$ taken together is oxo, bond $C_{4,5}$ is a double bond, bond $C_{5,6}$ is a single bond, bond $C_{15,16}$ is a single bond, and $R^8$ and $R^9$ are each methyl or $R^8$ and $R^9$ taken together is oxo.

20. The pharmaceutical composition according to claim 19 having $C_{17-20}$ lyase inhibitory activity.

21. The pharmaceutical composition according to claim 20 having 5α-reductase inhibitory activity.

22. A method of inhibiting $C_{17-20}$ lyase and 5α-reductase activity which comprises administering to a patient in need thereof an effective inhibitory amount of a compound, or a pharmaceutically acceptable salt thereof, of the formula:

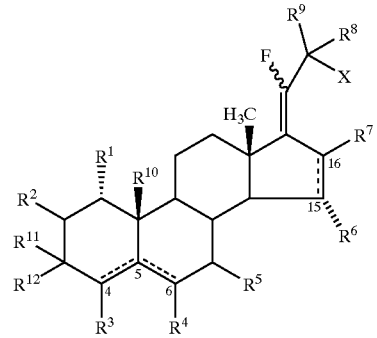

wherein:
$R^1$ is H or $C_{1-4}$ alkyl;
$R^2$ is H or $C_{1-4}$ alkyl;

$R^3$ is H, chloro, nitro, amino or $C_{1-4}$ alkyl;
$R^4$ is H or $C_{1-4}$ alkyl;
$R^5$ is H or $C_{1-4}$ alkyl;
$R^6$ is H or methyl;
$R^7$ is H or methyl;
$R^8$ is H or methyl;
$R^9$ is H or methyl;
  or $R^8$ and $R^9$ taken together is oxo;
$R^{10}$ is H or methyl;
$R^{11}$ is H;
$R^{12}$ is hydroxy;
  or $R^{11}$ and $R^{12}$ taken together is oxo;
X is H, hydroxy or methoxy;
with the proviso that when:
  a) $R^{11}$ is H and $R^{12}$ is hydroxy, bond $C_{4,5}$ is a single bond, bond $C_{5,6}$ is a double bond and bond $C_{15,16}$ is optionally a single bond or a double bond, and
  b) $R^{11}$ and $R^{12}$ taken together is oxo, bond $C_{4,5}$ is a double bond, bond $C_{5,6}$ is a single bond, bond $C_{15,16}$ is a single bond, and $R^8$ and $R^9$ are each methyl or $R^8$ and $R^9$ taken together is oxo.

23. A method of inhibiting $C_{17-20}$ lyase activity to treat a disease condition which comprises administering to a patient in need thereof an effective inhibitory amount of a compound, or a pharmaceutically acceptable salt thereof, of the formula:

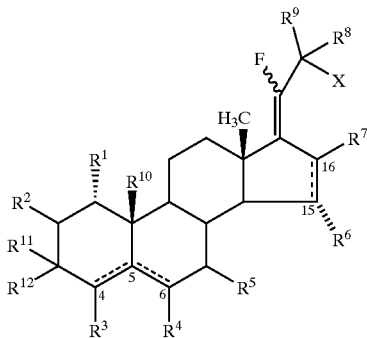

wherein:
$R^1$ is H or $C_{1-4}$ alkyl;
$R^2$ is H or $C_{1-4}$ alkyl;
$R^3$ is H, chloro, nitro, amino or $C_{1-4}$ alkyl;
$R^4$ is H or $C_{1-4}$ alkyl;
$R^5$ is H or $C_{1-4}$ alkyl;
$R^6$ is H or methyl;
$R^7$ is H or methyl;
$R^8$ is H or methyl;
$R^9$ is H or methyl;
  or $R^8$ and $R^9$ taken together is oxo;
$R^{10}$ is H or methyl;
$R^{11}$ is H;
$R^{12}$ is hydroxy;
  or $R^{11}$ and $R^{12}$ taken together is oxo;
X is H, hydroxy or methoxy;
with the proviso that when:
  a) $R^{11}$ is H and $R^{12}$ is hydroxy, bond $C_{4,5}$ is a single bond, bond $C_{5,6}$ is a double bond and bond $C_{15,16}$ is optionally a single bond or a double bond, and
  b) $R^{11}$ and $R^{12}$ taken together is oxo, bond $C_{4,5}$ is a double bond, bond $C_{5,6}$ is a single bond, bond $C_{15,16}$ is a single bond, and $R^8$ and $R^9$ are each methyl or $R^8$ and $R^9$ taken together is oxo.

24. The method according to claim 23 wherein the disease condition is an estrogen-mediated or estrogen-dependent disorder.

25. The method according to claim 24 wherein the estrogen-mediated or estrogen-dependent disorder is breast cancer.

26. The method according to claim 24 wherein the estrogen-mediated or estrogen-dependent disorder is polycystic ovarian syndrome.

27. The method according to claim 23 wherein the disease condition is an androgen-mediated or androgen-dependent disorder.

28. The method according to claim 27 wherein the androgen-mediated or androgen-dependent disorder is prostatic hyperplasia.

29. The method according to claim 27 wherein the androgen-mediated or androgen-dependent disorder is prostatic cancer.

30. The method according to claim 27 wherein the androgen-mediated or androgen-dependent disorder is virilism.

31. The method according to claim 27 wherein the androgen-mediated or androgen-dependent disorder is hirsutism.

32. The method according to claim 23 wherein the disease condition is Cushing's syndrome.

33. A method of inhibiting 5α-reductase activity to treat a disease condition which comprises administering to a patient in need thereof an effective inhibitory amount of a compound, or a pharmaceutically acceptable salt thereof, of the formula:

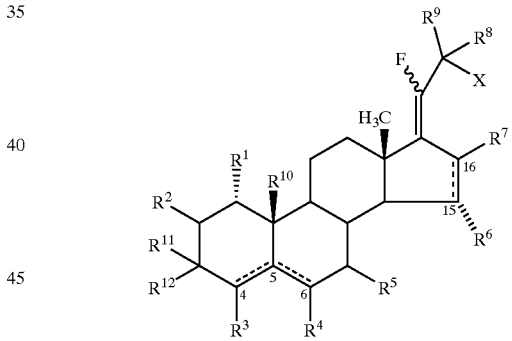

wherein:
$R^1$ is H or $C_{1-4}$ alkyl;
$R^2$ is H or $C_{1-4}$ alkyl;
$R^3$ is H, chloro, nitro, amino or $C_{1-4}$ alkyl;
$R^4$ is H or $C_{1-4}$ alkyl;
$R^5$ is H or $C_{1-4}$ alkyl;
$R^6$ is H or methyl;
$R^7$ is H or methyl;
$R^8$ is H or methyl;
$R^9$ is H or methyl;
  or $R^8$ and $R^9$ taken together is oxo;
$R^{10}$ is H or methyl;
$R^{11}$ is H;
$R^{12}$ is hydroxy;
  or $R^{11}$ and $R^{12}$ taken together is oxo;
X is H, hydroxy or methoxy;

with the proviso that when:
  a) $R^{11}$ is H and $R^{12}$ is hydroxy, bond $C_{4,5}$ is a single bond, bond $C_{5,6}$ is a double bond and bond $C_{15,16}$ is optionally a single bond or a double bond, and
  b) $R^{11}$ and $R^{12}$ taken together is oxo, bond $C_{4,5}$ is a double bond, bond $C_{5,6}$ is a single bond, bond $C_{15,16}$ is a single bond, and $R^8$ and $R^9$ are each methyl or $R^8$ and $R^9$ taken together is oxo.

34. The method according to claim 33 wherein the disease condition is an androgen-mediated or androgen-dependent disorder.

35. The method according to claim 34 wherein the androgen-mediated or androgen-dependent disorder is prostatic hyperplasia.

36. The method according to claim 34 wherein the androgen-mediated or androgen-dependent disorder is prostatic cancer.

37. The method according to claim 34 wherein the androgen-mediated or androgen-dependent disorder is acne.

38. A method for treating an androgen-mediated or androgen-dependent disorder which comprises administering to a patient in need thereof an effective inhibitory amount of an androgen receptor antagonist and an effective inhibitory amount of a compound, or a pharmaceutically acceptable salt thereof, of the formula:

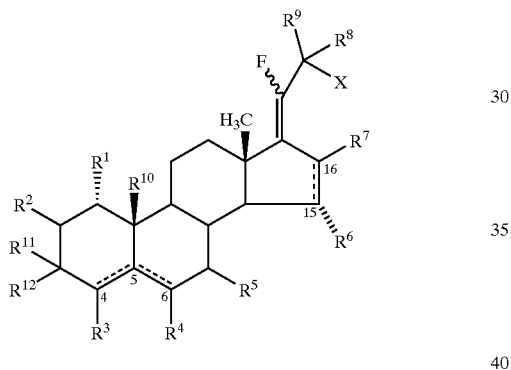

wherein:
  $R^1$ is H or $C_{1-4}$ alkyl;
  $R^2$ is H or $C_{1-4}$ alkyl;
  $R^3$ is H, chloro, nitro, amino or $C_{1-4}$ alkyl;
  $R^4$ is H or $C_{1-4}$ alkyl;
  $R^5$ is H or $C_{1-4}$ alkyl;
  $R^6$ is H or methyl;
  $R^7$ is H or methyl;
  $R^8$ is H or methyl;
  $R^9$ is H or methyl;
  or $R^8$ and $R^9$ taken together is oxo;
  $R^{10}$ is H or methyl;
  $R^{11}$ is H;
  $R^{12}$ is hydroxy;
  or $R^{11}$ and $R^{12}$ taken together is oxo;
  X is H, hydroxy or methoxy;
  with the proviso that when:
    a) $R^{11}$ is H and $R^{12}$ is hydroxy, bond $C_{4,5}$ is a single bond, bond $C_{5,6}$ is a double bond and bond $C_{15,16}$ is optionally a single bond or a double bond, and
    b) $R^{11}$ and $R^{12}$ taken together is oxo, bond $C_{4,5}$ is a double bond, bond $C_{5,6}$ is a single bond, and bond $C_{15,16}$ is a single bond.

39. The method according to claim 38 wherein the androgen receptor antagonist is flutamide.

40. A process for preparing a compound of the formula

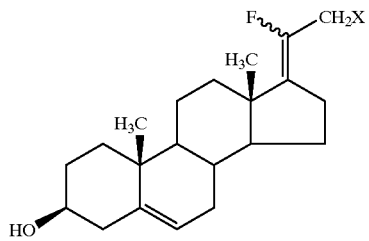

wherein X is H or hydroxy;

comprising the steps of:
  forming a ylid by reacting triethyl 2-fluoro-2-phosphonoacetate with lithium hexamethyldisilazide, condensing the ylid with a compound of the formula:

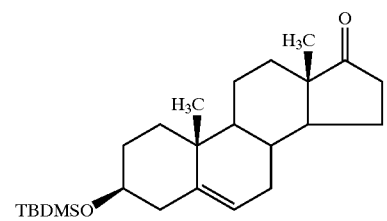

to form a vinyl fluoride ester of the formula:

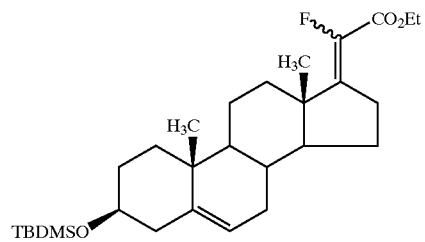

reducing the vinyl fluoride ester with diisobutylaluminum hydride to afford a hydroxymethyl vinyl fluoride of the formula:

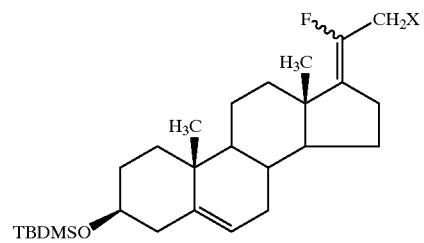

wherein X is hydroxy,
treating the hydroxymethyl vinyl fluoride with tetrabutylammonium fluoride to afford a compound of the formula:

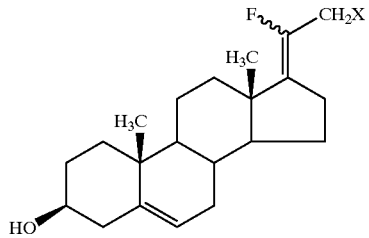

wherein X is hydroxy, or treating the hydroxymethyl vinyl fluoride with sulfur trioxide pyridine complex and reducing with lithium aluminum hydride to afford a vinyl fluoride of the formula:
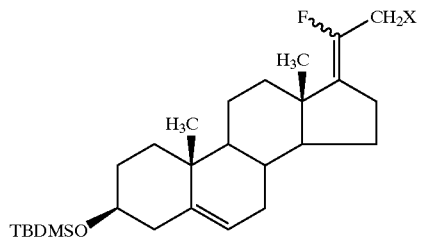
wherein X is H, and
treating the vinyl fluoride with tetrabutylammonium fluoride to afford a compound of the formula:
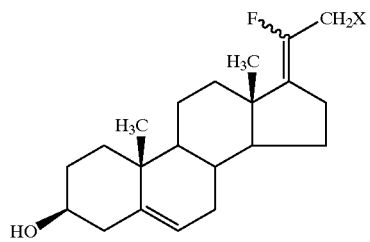
wherein X is H.
* * * * *

UNITED STATES PATENT AND TRADEMARK OFFICE
CERTIFICATE OF CORRECTION

PATENT NO. : 6,413,951 B2
DATED : July 2, 2002
INVENTOR(S) : Norton P. Peet et al.

It is certified that error appears in the above-identified patent and that said Letters Patent is hereby corrected as shown below:

Column 3,
Line 45, reads "$R^9, R^{10}, R^{11}$" and should read as -- $R^9, R^{11}$ --.

Column 8,
Scheme A, structure A5 and A4 read:

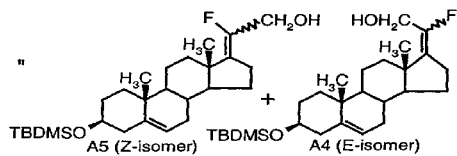

and should read as:

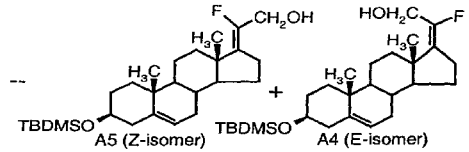

Column 14,
Line 4, reads "A16," and should read -- A11, --.

Columns 17 and 18,
Scheme D, structure D25, reads:

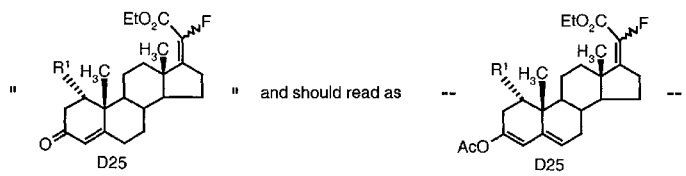

Column 21,
Line 7, reads "21-hydroxy-204-fluoro4-" and should read
-- 21-hydroxy-20ξ-fluoro-4- --.

Columns 21 and 22,
Scheme F, structure F37, reads:

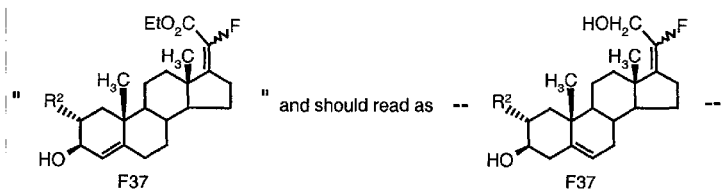

UNITED STATES PATENT AND TRADEMARK OFFICE
CERTIFICATE OF CORRECTION

PATENT NO. : 6,413,951 B2
DATED : July 2, 2002
INVENTOR(S) : Norton P. Peet et al.

It is certified that error appears in the above-identified patent and that said Letters Patent is hereby corrected as shown below:

Columns 27 and 28,
Line 1, "Scheme H title omitted" and should read -- Scheme H. $C_4$ Substituted Steroid-5-en-3-ols --.

Column 33,
Scheme L, structure L78, reads:

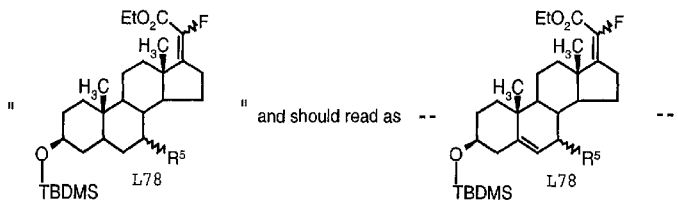

Column 40,
Line 64, reads "$C_{27}H_{45}OF_2Si$:" and should read -- $C_{27}H_{45}FO_2Si$: --.

Column 41,
Line 6, reads "$C_{27}H_{45}OF_2Si$:" and should read -- $C_{27}H_{45}FO_2Si$: --.
Line 27, reads "$C_{21}H_{31}OF_2$:" and should read -- $C_{21}H_{31}FO_2$: --.

Column 42,
Line 17, reads "$C_{21}H_{31}OF_2$:" and should read -- $C_{21}H_{31}FO_2$: --.

Column 44,
Line 2, reads "0.9 rtnol)" and should read -- 0.9 mmol) --.

Column 48,
Line 66, reads "for 2.5 nitrogen" and should read -- for 2.5 hours under a nitrogen --.

Column 51,
Line 22, reads "(I612a)" and should read -- (I61a) --.

Column 53,
Line 56, reads "3ξ-[[(1,1-Dimethylethyl)dimethylsilyl]oxy]-7α-methylandrost-5-en-17-ol" and should read -- 3β-[[(1,1-Dimethylethyl)dimethylsilyl]oxy]-7α-methylandrost-5-en-17-ol --.
Line 60, reads "9.57 anhydrous" and should read -- 9.57 mmol) in anhydrous --.

UNITED STATES PATENT AND TRADEMARK OFFICE
CERTIFICATE OF CORRECTION

PATENT NO. : 6,413,951 B2
DATED : July 2, 2002
INVENTOR(S) : Norton P. Peet et al.

It is certified that error appears in the above-identified patent and that said Letters Patent is hereby corrected as shown below:

Column 54,
Line 21, reads "3-[[(1,1-Dimethylethyl)dimethylsilyl]oxy]-7α-methylandrost-5-en-17-one" and should read -- 3β-[[(1,1-Dimethylethyl)dimethylsilyl]oxy]-7α-methylandrost-5-en-17-one --.
Line 41, reads "3β-[[(1,1-Dimethylethyl)dimethylsilyl]oxy]-7-methylandrost-5-en-17-one" and should read -- 3β-[[(1,1-Dimethylethyl)dimethylsilyl]oxy]-7β-methylandrost-5-en-17-one --.

Column 61,
Line 57, reads "7α-Butyl-20-fluoro-3-methoxypregna-3,5,17(20)-trien-21-oic" and should read -- 7α-Butyl-20ξ-fluoro-3-methoxypregna-3,5,17(20)-trien-21-oic --.

Column 63,
Line 23, reads "dichworomethane" and should read -- dichloromethane --.

Column 65,
Line 29, reads "the conversion" and should read -- the percent conversion --.

Column 73,
Line 51, reads "$R^9$ is H ormethyl;" and should read -- $R^9$ is H or methyl; --.

Column 76,
Line 1, reads "vinyl: fluoride" and should read -- vinyl fluoride --.

Signed and Sealed this

Twenty-fourth Day of December, 2002

JAMES E. ROGAN
*Director of the United States Patent and Trademark Office*